(12) United States Patent
Leen et al.

(10) Patent No.: US 12,227,764 B2
(45) Date of Patent: *Feb. 18, 2025

(54) PEPMIXES TO GENERATE MULTIVIRAL CTLS WITH BROAD SPECIFICITY

(71) Applicant: Baylor College of Medicine, Houston, TX (US)

(72) Inventors: Ann Marie Leen, Houston, TX (US); Juan Fernando Vera Valdes, Bellaire, TX (US); Cliona M. Rooney, Houston, TX (US); Ulrike Gerdemann, Cambridge, MA (US)

(73) Assignee: Baylor College of Medicine, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/443,261

(22) Filed: Jul. 23, 2021

(65) Prior Publication Data

US 2021/0348127 A1 Nov. 11, 2021

Related U.S. Application Data

(63) Continuation of application No. 15/905,176, filed on Feb. 26, 2018, now Pat. No. 11,118,164, which is a continuation of application No. 14/377,825, filed as application No. PCT/US2013/025342 on Feb. 8, 2013, now abandoned.

(60) Provisional application No. 61/596,875, filed on Feb. 9, 2012.

(51) Int. Cl.
| | |
|---|---|
| C12N 5/0783 | (2010.01) |
| A61K 39/00 | (2006.01) |
| A61K 39/12 | (2006.01) |
| C07K 14/025 | (2006.01) |
| C07K 14/03 | (2006.01) |
| C07K 14/11 | (2006.01) |
| C07K 14/135 | (2006.01) |
| C12N 7/00 | (2006.01) |

(52) U.S. Cl.
CPC ............ *C12N 5/0638* (2013.01); *A61K 39/12* (2013.01); *A61K 39/4611* (2023.05); *A61K 39/464838* (2023.05); *C07K 14/025* (2013.01); *C07K 14/03* (2013.01); *C07K 14/11* (2013.01); *C07K 14/135* (2013.01); *C12N 7/00* (2013.01); *A61K 2039/55527* (2013.01); *A61K 2039/57* (2013.01); *A61K 2039/572* (2013.01); *A61K 2039/577* (2013.01); *A61K 2039/70* (2013.01); *C12N 2501/2302* (2013.01); *C12N 2501/2304* (2013.01); *C12N 2501/2307* (2013.01); *C12N 2501/2315* (2013.01); *C12N 2710/16134* (2013.01); *C12N 2710/16234* (2013.01); *Y02A 50/30* (2018.01)

(58) Field of Classification Search
CPC ................ A61K 2039/57; A61K 39/12; A61K 2039/572; A61K 2039/5158; A61K 2039/70; C07K 14/03; C07K 14/025; C12N 2501/2304; C12N 2501/2307; C12N 2501/2315; C12N 5/0638; C12N 2501/2302; C12N 2710/16134; C12N 2710/16234; Y02A 50/30

See application file for complete search history.

(56) References Cited

U.S. PATENT DOCUMENTS

| | | | |
|---|---|---|---|
| 5,641,628 A | 6/1997 | Bianchi | |
| 5,843,405 A | 12/1998 | Middeldorp | |
| 5,869,453 A | 2/1999 | Moss et al. | |
| 5,962,318 A | 10/1999 | Rooney et al. | |
| 6,040,177 A | 3/2000 | Riddell et al. | |
| 6,143,865 A | 11/2000 | Middeldorp | |
| 6,274,378 B1 | 8/2001 | Steinman et al. | |
| 6,451,305 B1 | 9/2002 | Boussiotis et al. | |
| 6,455,299 B1 | 9/2002 | Steinman et al. | |
| 6,528,307 B1 | 3/2003 | Herlyn | |
| 6,699,477 B2 | 3/2004 | Khanna et al. | |
| 6,713,053 B1 | 3/2004 | Bach et al. | |
| 6,723,695 B1 | 4/2004 | Burrows et al. | |
| 6,821,778 B1 | 11/2004 | Engleman et al. | |
| 6,828,147 B1 | 12/2004 | Santoli et al. | |
| 7,005,131 B1 | 2/2006 | Steinman et al. | |
| 7,638,325 B2 | 12/2009 | June et al. | |
| 7,723,107 B2 | 5/2010 | Kirkin et al. | |
| 7,745,140 B2 | 6/2010 | June et al. | |
| 7,785,806 B2 | 8/2010 | Warren et al. | |

(Continued)

FOREIGN PATENT DOCUMENTS

| | | |
|---|---|---|
| CA | 2673432 A1 | 7/2008 |
| CN | 1877336 A | 12/2006 |

(Continued)

OTHER PUBLICATIONS

Bensussan et al. "Detection of membrane-bound HLA-G translated products with a specific monoclonal antibody", Proc. Natl. Acad. Sci. USA, 92:10292-10296, 1995.

(Continued)

Primary Examiner — Bao Q Li
(74) Attorney, Agent, or Firm — Norton Rose Fulbright US LLP

(57) ABSTRACT

The present invention concerns methods of generating CTLs that are able to target at least one antigen from two or more viruses. The method includes exposing mixtures of peptides for different antigens to the same plurality of PBMCs and, at least in certain aspects, expanding the cells in the presence of IL4 and IL7.

21 Claims, 29 Drawing Sheets

(56) References Cited

U.S. PATENT DOCUMENTS

| | | |
|---|---|---|
| 7,785,875 B2 | 8/2010 | Hwang et al. |
| 7,811,581 B2 | 10/2010 | Middeldorp |
| 7,846,446 B2 | 12/2010 | Cannon et al. |
| 7,951,383 B2 | 5/2011 | Murphy et al. |
| 7,994,096 B2 | 8/2011 | Kern et al. |
| 8,138,314 B2 | 3/2012 | Exley et al. |
| 8,481,051 B2 | 7/2013 | Kuzushima et al. |
| 8,546,137 B2 | 10/2013 | Cannon et al. |
| 8,722,401 B2 | 5/2014 | Groux et al. |
| 8,741,642 B2 | 6/2014 | Manjili et al. |
| 9,115,402 B2 | 8/2015 | Hacohen et al. |
| 9,255,243 B2 | 2/2016 | Wilson et al. |
| 9,963,677 B2 | 5/2018 | Leen et al. |
| 10,351,824 B2 | 7/2019 | Rooney et al. |
| 10,385,316 B2 * | 8/2019 | Leen ............... A61P 31/12 |
| 10,556,943 B2 | 2/2020 | Knutson et al. |
| 11,111,816 B2 | 9/2021 | Lad |
| 11,118,164 B2 * | 9/2021 | Leen ............... A61K 39/12 |
| 11,155,784 B2 | 10/2021 | Rooney et al. |
| 11,167,024 B2 | 11/2021 | Leen et al. |
| 2002/0051784 A1 | 5/2002 | Boussiotis et al. |
| 2002/0119121 A1 | 8/2002 | Vitiello et al. |
| 2002/0155108 A1 | 10/2002 | Barbera-Guillem |
| 2003/0148982 A1 | 8/2003 | Brenner et al. |
| 2003/0153073 A1 | 8/2003 | Rogers et al. |
| 2003/0219458 A1 | 11/2003 | Wang |
| 2004/0022761 A1 | 2/2004 | Banchereau et al. |
| 2004/0096457 A1 | 5/2004 | Huber et al. |
| 2004/0106159 A1 | 6/2004 | Kern et al. |
| 2005/0028505 A1 | 2/2005 | Schumacher |
| 2005/0106717 A1 | 5/2005 | Wilson et al. |
| 2005/0221481 A1 | 10/2005 | Migliaccio et al. |
| 2006/0045883 A1 | 3/2006 | Molldrem et al. |
| 2006/0073126 A1 | 4/2006 | Shiku et al. |
| 2006/0204509 A1 | 9/2006 | Harty et al. |
| 2006/0251664 A1 | 11/2006 | Kropshofer et al. |
| 2007/0003531 A1 | 1/2007 | Mukherji et al. |
| 2007/0048329 A1 | 3/2007 | Khanna et al. |
| 2007/0098734 A1 | 5/2007 | Cai et al. |
| 2008/0260701 A1 | 10/2008 | Hope |
| 2009/0098090 A1 | 4/2009 | Hart et al. |
| 2009/0305324 A1 | 12/2009 | Kuzushima et al. |
| 2009/0305408 A1 | 12/2009 | Chang |
| 2010/0035282 A1 | 2/2010 | Bonini et al. |
| 2010/0254958 A1 | 10/2010 | Letsch et al. |
| 2011/0059133 A1 | 3/2011 | Adhikary et al. |
| 2011/0136228 A1 | 6/2011 | Vera et al. |
| 2011/0182870 A1 | 7/2011 | Leen et al. |
| 2011/0236363 A1 | 9/2011 | Chang et al. |
| 2011/0262467 A1 | 10/2011 | Riley et al. |
| 2012/0100180 A1 | 4/2012 | Gao et al. |
| 2012/0244132 A1 | 9/2012 | Stauss et al. |
| 2013/0045491 A1 | 2/2013 | Unutmaz |
| 2013/0058909 A1 | 3/2013 | Szabolcs |
| 2013/0102075 A1 | 4/2013 | Vera et al. |
| 2013/0115617 A1 | 5/2013 | Wilson |
| 2013/0129713 A1 | 5/2013 | Rescigno et al. |
| 2013/0217122 A1 | 8/2013 | Kaplan |
| 2014/0212398 A1 | 7/2014 | Reisner et al. |
| 2015/0010519 A1 | 1/2015 | Leen et al. |
| 2015/0037297 A1 | 2/2015 | Terman |
| 2015/0044258 A1 | 2/2015 | Knaus et al. |
| 2015/0175966 A1 | 6/2015 | Vera et al. |
| 2015/0337262 A1 | 11/2015 | Ethell |
| 2016/0208216 A1 | 7/2016 | Vera et al. |
| 2016/0215351 A1 | 7/2016 | Sahin et al. |
| 2016/0296563 A1 | 10/2016 | Sourdive et al. |
| 2016/0362658 A1 | 12/2016 | Leen et al. |
| 2017/0128565 A1 | 5/2017 | O'Reilly et al. |
| 2018/0187152 A1 | 7/2018 | Leen et al. |
| 2018/0250384 A1 | 9/2018 | Leen et al. |
| 2019/0134092 A1 | 5/2019 | Knaus et al. |
| 2019/0144826 A1 | 5/2019 | Leen et al. |
| 2019/0264176 A1 | 8/2019 | Leen et al. |
| 2019/0270966 A1 | 9/2019 | Rooney et al. |
| 2020/0172864 A1 | 6/2020 | Chiang et al. |
| 2021/0348127 A1 | 11/2021 | Leen et al. |
| 2022/0001005 A1 | 1/2022 | Leen et al. |
| 2022/0152111 A1 | 5/2022 | Knaus et al. |
| 2022/0169986 A1 | 6/2022 | Leen et al. |
| 2022/0251508 A1 | 8/2022 | Leen et al. |
| 2022/0257654 A1 | 8/2022 | Vera Valdes et al. |
| 2022/0282218 A1 | 9/2022 | Leen et al. |
| 2022/0288119 A1 | 9/2022 | Vera, Valdes et al. |
| 2023/0028788 A1 | 1/2023 | Leung et al. |

FOREIGN PATENT DOCUMENTS

| | | |
|---|---|---|
| CN | 101427135 A | 5/2009 |
| EP | 2791163 B1 | 3/2017 |
| JP | H09510211 A | 10/1997 |
| JP | 2007511205 A | 5/2007 |
| JP | 2013502235 A | 1/2013 |
| JP | 2013530943 A | 8/2013 |
| NO | 2018/055191 A1 | 3/2018 |
| WO | 1994002156 A1 | 2/1994 |
| WO | 9524217 A1 | 9/1995 |
| WO | 1995027722 A1 | 10/1995 |
| WO | 1995/031208 A1 | 11/1995 |
| WO | 1998033888 A1 | 8/1998 |
| WO | 00/50569 A1 | 8/2000 |
| WO | 0142445 A2 | 6/2001 |
| WO | 2002077030 A2 | 10/2002 |
| WO | 2005028505 A2 | 3/2005 |
| WO | 2005035728 A2 | 4/2005 |
| WO | 2007/097820 A2 | 8/2007 |
| WO | 2007099341 A1 | 9/2007 |
| WO | 2007121276 A2 | 10/2007 |
| WO | 2008025992 A2 | 3/2008 |
| WO | 2008073312 A2 | 6/2008 |
| WO | 2008073313 A2 | 6/2008 |
| WO | 2008148170 A1 | 12/2008 |
| WO | 2009053109 A1 | 4/2009 |
| WO | 2011/028531 A1 | 3/2011 |
| WO | 2011024482 A1 | 3/2011 |
| WO | 2011146473 A1 | 11/2011 |
| WO | 2012/062831 A1 | 5/2012 |
| WO | 2013088114 A1 | 6/2013 |
| WO | 2013088147 A1 | 6/2013 |
| WO | 2013088148 A2 | 6/2013 |
| WO | 2013/119947 A1 | 8/2013 |
| WO | 2015075175 A1 | 5/2015 |
| WO | 2015/110397 A2 | 7/2015 |
| WO | 2016073550 A1 | 5/2016 |
| WO | 2016073595 A1 | 5/2016 |
| WO | 2016/073595 A8 | 6/2016 |
| WO | 2016/154112 A1 | 9/2016 |
| WO | 2017/049291 A1 | 3/2017 |
| WO | 2017/203368 A1 | 11/2017 |
| WO | 2018005712 A1 | 1/2018 |
| WO | 2018/052947 A1 | 3/2018 |
| WO | 2018/232467 A1 | 12/2018 |
| WO | 2019/050958 A2 | 3/2019 |
| WO | 2020198366 A1 | 10/2020 |
| WO | 2020227546 A1 | 11/2020 |
| WO | 2020255063 A1 | 12/2020 |
| WO | 2021021937 A1 | 2/2021 |
| WO | 2021034674 A1 | 2/2021 |
| WO | 2021133667 A1 | 7/2021 |
| WO | 2021189084 A1 | 9/2021 |
| WO | 2022025984 A1 | 2/2022 |
| WO | 2022064042 A1 | 3/2022 |
| WO | 2023159088 A1 | 8/2023 |

OTHER PUBLICATIONS

Binggeli et al., American Journal of Transplantation, 2007, vol. 7, pp. 1131-1139.

Blyth et al., "Bk Vims Specific T Cells Expanded Ex Vivo for Use in Cellular Therapy Show Multiple Antigen Specificity and Polyfunctional THI Responses", abstract #164, S215.

(56) References Cited

OTHER PUBLICATIONS

Blyth et al., "BK Virus-Specific T Cells for Use in Cellular Therapy Show Specificity to Multiple Antigens and Polyfunctional Cytokine Responses", Transplantation, 92(10):1077-1084, 2011.
Blyth et al., in Blood, (Nov. 20, 2009) vol. 114, No. 22, pp. 962, Meeting Info.: 51st Annual Meeting of the American-Society-of-Hematology, New Orleans, LA, USA. Dec. 5-8, 2009, Amer Soc Hematol.
Calarota et al. "Detection of Epstein-Barr vires-specific memory CD4+T cells using a peptide-based cultured enzyme-linked immunospot assay", Immunology, 2013: 139: 533-544.
Can and Karahuseyinoglu, "Concise review: human umbilical cord stroma with regard to the source of fetus-derived stem cells", Stem Cells, 25:2886-2895, 2007.
Chakera et al., Clin Exp. ImmunolSep. 2011 156 (3): 401-409.
Chia, Whay-Kuang, et al; Adoptive T-Cell Transfer and Chemotherapy in the First-Line Treatement of Metastic and/or Locally Recurrent Nasopharyngeal Carcinoma; The Am. Society of Gene & Cell Therapy,; Molecular Therapy; pp. 1-8; Jul. 29, 2013.
Dasari et al., "Prophylactic and therapeutic adenoviral vector-based multivims-specific Tcell immunotherapy for transplant patients", Mal. Ther., 3: 16058, 2016.
Dunne et al., "Selective Expansion and Partial Activation of Human NK Cells and NK Receptor-Positive T Cells by IL-2 and IL-15", Journal of Immunology, 2001, pp. 3129-3138.
Gaundar et al., "The Generation of Clinical Grade Aspergillus Fumigatus (AF) Specific Immune Cells for Adoptive Immunotherapy", abstract #168, S216.
Gerdemann et al., "Cytotoxic T lymphocytes simultaneously targeting multiple tumor-associates antigens to treat EBV negative lymphoma", Molecular Therapy, Nature Publishing Group, GB, vol. 19, No. 12, Dec. 1, 2011, pp. 2258-2268.
Gerdemann et al., "Generation of Multivirus-specific T Cells to Prevent/treat Viral Infections aftr Allogeneic Hematopoietic Stem Cell Transplant", Journal of Visualized Experiments, May 2011, vol. 51, e2736, pp. 1-6.
Gerdemann et al., "Multivirus-specific CTL for Adoptive Transfer Using In Vitro Pepmix Stimulation", Biology Blood Marrow Transplant, online Jan. 28, 2011, p. S216.
Gerdemann et al., "Nucleofection of DCs to Generate Multivirus-specific T Cells for Prevention or Treatment of Viral Infections in the Immunocompromised Host", Molecular Therapy, vol. 17, No. 9, Sep. 1, 2009, pp. 1616-1625.
Gerdemann et al., "Rapidly Generated Multivims-specific Cytotoxic T Lymphocytes for the Prophylaxis and Treatment of Viral Infections",Am. Soc. Gene Cell Ther., 20(8):1622-1632, 2012.
Gerdemann et al., "Rapidly Generated Multivirus-specific Cytotoxic T Lymphocytes for the Prophylaxis and Treatment of Viral Infections", Molecular Therapy 2012, vol. 20, No. 8, pp. 1622-1632.
Gerdemann et al., "Safety and clinical efficacy of rapidly-generated trivirus-directed T cells as treatment for adenovirus, EBV, and CMV infections after allogeneic hematopoietic stem cell transplant", Molecular Therapy, vol. 2, No. 11, Jun. 20, 2013, pp. 2112-2121.
Geyeregger et al. "Short-Term In-Vitro Expansion Improves Monitoring and Allows Affordable Generation of Virus-Specific T-Cells against Several Viruses for a Broad Clinical Application" Plos One, 2013, 8(4): e59592.
Hobeika et al., "Detailed analysis of cytomegalovirus (CMV)-specific T cells expanded for adoptive immunotherapy of CMV infection following allogeneic stem cell transplantation for malignant disease", Intl. Society for cellular Therapy, Cytotherapy, 2008, vol. 10, No. 3, pp. 289-302.
International Preliminary Report on Patentablility dated Feb. 10, 2014, during prosecution of International Application No. PCT/GB2012/053113.
International Search Report and Written Opinion issued in International Application No. PCT/US2010/46505, dated Oct. 14, 2010.
Jeffes III et al. "Therapy of recurrent high grade gliomas with surgery, and autologous mitogen activated IL-2 stimulated killer (MAK) Lymphocytes: I. Enchancement of MAK lytic activity and cytokine production by PHA and clinical use of PHA" Journal of Neuro-Oncology, 1993, vol. / 15, pp. 141-155.
Jennes et al., "Enhanced ELISPOT detection of antigen-specific T cell responses from cryopreserved specimens with addition of both IL-7 and IL-15 the Amplispot assay" Journal of Immunological Methods, 2002, vol. 270, pp. 99-108.
Kedl et al; "T Cells Compete for Antigen-bearing Antigen-presenting Cells"; J.P. Med.—The Rockfeller University Press—vol. 192, No. 8, Oct. 16, 2002.
Kedl et al; "T Cells Down-Modulate Peptide-MHC Complexes on APCs in vivo"; Published online: Dec. 3, 2001, DOI: 10.1 038/ni/742; 2002 Nature Publishing Group.
Khanna et al., Blood, Jul. 2011, vol. 118, No. 4, pp. 1121-1131.
Lapteva and Vera " Optimization Manufacture of Virus- and Tumor-Specific T Cells", Stem Cells International, Apr. 26, 2011, vol. 2011, pp. 1-8.
Leen et al., "Cytotoxic lymphocyte (CTL) therapy for the treatment of EBV negative tumors", Abstract, International Society for Cell and Gene Therapy of Cancer Annual Meeting held in Cork, Ireland, presented Sep. 4, 2009.
Leen et al., "Identification of hexon-specific CD4 and CDS T-cell epitopes for vaccine and immunotherapy," Journal of Virology, 82(1):546-554, 2008.
Leen et al., "Overcoming antigenic competition to produce multispecific cytotoxic T lymphocyte lines for adoptive transfer," Poster, 6th Annual Dan L. Duncan Cancer Center Symposium, Baylor College of Medicine, Feb. 2009, No. 374, p. 134.
Leen et al., Nature Medicine, 2006, vol. 12, No. 10, pp. 1160-1166.
Liao et al., "Transfection of RNA encoding tumor antigens following maturation of dendritic cells leads to prolonged presentation of antigen and the generation of high-affinity tumor-reactive cytotoxic T lymphocytes", Molecular Therapy, May 1, 2004, vol. 9, No. 5, pp. 757-764.
Lim et al. Journal of Translational Medicine 2009, vol. 7:72, pp. 1-11.
Maecker et al., Journal of Immunological Methods, 2001, vol. 55, pp. 27-40.
Montes et al., "Optimum in vitro expansion of human antigen-specific CD8+ T cells for adoptive transfer therapy", British Society for Immunology, Clinical and Experimental Immunology, 2005, vol. 142, pp. 292-302.
Morandi et al., " TUMOR mRNA-Transfected Dendritic Cells Stimulate the Generation of CTL that Recognize Neuroblastoma-Associated Antigens, Kill Tumor Cells: Immunotherapeutic Implications", Neoplasia, Oct. 1, 2006, vol. 8, No. 10, pp. 833-842.
Muftuoglu et al., "Use of Expanded Allogeneic Third Party BK Vims Specific Cytotoxic C6. T Cells to Target Progressive Multifocal Leukoencephalopathy",Am. Soc. Hematol., abstract #98495, 128(22):3365, 2016.
Na et al., "Human Bone Marrow as a Source of Multifunctional CMV-Specific CD4+ T Cells for Adoptive Cell Therapy" Blood, 2007, vol. 110, p. 2973.
Nair et al, "Induction of tumor-specific cyototoxic T lymphocytes in cancer patients by autologous tumor RNA-transfected dendritic cells", Annals of Surgery, Apr. 1, 2002, vol. 235, No. 4, pp. 540-549.
Olson et al., "Efficacy of Third Party BK Vims (BKV) Specific Cytotoxic T-Lymphocytes Generated by Ex Vivo Expansion for the Treatment of BKV Infection in Stem Cell Transplant Recipients, a Phase 2 Trial", Am. Soc. Hematol., abstract, 128(22):504, 2016.
Ramaswami et al., Clin Vaccine Immunol, Published on line Mar. 2, 2011, vol. 18, No. 5 815-824.
Suneetha et al., Journal of Immunological Methods, 2009, vol. 342, No. 1-2, pp. 33-48.
Tekkatte, Chandana, et al;""Humanized" Stem Cell Culture Techniques: The Animal Serum Controversy"; Stem Cells Int'l, vol. 2011; Article ID 504723; 14 pgs; Nov. 9, 2010.
Testa et al: "MHC Class I-Presented T Cell Epitopes Identified by Immunoproteomics Analysis Are Targets for a Cross Reactive Influenza-Specific T Cell Response", Plos One, vol. 7, No. 11, Nov. 7, 2012 (Nov. 7, 2012), p. e48484.

(56) References Cited

OTHER PUBLICATIONS

Trivedi et al., "Generation of CMV-specific T lymphocytes using protein-spanning pools of pp65-derived overlapping pentadecapeptides for adoptive immunotherapy", Blood, Apr. 1, 2005, vol. 105, No. 7, pp. 2793-2794.
Van Montfoort et al., "Antigen storage compartments in mature dendritic cells facilitate prolonged cytotoxic T lymphocyte cross-priming capacity", PNAS, Apr. 21, 2009, vol. 106, No. 16, pp. 6730-6735.
Vella et al., "Cytokine-induced survival of activated T cells in vitro and in vivo", Proc. Natl. Acad. Sci. USA 95, Immunology, Mar. 1998, vol. 95, pp. 3810-3815.
Vera, Juan F., et al; "Accelerated Production of Antigen-Specific T-cells for Pre-Clinical and Clinical Applications using Gas-Permeable Rapid Expansion Cultureware (G-Rex)"; Journal of Immunotherapy, Apr. 2010, vol. 33, No. 3, pp. 305-315.
Adamowicz et al., 2019, Interferon-Gamma Elispot Assay: Unique Challenges of Validating Immune Monitoring Assays in a Regulated Environment celerion Translating Science to Medicine pp. 1-4.
Aguayo-Hiraldo et al. Characterizing the Cellular Immune Response to Parainfluenza Virus 3. The Joural of Infectious Diseases; Jul. 2017, 216(2):153-161.
Ando Jun et al "Towards Phase 2/3 Trials for Epstein-Barr Virus (EBV)-Associated Malignancies", Blood, vol. 118, No. 21, Nov. 2011, p. 1727.
Baugh et al. "Infusion of cytotoxic T lymphocytes for the treatment of viral infections in hematopoietic stem cell transplant patients" Curr Opin Infect Dis. Aug. 2018; 31(4): 292-300.
Britten et al., "The use of HLA-A*0201-transfected K562 as standard antigen-presenting cells for CD8+ T lymphocytes in IFN-? ELISPOT assays," J. Immunol. Methods 259, 95-110, 2002.
Burkett et al, IL-15R expression on CD8+ T cells is dispensable for T cell memory, PNAS Apr. 15, 2003, vol. 100, No. 8.
Carpenter et al., "A side-by-side comparison of T cell reactivity to fifty-nine Mycobacterium tuberculosis antigens in diverse populations from five continents", Tuberculosis (2015) 1-9.
Cornish et al, Differential regulation of T-cell growth by IL-2 and IL-15, Blood, Jul. 15, 2006, vol. 108, No. 2.
Decaussin et al., "Expression of BARF1 Gene encoded by Epstein-Barr Virus in Nasopharyngeal Carcinoma Biopsies," cancer Res. 60, 5584-88, 2000.
Foster et al., "Autologous Designer Antigen-presenting Cells by Gene Modification of T Lymphocytes Blasts With IL-7 and IL-12," J. Immunother. 30, 506-16, 2007.
Fujita et al., " Exploiting cytokine secretion to rapidly produce multivirus-specific T cells for adoptive Immunotherapy", J Immunother., 2008, v 31, pp. 665-674.
Fujiwara et al., "Identification and in vitro expansion of CD4+ and CD8+ T cells specific for human neutrophil elastase", Blood, 103(8), pp. 3076-3083, Apr. 15, 2004 (Apr. 15, 2004).
Gerdeman et al., Blood, 2009, v. 114, Abstract 4083.
Gerdemann et al., "Immunotherapeutic strategies to prevent and treat human herpesvirus 6 reactivation after allogeneic stem cell transplantation", Blood, Jan. 3, 2013, vol. 121, No. 1, p. 207-218.
Goon et al, "Human T Cell Lymphotropic Virus (HTLV) Type-1-Specific CD8+ Cells: Frequency and Immunodominance Hierarchy", The Journal ol Inlectious Diseases, Jun. 15, 2004;189: 2294-2298.
Goon et al., "Human T Cell Lymphotropic Virus Type I (HTLV-I)-Specific CD4+ T Cells: fmmunodominance Hierarchy and Preferential Infection with HTLV-I1", The Journal of Immunology, 2004, 172: 1735-1743.
Halawi et al., "Identification of novel CD8+ T cell epitopes in human herpesvirus 6B U11 and U90", Immunity, Inflammation and Disease 2015; 3(2): 1 18-131.
Herd et al., "Major Histocompatibility Complex Class I Cytotoxic T Lymphocyte Immunity to Human Metapneumovirus (hMPV) in ndividuals with Previous hMPV Infection and Respiratory Disease", The Journal ol Inlectious Diseases, Feb. 15, 2008;197:584-92.

Heslop and Leen "T-cell therapy for viral infections" American Society of Hematology; 2013; 2013:342-7.
Huye et al., "Combing mTor Inhibitors With Rapamycin-resistant T Cells: A Two-pronged Approach to Tumor Elimination," Mol. Ther. 19, 2239-48, 2011.
Janetzki et al., Guidelines for the automated evaluation of Elispot assays 1098-114 | vol. 10 N0.7 | 2015 | Nature Protocols.
Jenkins et al "In Vivo Activation of Antigen-Specific CD4 T Cells" Annu. Rev. Immunol. 2001. 19:23-45.
Jeras et al., "Induction/Engineering, Detection, Selection, and Expansion of Clinical-Grade Human Antigen-Specific CD8+ Cytotoxic T Cell Clones for Adoptive Immunotherapy," Journal of Biomedicine and Biotechnology, vol. 2010, Article ID 705215,2010, 15 pages.
Khan et al., "T Cell Recognition Patterns of Immunodominant Cytomegalovirus Antigens in Primary and Persistent Infection", The Journal of Immunology, 2007, 178: 4455-4465.
Kim et al., "The ABCs of artificial antigen presentation", Nature Biotechnology, 22(4), pp. 403-410, Apr. 2004 (Apr. 2004).
Lee et al, HLA A2.1-restricted Cytotoxic T cells Recognizing a Range of Epstein-Barr Virus Isolates through a Defined Epitope in Latent Membrane Protein LMP2, Journal of Virology, Dec. 1993, p. 7428-7435.
Leen et al., "Multicenter study of banked third-party virus-specific T cells to treat severe viral infections after hematopoietic stem cell transplantation", Blood, Jun. 27, 2013 x vol. 121, No. 26; pp. 5113-5123.
Leen, A. et al., "Differential Immunogenicity of Epstein-Barr Virus Latent-Cycle Proteins for Human CD4+ T-Helper 1 Responses," Journal of Virology, The American Society for Microbiology, vol. 75, No. 18, p. 8649-8659, Sep. 1, 2001.
Leung et al. "Evaluation of cyclin A 1-specific T cells as a potential treatment for acute myeloid leukemia," Blood Adv, Jan. 28, 2020 (Jan. 28, 2020), vol. 4, pp. 387-397.
Liu et al, IL-15 mimics T cell receptor crosslinking in the induction of cellular proliferation, gene expression and cytotoxicity in CD8+ memory T cells, PNAS Apr. 30, 2002, vol. 99, No. 9.
Merlo et al., "The interplay between Epstein-Barr virus and the immune system: a rationale for adoptive cell therapy of EBV-related disorders, " Haematologica 95, 1769-77, 2010.
Merrick et al., "Autologous versus allogeneic peptide-pulsed dendritic cells for anti-tumour vaccination: expression of allogeneic MHC supports activation of antigen specific T cells but impairs early naive cytotoxic priming and anti-tumou therapy," Cancer Immunol. Immunother. 57, 897-906, 2008.
Mitchell Monica L et al: "Determination of Optimal Target Antigen and Immune Modulatory Approaches to Improve and Standardize Epstein-Barr Virus-Specific Adoptive T Cell Therapy", Blood, American Society of Hematology, US, vol. 124, No. 21, Nov. 14, 2014 (Nov. 14, 2014) , p. 5817.
Ngo, "Towards Phase 2/3 Trials for Epstein-Barr Virus (EBV)-Associated Malignancies," 2011 Graduate Student Symposium of the Graduate School of Biomedical Sciences at Baylor College of Medicine, p. 231, 2011.
Papadopoulou et al. "Activity of broad-spectrum T-cells as treatment for AdV, EBV, CMV, BKV, and HHV6 infections after HSCT" Sci Transl Med. 2014: 6(242).
Paul et al Development and validation of a broad scheme for prediction of HLA class II restricted T cell epitopes Journal of Immunological Methods 422 (2015) 28-34. Available online Apr. 7, 2015.
PepMix™ Peptide Pools; pp. 1-13 downloaded Feb. 13, 2021.
Peripheral blood mononuclear cell—Wikipedia; pp. 1-3; downloaded Sep. 3, 2020.
Quintarelli et al., "Cytotoxic T lymphocytes directed to the preferentially expressed antigen of melanoma (PRAME) target chronic myeloid leukemia", Blood, 112(5), pp. 1876-1885, Sep. 1, 2008 (Sep. 1, 2008).
R.J. Arasaratnam et al. "Dynamics of virus-specific T cell immunity in pediatric liver transplant recipients" Am J Transplant; Sep. 2018. 18(9): 2238-2249.
Ray et al., "Role of Individual Glycoproteins of Human Parainfluenza Virus Type 3 in the Induction of a Protective Immune Response", Journal of Virologoy, Mar. 1988, vol. 62, No. 3, pp. 783-787.

(56) References Cited

OTHER PUBLICATIONS

Redchenko & Rickinson, "Accessing Epstein-Barr Virus-Specific T-Cell Memory with Peptide-Loaded Dendritic Cells," J. Virol. 73, 334-42, 1999.
Rudolf et al., "Potent costimulation of human CD8 T cells by anti-4-1BB and anti-CD28 on synthetic artificial antigen presenting cells," Cancer Immunol. Immunother. 57, 175-83, Epub 2007.
Seig et al., "Inforection and Immunoregulation of T Lymphocytes by Parainfluenza Virus Type 2", Proceedings of the National Academy of Sciences of the U.S. A., Jul. 1994, vol. 91, No. 14, pp. 6293-6297.
Suhoski et al., "Engineering artificial antigen-presenting cells to express a diverse array of co-stimulatory molecules," Mol. Ther. 15, 981-88, 2007.
Tan et al, A re-evaluation of the frequency of CD8+ T cells specific for EBV in healthy virus carriers, Journal of Immunology 1999; 162: 1827-1835.
Taylor et al., "Mechanisms of immune suppression by interleukin-10 and transforming growth factor-.beta.: the role of T regulatory cells," Immunology 117, 433-42, 2006.
Tedcastle et al ., "The Characterization of Monoclonal Antibodies to Human Metapneumovirus and the Detection of Multiple Forms of the Virus Nucleoprotein and Phosphoprotein", Journal of Medical Virology 84: 1061-1070 (2012).
The 23rd Annual Graduate Student Research Symposium of the Graduate School of Biomedical Sciences at Baylor College of Medicine, 2011, p. 231.
Turtle & Riddell, "Artificial antigen presenting cells for use in adoptive immunotherapy," Cancer J. 16, 374-81, 2010.
Y E Z, et al; In Vitro expansion and Charcterization of Dendritic Cells Derived from Human Bon Marroe CD34+ Cells; Bone Marrow Transpaln, 1996, v 18. 997-1008.
Meij et al., Int J. Cancer, 2002, vol. 99, pp. 93-99.
Zhu et al. J. Gene. Virology, 2010, vol. 91, pp. 1577-1589.
Tzannou et al. ""Mini" bank of only 8 donors supplies CMV-directed T cells to diverse recipients," Blood Advances, Sep. 3, 2019 (Sep. 3, 2019), vol. 3, No. 17, pp. 2571-2580.
Tzannou et al. "Immunologic Profiling of Human Metapneumovirus for the Development of Targeted Immunotherapy" The Joural of Infectious Diseases; Sep. 2017, 216(6):678-687.
Tzannou et al. "Off-the-Shelf Virus-Specific T cells to Treat BK virus, human herpes virus 6, Cytomegalovirus, Epstein-Barr Virus, and Adenovirus Infections After Allogeneic Hematopoietic Stem-Cell Transplantation" Journal of Clinical Oncology; Nov. 2017, 35(31):3547-3557.
Tzannou et al., "Preventing Stem Cell Transplantation-associated Viral Infections using T-cell Therapy Immunotherapy", Immunotherapy, Aug. 7, 2015, vol. 7, No. 7, pp. 793-810.
Vasileiuou et al. "Rapid Generation of multivirus-specific T lymphocytes for the prevention and treatment of respiratory viral infections", Haematologica; 2020, vol. 105(1):235-243.
Withers et al. "Establishment and Operation of a Third-Party Virus-Specific T Cell Bank within an Allogeneic Stem Cell Transplant Program," Biology of Blood and Marrow Transplantation, Aug. 29, 2018 (Aug. 29, 2018), vol. 24, pp. 2433-2442.
Zirlik et al., Blood, Dec. 1, 2006, v.108 pp. 3865-3870.
Ahmed et al, "Preliminary Identification of Potential Vaccine Targets for the COVID-19 Coronavirus (SARS-CoV-2) Based on SARS-CoV Immunological Studies," Viruses 12(3):254, pp. 1-15 (Feb. 2020).
AlloVir Announces Positive Final Results in Phase 2 Posoleucel Multi-Virus Prevention Study in Oral Presentation at the 64th ASH Annual Meeting and Exposition, Business Wire, Sonia Choi, AlloVir, Dec. 10, 2022, 3 pages.
Amary et al., "Detection of SS18-SSX fusion transcripts in formalin-fixed paraffin-embedded neoplasms: analysis of conventional RT-PCR, qRT-PCR and dual color FISH as diagnostic tools for synovial sarcoma," Modern Pathology 20:482-496 (2007).

Anonymous: "AlloVir", "2 Posoleucel (Viralym-M, ALVR105): A multi-virus specific T cell Therapy (VST) targeting five devastating viral pathogens," Jan. 18, 2022 (Jan. 18, 2022), https://www.allovir.com/products/alvr105.
Anthony et al., "Flow cytometry using annexin V can detect early apoptosis in peripheral blood stem cell harvests from patients with leukemia and lymphoma," Bone Marrow Transplant 21:441-446, 1998.
Arons et al., "Prame Expression in Hair Cell leukemia," Leukemia Research, New York, NY US 32(9):1400-1406 (2008).
Ben-Sasson et al., IL-1 acts directly on CD4 T cells to enhance their; antigen-driven expansion and differentiation, PNAS 106(17)7119-7124 (2009).
Bollard et al., "The generation and characterization of LMP2-specific CTL for use as adoptive transfer from patients with relapsed EBV-positive Hodgkin disease," J. Immunother. Jul.-Aug. 2004; 27(4):317-27.
Carrasco et al., "Vaccination of a Melanoma Patient with Mature Dendritic Cells Pulsed with MAGE-3 Peptides Triggers the Activity of Nonvaccine Anti-Tumor Cells," The Journal of Immunology 180(5):3585-3593 (2008).
Carrum et al., "Targeting Lymphomas Using Non-Engineered, Multi-Antigen Specific T Cells", Blood, American Society of Hematology US, vol. 132, Nov. 29, 2018 (Nov. 29, 2018), p. 1685.
Cell Medica: Research CMD-003 (Citadel Study), "Cellular Immunotheraopy Treatment Antigen-Directed for EBV Lymphoma", Cell Medica, Sep. 23, 2013, https://clinicaltrials.gov/ct2/show/NCT01948180.
Cha et al., "IL-7 + IL-15 are superior to IL-2 for the ex vivo expansion of 4T1 mammary carcinoma-specific T cells with greater efficacy against tumors in vivo ," Breast Cancer Res Treat. Jul. 2010, pp. 1-22.
Dadwal, Sanjeet et al., "Posoleucel (ALVR105), an Off-the-Shelf, Multivirus-Specific T-Cell Therapy, for the Prevention of Viral Infections Post-Allogeneic Hematopoietic Cell Transplantation (allo-HCT): Results from an Open-Label Cohort of a Phase 2 Trial", Transplantation and Cellular Therapy, vol. 28, No. 3, Nov. 5, 2021 (Nov. 5, 2021), 2 pages, Elsevier, Amsterdam, NL.
De Boer et al., "Extensive early apoptosis in frozen thawed CD34+ stem cells decreases threshold doses for haematological recovery after autologous peripheral blood progenitor cell transplant," Bone marrow Transplant 29:249-255, 2002.
Diao et al., "Reduction and Functional Exhaustion of T Cells in Patients with Coronavirus Disease 2019," Front. Immunol. 11:827, pp. 1-7 (May 1, 2020).
Dienz and Rincon, "The Effects of IL-6 on CD4 T Cell Responses," Clin Immunol. Jan. 2009; 130(1): 27-33.
Fast et al: "Potential T-cell and B-cell Epitopes of 2019-nCoV", bioRxiv, Mar. 18, 2020 (Mar. 18, 2020), pp. 1-20.
Grifoni et al., "A Sequence Homology and Bioinformatic Approach Can Predict Candidate Targets for Immune Responses to SARS CoV-2," Cell Host & Microbe 27(40):671-680 (2020).
Hemmer et al., "Minimal peptide length requirements for CD4+ T cell clones-implications for molecular mimicry and T cell survival," International Immunology, vol. 12, No. 3, pp. 375-383 (2000).
Herd et al: "Cytotoxic T-Lymphocyte Epitope Vaccination Protects against Human Metapneumovirus Infection and Disease in Mice", Journal of Virology, Feb. 2006, vol. 80, No. 4, p. 2034-2044.
Hunder et al., "Treatment of Metastatic Melanoma with Autologous CD4+ t Cells Against NY-ESO-1," New England Journal of Medicine 358(25):2698-2703 (2008).
Jacobs et al., "Selective Cancer-Germline Gene Expression in Pediatric Brain Tumors," J Neurooncol, Lab. Investigation—Human/Animal Tissue, pp. 273-280 (2008).
Joshi, Shantaram et al., "Decreased immune functions of blood cells following mobilization with granulocyte colony-stimulating factor: association with donor characteristics," Blood 98(6):1963-1970 (2001).
Keirnan et al., "PepMix™ Peptide Pools for Clinical Applications: T Cell Therapy for Viral Infections after Hematopoietic Stem Cell Transplant," JPT Peptide Technologies (2012), 2 pages.

(56) References Cited

OTHER PUBLICATIONS

Kelly-Rogers et al. Activation-Induced Expression of CD56 by T Cells Is Associated With a Reprogramming of Cytolytic Activity and Cytokine Secretion Profile In Vitro. Human Immunology 67, 863-873 (2006).
Kikuta, Hideaki, "3. Human Metapneumovirus" Viruses, 2006, vol. 56, No. 2,p. 173-182.
Kindt et al., "Protective Role of the Inhibitor of Apoptosis Protein, Survivin, in Toxin-Induced Acute Renal Failure," The FASEB Journal, Federation of American Societies for Experimental Biology, US 22(2):510-521 (2008).
Koch CP, Perna AM, Pillong M, Todoroff NK, Wrede P, et al. (2013) Scrutinizing MHC-1 Binding Peptides and Their Limits of Variation. PLOS Comput Biol 9(6): el 003088, 9 pages.
Kumar et al., "Structural, glycosylation and antigenic variation between 2019 novel coronavirus (2019-nCoV) and SARS coronavirus (SARS-CoV)," Virusdisease 31(1):13-21 (2020).
Leen et al., "Contact-activated monocytes: efficient antigen presenting cells for the stimulation of antigen-specific T cells," J Immunother. Jan. 2007:30(1): 96-107.
Li et al, "T Cell Responses to Whole SARS Coronavirus in Humans," The Journal of Immunology 181(8):5490-5500 (2008).
Mielcarek et al., "Suppression of Alloantigen-Induced T-Cell Proliferation by CD14+ Cells Derived From Granulocyte Colony-Stimulating Factor-Mobilized Peripheral Blood Mononuclear Cells," Blood, vol. 89, No. 5 (Mar. 1, 1997): pp. 1629-1634.
Nawa et al., "G-CSF reduces IFN-g and IL-4 production by T cells after allogeneic stimulation by indirectly modulating monocyte function," Bone Marrow Transplantation (2000) 25, 1035-1040.
Nelson et al., "Virus-specific T-cell therapy to treat BK polyomavirus infection in bone marrow and solid organ transplant recipients," Blood advances, pp. 5745-5754 (Nov. 20, 2020).
Parks et al., "Flow Cytometry and Fluorescence-Activated Cell Sorting (FACS)," Handbook of Experimental Immunology, Chapter 29, DM Weir (ed), 1986, xx pages, Blackwell Scientific Publications, MA.
PepTivator® CMV pp65—premium grade, MACS and Peptivator, Miltenyi Biotech GmbH 2013, 4 pages.
Professor Kronenberg Declaration filed in EP 12815750 Opposition on May 15, 2019, 75 pages.
Reyes et al., "Granulocyte colony-stimulating factor (G-CSF) transiently suppresses mitogen-stimulated T-cell proliferative response," British Journal of Cancer (1999) 80(1/2):229-235 (1999).
Rooney and Leen, "Moving Successful Virus-specific T-cell Therapy for Hematopoietic Stem Cell Recipients to Late Phase Clinical Trials," Molecular Therapy-Nucleic Acids (2012) I, e55, 4 pages.
Schmid et al., "Dead Cell Discrimination with 7-aminoactinomycin Din Combination with Dual Colour Immunofluorescence in Single Laser Flow Cytometry," Cytometry 13:204-208 (1992).
Schnittger et al., in Blood, CBL Mutations Are Correlated with CMML, Frequently Associated with RUNX1 but Mutually Exclusive of JAK2V617F Mutations, Blood 114(22):962, 2 pages (Nov. 20, 2009).
Sili et al., "Large-scale expansion of dendritic cell-primed polyclonal human cytotoxic T-lymphocyte lines using lymphoblastoid cells for adoptive immunotherapy," J. Immuother. May-Jun. 2003: 26(3): 241- 56.
Song et al., "Detection of MAGE and SSX Gene Expressions by RT-nested PCR Using Common Primers in Head and Neck Cancer," Clinical and Experimental Otorhinolaryngology 1(2):97-102 (2008).
Teague et al., "Interleukin-IS rescues tolerant cos+ T cells for use in adoptive immunotherapy of established tumors," Nature Medicine 12(3):335-341 (2006).
Thevarajan et al., "Breadth of concomitant immune responses prior to patient recovery: a case report of non-severe COVID-19," Nature Medicine 26(4):453-455 (2020).
Tung et al., "Modern Flow Cytometry: A Practical Approach," Clin Lab Med 27(3):453 (2007), 15 pages.
Tzannou and Leen; Accelerating immune reconstitution after hematopoietic stem cell transplantation: Clinical & Translational Immunology 3:e11, pp. 1-10 (2014).
Vasileiou et al., "Allogeneic, Off-the-Shelf, Sars-Cov-2-Specific T Cells to Treat High-Risk Patients with COVID-19," Transplantation and Cellular Therapy 27, 3S, S1-S488, 3 pages (2021).
Zhou et al., "Either IL-2 or IL-12 Is Sufficient to Direct Thl Differentiation by Nonobese Diabetic T Cells1", The Journal of Immunology, 2003, 170:735-740.
Dadwal, Sanjeet et al., Posoleucel (ALVR105), an Off-the-Shelf, Multivirus-Specific T-CeLL Therapy, for the Prevention of Viral Infections Post-Allogeneic Hematopoietic Cell Transplantation (allo-HCT): Results from an Ope•• abel Cohort of a Phase 2 Trial, Blood, vol. 138, Supplement 1, Nov. 23, 2021, p. 1760-1762. (Poster Abstracts).
Dadwal, Sanjeet et al., "Posoleucel (ALVR105), an Off-the-Shelf, Multivirus-Specific T-CeLL Therapy, for the prevention of Viral Infections Post-Allogeneic Hematopoietic Cell Transplantation (allo-HCT): Results from an Ope•• abel Cohort of a Phase 2 Trial," 16 pages. Retrieved from <https://docs.publicnow.com/viewDoc?hash_primary=174944531E2578BE2113C21656B176A3520CC307>, 2022.
Diao et al: "Reduction and Functional Exhaustion of T Cells in Patients with Coronavirus Disease 2019 (COVID-19)", medRxiv, Feb. 20, 2020 (Feb. 20, 2020).
EP Search Report dated Apr. 4, 2023 cited in related EP Appl. No. 20777790.5.
EP Search Report dated dated Oct. 16, 2019 cited in related EP Appl. No. 19178235.8.
EP Search Report dated Feb. 7, 2013 cited in related EP Appl. No. 10814245.6.
EP Search Report dated Jul. 20, 2015 in related EP Appl. No. 13746524.1.
EP Search Report dated Mar. 20, 2019 during examination of in related EP Appl. No. 16847545.7.
EP Search Report dated May 21, 2021 cited in related EP Appl. No. 21160943.
EP Search Report dated Oct. 10, 2022 cited in related EP Appl. No. 22166731.
EP Search Report dated Sep. 27, 2016 in related EP Appl. No. 16180607.0.
Hasskarl et al "Induction of graft versus malignancy effect after unrelated allogeneic PBSCT using donor lymphocyte infusions derived from frozen aliquots of the original graft", Bone Marrow Transplantation, vol. 47, No. 2, Apr. 4, 2011 (Apr. 4, 2011), pp. 277-282.
International Preliminary Report on Patentability and Written Opinion issued for Application No. PCT/GB2012/053113, dated Feb. 10, 2014.
International Preliminary Report on Patentability for Application No. PCT/US2020/044080, dated Feb. 1. 2022.
International Preliminary Report on Patentability issued by the International Searching Authority for Application No. PCT/US2016/052487, dated Mar. 20, 2018.
International Preliminary Report on Patentability issued in International Application No. PCT/GB2012/050896 dated Jun. 17, 2014.
International Preliminary Report on Patentability issued in International Application No. PCT/GB2012/053114, dated Jun. 17, 2014.
International Preliminary Report on Patentability issued in International Application No. PCT/US2010/025209, dated Sep . 9, 2011.
International Preliminary Report on Patentability issued in International Application No. PCT/US2013/025342, dated Aug. 12, 2014.
International Preliminary Report on Patentability issued in International Application No. PCT/US2020/024726, dated Sep. 28, 2021.
International Preliminary Report on Patentability issued in International Application No. PCT/US2020/065968, dated Jun. 28, 2022.
International Preliminary Report on Patentability issued in International Application No. PCT/US2021/016266, dated Jan. 31, 2023.
International Search Report and Written Opinion issued by the International Searching Authority for Application No. PCT/IB2022/061291, dated Mar. 29, 2023.
International Search Report and Written Opinion dated Mar. 23, 2021 issued during examination of International Application No. PCT/US2020/065968.

(56) References Cited

OTHER PUBLICATIONS

International Search Report and Written Opinion issued by the International Searching Authority for Application No. PCT/US2020/044080, dated Oct. 28, 2020.
International Search Report and Written Opinion issued in International Application No. PCT/US2010/025209, dated Jul. 14, 2010.
International Search Report and Written Opinion issued in International Application No. PCT/US2016/052487, dated Dec. 19, 2016.
International Search Report and Written Opinion issued in International Application No. PCT/US2020/024726, dated Jun. 19, 2020.
International Search Report and Written Opinion issued in International Application No. PCT/US2021/016266, dated Jun. 4, 2021.
International Search Report by the International Searching Authority for Application No. PCT/GB2012/053113, dated Mar. 26, 2013.
International Search Report issued in International Application No. PCT/GB2012/053114, dated Jul. 15, 2013.
International Search Report issued in International Application No. PCT/US2013/025342, dated Aug. 11, 2013.
International Search Report dated Jun. 29, 2021 during examination of International Application No. PCT/US2021/070291.
Olson et al., "Third-Party BK Virus-Specific Cytotoxic T Lymphocyte Therapy for Hemorrhagic Cystitis Following Allotransplantation," J Clin Oncol 39:2710-2719 (2021).
Peggs et al "Directly Selected Cytomegalovirus-Reactive Donor T Cells Confer Rapid and Safe Systemic Reconstitution of Virus-Specific Immunity Following Stem Cell Transplantation", Clinical Infectious Diseases, vol. 52, No. 1, Jan. 1, 2011 (Jan. 1, 2011), pp. 49-57.
Samuel et al "CMV-reactive T cells can be isolated from G-CSF mobilised peripheral blood apheresates", Blood, vol. 116, No. 21, Nov. 19, 2010 (Nov. 19, 2010).
Samuel et al "Successful isolation and expansion of CMV-reactive T cells from G-CSF mobilized donors that retain a strong cytotoxic effector function", British Journal of Haematology, vol. 160, No. 1, Oct. 9, 2012 (Oct. 9, 2012), pp. 87-100.
Wing et al., "An Improved Method for the Detection of Cell Surface Antigens in Samples of Low Viability using Flow Cytometry," J Immunol Methods 126: 21-27 1990.
Written Opinion issued in International Application No. PCT/US2013/025342, dated Apr. 11, 2013.
Itoh et al., Nishinihon J of urology, 1998, v.60 pp. 185-190.
Gottlieb et al: "Prophylactic antigen-specific T-cells targeting seven viral and fungal pathogens after allogeneic haemopoietic stem cell transplant", Clinical & Translational Immunology 2021; e1249.
Blyth et al: "Donor-derived CMV-specific T cells reduce the requirement for CMV-directed pharmacotherapy after allogeneic stem cell transplantation", Blood, May 2, 2013 x vol. 121, No. 18, The American Society of Hematology.
Micklethwaite et al: "Ex Vivo Expansion and Prophylactic Infusion of CMV-pp65 Peptide-Specific Cytotoxic T-Lymphocytes following Allogeneic Hematopoietic Stem Cell Transplantation", Biology of Blood and Marrow Transplantation 13:707-714 (2007), American Society for Blood and Marrow Transplantation.
AlloVir, "Moltiviros-specific T Cells for the Treatment of Virus Infections After Stem Cell Transplant (CHARMS)" Study Record—ClinicalTrials.gov, May 29, 2019 (May 29, 2019).
European Supplemental Search Report dated Jul. 24, 2023 during examination of EP Appl. No. 20847823.0.
Pfeiffer T et al: "Posoleucel, an Allogeneic, Off-the-Shelf Multivirus-Specific T-Cell Therapy, for the Treatment of Refractory Viral Infections in the Post-HCT Setting", Clinical Cancer Research, vol. 29, No. 2, Jan. 17, 2023 (Jan. 17, 2023), pp. 324-330.
Vasileiou S et al: "Rapid Generation of Multivirus-Specific T Lymphocytes for the Prevention and Treatment of Respiratory Viral Infections", Blood, vol. 132, No. Suppl. 1, 3332, Nov. 29, 2018 (Nov. 29, 2018), XP086592710, 60th ASH Annual Meeting; San Diego, CA, USA; Dec. 1-8, 2018.
Vasileiou S et al: "Rapid Generation of Multivirus-Specific T Lymphocytes for the Prevention and Treatment of Respiratory Viral Infections", Biology of Blood and Marrow Transplantation, vol. 25, No. 3, 544, Mar. 2019 (Mar. 2019), p. S363, XP085593154, 2019 TCT Meetings of ASBMT and CIBMTR; Huston, TX, USA; Feb. 20-24, 2019.
Aguayo-Hiraldo et al: "Adoptive T-Cell Therapy to Prevent and Treat Parainfluenza Virus 3 (PIV-3) Infections Post Hematopoietic Stem Cell Transplant (HSCT)", Biology of Blood and Marrow Transplantation, vol. 22, No. 3, Mar. 2016 (Mar. 2016), pp. S138-S139.
Falsey, Ann "Current management of parainfluenza pneumonitis in immunocompromised patients : a review", Infection and Drug Resistance, Jan. 1, 2012 (Jan. 1, 2012), p. 121.
Fu et al., Protective cellular immunity: cytotoxic T-lymphocyte responses against dominant and recessive epitopes of influenza virus nucleoprotein induced by DNA immunization, Journal of virology, 1997, 04 months, vol. 71, No. 4, p. 2715-2721.
Fuji et al., "Adoptive immunotherapy with virus-specific T cells", Best Practice & Research Clinical Haematology, vol. 24, No. 3, 2011, pp. 413-419.
Ito Yasuhiko, et al., Antigenic Structures, vol. 39, No. 1, pp. 1989, No. 29, p. 29-45.
Johnstone C et al., "Relevance of viral context and diversity of antigen—processing routes for respiratory syncytial virus cytotoxic T-lymphocyte epitopes", The Journal of general virology, 2008, 09 months, vol. 89, p. 2194-2203.
Mao et al. "Inhibition of human parainfluenza virus type 3 infection by novel small molecules", Antiviral Research, vol. 77, No. 2, Oct. 2, 2007 (Oct. 2, 2007), pp. 83-94, Elsevier BV, NL.
Melendi et al., Mapping and Characterization of the Primary and Anamnestic H—2 d—Restricted Cytotoxic T-Lymphocyte Response in Mice against Human Metapneumovirus, Journal of Virology, vol. 81, No. 20, Oct. 2007, pp. 11461-11467.
Zavala—Vega et al., "Role of Epstein-Barr Virus in Glioblastoma", Crit Rev Oncog, 2019 , vol. 24, pp. 307-338.
Zhong W et al., Genome—45144, Wide characterization of a viral cytotoxic T lymphocyte epitope repertoire, The Journal of biological chemistry ,2003—vol. 278, No. 46, p. 45135, 05 months, 09 months.
Caruso et al., "Flow cytometric analysis of activation markers on stimulated T cells and their correlation with cell proliferation," Cytometry. Jan. 1, 1997;27(1):71-76.
Clancy et al., "Cytomegalovirus (CMV) PP65 Specific T Cells Expanded from Mobilised Peripheral Blood Stem Cell PBSC) Collections for Prophylactic Adoptive Immunotherapy," Biology of Blood and Marrow Transplantation, 2011. 2, vol. 17, No. 2, Supplement, p. S212, No. 160, 1 page.
CMD-003, Retrieved from the Internet 20150922, The Wayback Machine—; https://web.archive.org/web/20150906200237/http://www.cellmedica.co.uk:80/clinical-research/cmd-003/, 1 page.
Curotto De Lafaille et al., "CD25-T Cells Generate CD25+Foxp3+ Regulatory T Cells by Peripheral Expansion," The Journal of Immunology, vol. 173, No. 12:7259-7268, Dec. 15, 2004.
Feuchtinger et al., "Safe adoptive transfer of virus-specific T-cell immunity for the treatment of systemic adenovirus infection after allogeneic stem cell transplantation," British Journal of Haematology 134:64-76 (2006).
Hanley et al. "Expansion of T cells targeting multiple antigens of cytomegalovirus, Epstein-Barr virus and adenovirus o provide broad antiviral specificity after stem cell transplantation," Biology of Blood and Marrow Transplantation, 2011, 02, vol. 17, No. 2, Supplement, p. S212 No. 159, 1 page.
International Search Report dated Aug. 10, 2012 in PCT/GB2012/050896, 11 pages.
International Search Report and Written Opinion issued by the International Searching Authority for Application No. PCT/US20/46389, dated Nov. 13, 2020, 10 pages.
International Search Report and Written Opinion issued in International Application No. PCT/US2023/062689, dated May 11, 2023, 23 pages.
Kang et al., "Human bone marrow as a source of multifunctional CMV-specific CD4+T cells for adoptive cell therapy," Blood, American Society of Hematology, US, vol. 110, No. 11 Part I, Nov. 16, 2007 (Nov. 16, 2007), p. 873A, 2 pages.

(56) References Cited

OTHER PUBLICATIONS

Korbling et al., "Donor lymphocyte apheresis for adoptive immunotherapy compared with blood stem cell apheresis," J Clin Apher. 2001; 16(2):82-7.

Le Bert et al., "SARS-CoV-2-specific T cell immunity in cases of COVID-19 and SARS, and uninfected controls," Nature, Jul. 15, 2020, 25 pages. retrieved from URL <https://doi.org/10.1038/ss41586-020-2550-z.

Wang, X. and Rivière, I., "Manufacture of tumor- and virus-specific T lymphocytes for adoptive cell therapies", Cancer Gene Therapy, 22, pp. 85-94, Feb. 27, 2015.

Leen, A.M. et al., "Monoculture-derived T lymphocytes specific for multiple viruses expand and produce clinically relevant effects in immunocompromised individuals", Nature Medicine, 12, pp. 1160-1166, Sep. 24, 2006.

Tanoue et al., "Armed Oncolytic Adenovirus-Expressing PD-L1 Mini-Body Enhances Antitumor Effects of Chimeric Antigen Receptor T Cells in Solid Tumors", Cancer Research, vol. 77, No. 8, Apr. 15, 2017 (Apr. 15, 2017), US, pp. 2040-2051.

Rosewell Shaw et al., "Armed-Ad Gene Therapy Expressing PD-L1 Minibody Enhances the Anti-Tumor Effect of Adoptively Transferred Chimeric Antigen Receptor T-Cells for Solid Tumor Treatment", Molecular Therapy, vol. 24, No. Suppl. 1, May 4, 2016 (May 4, 2016), pp. S204-S205.

Gottschalk et al., "Harnessing the Immune System to Potentiate Oncolytics", Molecular Therapy : The Journal of the American Society of Gene Therapy, vol. 22, No. 2, Feb. 1, 2014 (Feb. 1, 2014), US, pp. 239-240.

Anonymous. "Combining Oncolytic Adenovirus (OncAd) with Tumor Directed, Adenovirusspecific T-cells for the Treatment of Neuroblastoma: Effects of OncAds on Immunosuppressive Myeloid Cells", Jan. 1, 2016 (Jan. 1, 2016), pp. 1-3. Retrieved from the Internet.

Eiz-Vesper et al. "Adoptive T-cell immunotherapy from third-party donars: charcterization of donors and set up of a T-cell donor registry", Frontiers in Immunology, vol. 3, 28, 2013.

Tzannou, Ifigenia, et al. "Adoptive T-cell therapy to prevent and treat human metapneumovirus (hMPV) infections post hematopoietic stem cell transplant (HSCT)." Biology of Blood and Marrow Transplantation 21.2 (Jan. 2, 2015): S170. D2: Leen, Ann M., Helen E. Heslop, and Malcolm.

Leen, Ann M., Helen E. Heslop, and Malcolm K. Brenner. "Antiviral T-cell therapy." Immunological reviews 258.1 (Nov. 2, 2014): 12-29.

Qian et al. "Curative or pre-emptive adenovirus-specific T-cell transfer from matched unrelated or third party haploidentical donors after HSCT, including UCB transplantations: a successful phase I/II multicenter clinical trial", Journal of Hematology & Oncology, vol. 10, 2017.

O'Reilly et al. "Virus-specific T-cell banks for 'off the shelf' adoptive therapy of refractory infections", Bone Marrow Transplantation, vol. 51, pp. 1163-1172, 2016.

Sieg et al. "Infection and immunoregulation of T lymphocytes by parainfluenza virus type 3", Proc. Natl. Acad. Sci. USA, vol. 91, pp. 6293-6297, 1994.

\* cited by examiner

| Condition A: single viruses | Adv (Hexon, Penton) | CMV (IE1, pp65) | EBV (EBNA1, LMP2, BZLF1) | BKV (LT, VP1) | RSV (N,F) | Flu (MP1, NP1) | HHV6 (U14, U90) |
|---|---|---|---|---|---|---|---|
| Condition B: immunodominant vs. subdominant viruses | \multicolumn{4}{l|}{immunodominant CMV+ RSV+Flu+HHV-6} | | subdominant Adv+ EBV+ BKV | |
| Condition C: lytic vs. latent viruses | \multicolumn{3}{l|}{lytic Adv + RSV + Flu} | \multicolumn{4}{l|}{latent CMV + EBV + HHV6 +BKV} |
| Condition D: all viruses/antigens combined | \multicolumn{7}{l|}{Adv + CMV+ EBV+BKV+ RSV+ Flu+ HHV-6} |

FIG. 5A

PEPMIXES TO GENERATE MULTIVIRAL CTLS WITH BROAD SPECIFICITY

CROSS REFERENCE TO RELATED APPLICATIONS

This application is a continuation of U.S. NonProvisional patent application Ser. No. 15/905,176 filed Feb. 26, 2018, which is a continuation of U.S. NonProvisional patent application Ser. No. 14/377,825 filed Aug. 8, 2014, which is a national phase application under 35 U.S.C. § 371 of International Application No. PCT/US13/25342 filed Feb. 8, 2013, which claims priority to U.S. Provisional Application Ser. No. 61/596,875 filed Feb. 9, 2012, all of which are incorporated herein by reference in their entirety.

STATEMENT REGARDING FEDERALLY SPONSORED RESEARCH OR DEVELOPMENT

This invention was made with government support under grants U54 HL081007 and N01-HB-10-03 awarded by National Institutes of Health. The government has certain rights in the invention.

TECHNICAL FIELD

The present invention generally concerns the fields of immunology, cell biology, molecular biology, and medicine.

BACKGROUND OF THE INVENTION

Although hematopoietic stem cell transplant (HSCT) may cure hematological malignancies and genetic disorders, extension to donors other than HLA-matched siblings has resulted in the emergence of viral infections as major contributors to post-transplant morbidity and mortality[1-4]. With the advent of more intensive viral screening and improved detection, increasing numbers of viral pathogens have been implicated in these complications, expanding from cytomegalovirus (CMV), Epstein-Barr virus (EBV), herpes-simplex virus (HSV), Adenovirus (Adv), and BK to include human herpesvirus (HHV)-6, Respiratory Syncytial virus (RSV), parainfluenza, and influenza[2]. While pharmacological agents are standard therapy for some, they have substantial toxicities, generate resistant variants, are frequently ineffective and do not provide long-term protection[5,6].

Restoration of virus-specific immunity offers an attractive alternative to conventional drugs. The inventors have shown that in vitro expanded virus-specific cytotoxic T lymphocytes (CTL) generated from stem cell donors with specificity for one (EBV), two (EBV and Adv) or three (EBV, CMV and Adv) viruses are safe and effectively prevent and treat viral infection or disease in the HSCT setting[7-9]. More recently, banked, partially HLA-matched virus-specific CTL (3rd party CTLs) are showing promise in allograft recipients with advanced viral disease[10-12].

Despite these encouraging clinical results broader implementation of T cell therapy is restricted by (i) the limited spectrum of viruses that can be effectively targeted in a single T cell line, and (ii) the logistics of manufacture. Antigenic competition between high and low frequency T cells as well as between multiple antigens expressed at different levels and competing for presentation on shared antigen presenting cells (APCs) may favor generation of lines dominated by responses to a single virus or to a restricted spectrum of viral antigens[13,14], thus limiting the antiviral coverage provided by a single T cell product. In addition, our current manufacturing process is complex, requiring infectious virus material (EBV/Adv), production of a clinical grade vector, and prolonged (10-12 weeks) in vitro culture[8-10,15]. To address this latter problem some groups have evaluated more rapid approaches for producing T cell products for adoptive transfer. These include streptamer selection to directly isolate virus-specific CD8+ T cells from peripheral blood[16], as well as the selection of cells based on cytokine production (IFN) or expression of activation markers (e.g. CD154) following antigen exposure[17-19]. However, these approaches are expensive, require a large starting blood volume, which is not always available, particularly in the matched unrelated donor setting, and cannot be applied to viruses with low circulating T cell precursor frequencies.

There is a need in the art for a mechanism by which one can rapidly generate a single preparation of polyclonal CTLs that is consistently specific for immunodominant and/or subdominant antigens derived from more than one virus, including those that are frequent causes of post-transplant disease or death, for example.

BRIEF SUMMARY OF THE INVENTION

The present invention is directed to methods and compositions that concern immune system components that are modified to immunogenically recognize particular targets. In some embodiments, the present invention concerns the development of cytotoxic T-lymphocytes (CTLs) that target a biological moiety that elicits an immune response in an individual. In specific embodiments, the present invention concerns the development of CTLs that target at least one antigen from a pathogen (including viral, bacterial, or fungal) or other disease-associated antigen. In certain aspects of the invention, the present invention concerns the development of CTLs that target antigens from at least one virus, for example. In alternative embodiments, the present invention concerns the development of CTLs that target at least one tumor antigen, for example. In at least some cases, the CTLs target antigens from two or more viruses (or two or more tumors, in alternative embodiments). In some embodiments, the CTLs target one or more, two or more, three or more, or four or more antigens from the same virus. In some embodiments, the CTLs target one antigen from more than one virus. In certain embodiments, the CTLs target one or more, two or more, three or more, or four or more antigens from different viruses.

The present invention provides significant and non-obvious improvements on methods for generating CTL lines with specificity against multiple tumor antigens or multiple viruses (for example). In the generation of CTLs with such specificity, the present invention obviates the need for dendritic cells in the preparation of such lines. In some cases, the antigen is presented to PBMCs in the form of one or more peptides that span some or all of the antigen. The antigenic peptides may be provided to the PBMCs in a library of peptide mixtures, which may be referred to as pepmixes. In other aspects of the invention, in the preparation of the CTLs the invention allows for the pooling of a variety of pepmixes. In some cases, the collection of antigens may include both immunodominant and subdominant antigens, yet despite the presence of immunodominant antigens in the collection with subdominant antigens, CTLs specific antigens including subdominant antigens are surprisingly generated.

In some embodiments of the invention, an individual is in need of the methods and/or compositions of the invention. In specific embodiments, the individual is immunocompromised (which for example, may be defined as an individual whose ability to fight infectious disease or cancer with the immune system is compromised or entirely absent). In specific embodiments, the immunocompromised individual has had a stem cell transplant, has had an organ transplant and/or has received one or more cancer treatments, including chemotherapy or radiation, for example. In some cases, the individual acquired or inherited immune deficiency disorder. In some embodiments, those that are immunocompromised by their disease and/or its treatment are provided methods and/or compositions if the invention.

In some embodiments of the invention, there is a mechanism by which one can rapidly generate a single preparation of polyclonal (for example, CD4+ and CD8+) CTLs that are consistently specific for a variety of immunodominant and/or subdominant antigens derived from one or more viruses (for example, EBV, CMV, Adv, BK virus, HHV6, RSV and Influenza) that are frequent causes of post transplant disease or death. The invention is readily adaptable to clinical implementation and is useful as an "off the shelf" broad spectrum antiviral agent. The invention uses standardized (synthetic) peptides as a stimulus and enhancement of cytokines to promote the survival and expansion of T cells, is readily adaptable to clinical implementation, and is useful as a safe and effective broad spectrum antiviral agent for all high risk transplant recipients, for example.

In some embodiments of the invention, there is a method of generating cytotoxic T-lymphocytes (CTLs) that target at least one antigen from two or more viruses, comprising the steps of: contacting a plurality of peripheral blood mononuclear cells with at least two libraries of peptides, said libraries of peptides each comprising peptides that correspond to a particular viral antigen; and expanding the plurality of cells in the presence of one or more cytokines. In specific embodiments, the method occurs in the absence of exposing the libraries to isolated peptide-pulsed dendritic cells prior to expanding the CTLs. In certain embodiments, the one or more cytokines are selected from the group consisting of IL4, IL7 and a combination thereof. In some embodiments, the peptides are further defined as peptides that overlap in sequence to span part or all of a viral antigen. For example, in certain aspects the peptides overlap by at least three, four, five, or six amino acids, and in some embodiments the peptides are at least six, seven, or eight or more amino acids in length.

In some embodiments of the invention, there viruses targeted in the invention are selected from the group consisting of EBV, CMV, Adenovirus, BK virus, HHV6, RSV, Influenza, Parainfluenza, Bocavirus, Coronavirus, LCMV, Mumps, Measles, Metapneumovirus, Parvovirus B, Rotavirus, West Nile Virus, JC, HHV7, and a combination thereof. In specific aspects, the virus is EBV and the antigen is selected from the group consisting of EBNA1, LMP2, and BZLF1. In specific aspects, the virus is CMV and the antigen is selected from the group consisting of IE1 and pp65. In specific cases, the virus is Adv and the antigen is selected from the group consisting of Hexon and penton. In some embodiments, the virus is BK virus and the antigen is selected from the group consisting of LT and VP-1. In some embodiments, the virus is HHV6 and the antigen is selected from the group consisting of U14 and U90. In specific aspects, the virus is RSV and the antigen is selected from the group consisting of N and F. In certain embodiments, the virus is Influenza and the antigen is selected from the group consisting of MP1 and NP1.

In at least some methods of the invention, the CTLs generated thereby are administered to an individual, for example, an immunocompromised individual. In some cases, the individual has had allogeneic stem cell transplant. In specific embodiments, the cells are administered by injection, such as intravenous, intramuscular, intradermal, subcutaneous, intraperitoneal injection, and so forth, for example. In some embodiments, the individual has lymphoma or leukemia. In some embodiments, the CTLs are further defined as polyclonal CD4+ and CD8+ CTLs. The PBMCs may be allogeneic to the individual or are autologous to the individual. In some embodiments, the methods of the invention further comprise the step of exposing the CTLs to one or more compositions that stimulate cell division, such as phytohemagglutinin; in some aspects the compound is a mitogen.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which:

(FIG. 1A). FIG. 1B CD3+ T cell proliferation in the different culture conditions as evaluated by CFSE dilution. M1 shows the percentage of cells that underwent at least 7 cell doublings on day 10 after stimulation. Bulk cultures were analyzed for T and NK-cell marker expression on day 10 after activation. Mean expression+/−SEM in CTL lines generated from 5 donors are shown in FIG. 1C. FIG. 1D shows cytokine production from CD3/CD4+ (helper) and CD3/CD8+ (cytotoxic) CTLs on day 9 after initiation in one representative donor (dot plots shown were gated on CD3+ cells). Summary intracellular cytokine production results from three donors (mean+/−STDEV) are shown in FIG. 1E. Finally the cytokine production profile of pp65-specific CTL initiated with or without cytokines was evaluated by multiplex assay using supernatant harvested 18 h after antigenic restimulation (n=4). Th1 cytokines are shown in the left panel while prototypic Th2 cytokines are shown in the right panel (FIG. 1F). Presence of regulatory T cells were evaluated by FoxP3 staining. Plots shown are gated on CD3+/CD4+ CTLs (FIG. 1G).

FIG. 2A CTLs were stimulated either directly with a pp65 pepmix or using DCs nucleofected with a DNA plasmid encoding the same antigen. Cell expansion was evaluated by counting using trypan blue exclusion (n=4). FIG. 2B shows the expression of cell surface markers (average+/−STDEV expression) on CTLs 11 days after stimulation (n=4). The breadth of T cell reactivity in plasmid and pepmix-activated pp65-specific CTLs was evaluated by IFN ELIspot on day 9 using a total of 22 mini peptide pools representing all pp65 peptides. Data were normalized to 100% for maximum number of SFC per $1 \times 10^5$ CTL. (FIG. 2C). FIG. 2D shows the TCR avidity of plasmid vs. pepmix activated CTL generated from 2 representative donors. To assess avidity pp65-CTLs were stimulated with serial dilutions of pp65 pepmix (pp65) or relevant (HLA-matched) epitope peptides (NLV, QAD). IFN release of stimulated CTLs was evaluated by ELIspot assay and maximum SFC/$1 \times 10^5$ cells was normalized to 100% for comparison purposes.

FIG. 3A shows a schematic of three peptide libraries spanning a portion of Adv-Hexon that were used for CTL initiation. Peptide libraries consisted of 15aa, 20aa or 30aa peptides covering the immunogenic FIG. 3C-terminal 414aa of Adv-Hexon. FIG. 3B Phenotypic analysis of CTLs performed on day 10 after stimulation (n=6). Results are shown as mean+/−SEM. Breadth of reactivity was tested using IFNγ ELIspot as a readout, with the 15mer Hexon overlapping peptide library divided into mini-pools such that each pool contained 5-6 contiguous peptides, as a stimulus.

FIGS. 5A-5E: Generation of multivirus-specific CTLs. FIG. 5A shows a schematic of antigen pooling strategy for CTL initiation. PBMCs were stimulated with pepmixes pooled by virus (FIG. 5A), divided into sub-pools—immunodominant and subdominant (FIG. 5B), divided into sub-pools encompassing antigens from latent or lytic viruses (FIG. 5C), and finally all antigens were pooled together in a mastermix (FIG. 5D). After activation PBMCs were pooled and transferred to the G-Rex10 ($15 \times 10^6$/G-Rex). After 10 days the specificity of the CTL lines generated using these 4 pooling strategies were analyzed using IFN ELIspot assay as readout and individual pepmixes as a stimulus. Results from 2 representative donors are presented in FIG. 5B showing no difference in the specificity of lines. FIG. 5C confirms that multivirus CTL can be reproducibly generated by pooling all pepmixes into one mastermix for activation (n=8). Results are expressed as SFC/$1 \times 10^5$ input cells+/−SEM. Control was IFN release in response to stimulation with an irrelevant pepmix. Antigen specificity of CD3/CD8+ (cytotoxic) and CD3+CD8− (helper) T cells was evaluated by intracellular IFN staining after overnight stimulation with the equivalent antigens. Results from one representative donor are shown in FIG. 5D. FIG. 5E shows that the lines are polyfunctional as assessed using ICS for IFN and TNF in one representative donor.

FIG. 6A shows the expansion of CTLs from initiation (day 0) to day 16, following a 2nd stimulation on day 9/10 (n=4). CTL expansion was evaluated using trypan blue exclusion and results are shown as mean cell numbers+/−STDEV. FIG. 6B shows results from 1 representative donor illustrating the antigen specificity of CD3/CD8+ and CD3/CD8− (CD4+) CTLs after the 2nd round of stimulation using IFN ICS. FIG. 6C shows summary results from 6 donors after the 1st (day 9) and 2nd (day 16) stimulation, using IFN ELIspot as a readout. Results are expressed as SFC/$1 \times 10^5$ input cells+/−STDEV and the control was IFN release in response to stimulation with irrelevant pepmix. The cytotoxic abilities of the generated CTLs were evaluated by standard 4-6 hr $Cr^{51}$ release assay using pepmix-pulsed PHA blasts as targets. Specific lysis after the 1st and 2nd stimulation from 2 representative donors are shown in FIG. 6D.

DETAILED DESCRIPTION OF THE INVENTION

I. Definitions

Figure 1A:
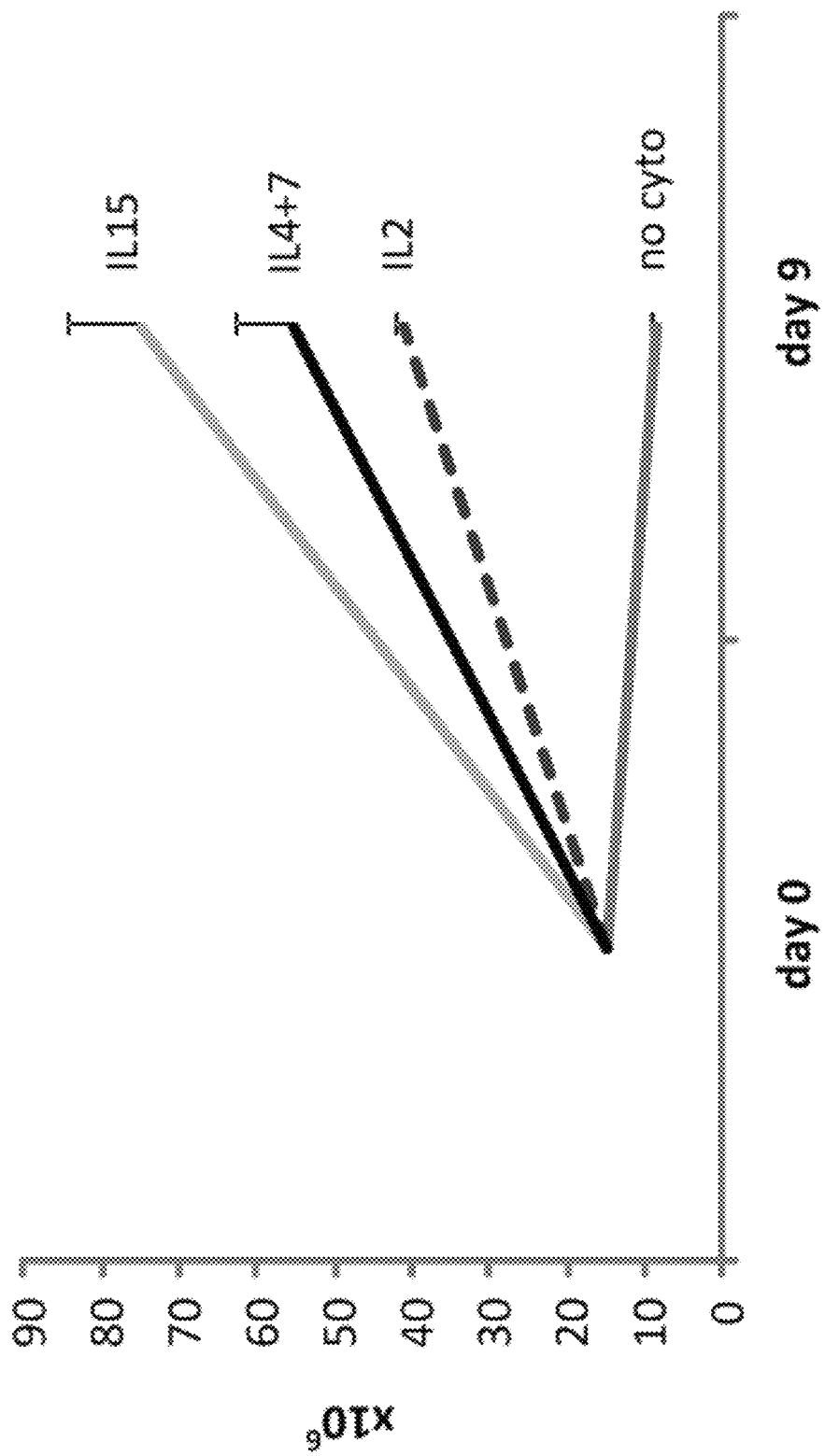
FIGS. 1A-1G: Growth promoting cytokines enhance the activation and expansion of antigen-specific CTLs. PBMC were stimulated with pp65 pepmix in the presence of IL2, IL15, IL4+7 or without exogenous cytokines. Cell expansion were evaluated after 9-11 days of culture by cell counting using trypan blue exclusion (n=5). Results are shown as mean cell numbers+/−SEM.

In keeping with long-standing patent law convention, the words "a" and "an" when used in the present specification in concert with the word comprising, including the claims, denote "one or more." Some embodiments of the invention may consist of or consist essentially of one or more elements, method steps, and/or methods of the invention. It is contemplated that any method or composition described herein can be implemented with respect to any other method or composition described herein.

The term "tumor antigen" as used herein refers to an antigenic substance produced/expressed on tumor cells and which triggers an immune response in the host.

The term "viral antigen" as used herein refers to an antigen that is protein in nature and is closely associated with the virus particle. In specific embodiments, a viral antigen is a coat proteins.

II. General Embodiments of the Invention

In certain aspects of the invention, the present invention concerns the development of CTLs that target one or more antigens from at least one virus or at least one tumor antigen, for example. In some cases, the CTLs target one or more antigens from two or more viruses or two or more tumors.

The present invention concerns methods for generating CTL lines with specificity against multiple tumor antigens or multiple viruses in at least general embodiments. In methods of producing CTLs the antigen is presented to PBMCs (for example) in the form of one or more peptides that span some or all of the antigen. The antigenic peptides may be provided to the PBMCs in a library of peptide mixtures, which may be referred to as pepmixes, and multiple libraries of pepmixes may be provided to the same collection of PBMCs. In some embodiments, the collection includes both immunodominant and subdominant antigens.

In some embodiments, the present invention is utilized in individuals after hematopoietic stem cell transplantation (HSCT) Severe and fatal viral infections remain common after HSCT. Adoptive transfer of cytotoxic T lymphocytes (CTLs) specific for EBV, CMV and Adenoviral antigens can treat infections that are impervious to conventional therapies, but broader implementation and extension to additional viruses are limited by competition between virus-derived antigens and time-consuming and laborious manufacturing procedures. The invention provides a system that rapidly generates a single preparation of polyclonal (CD4+ and CD8+) CTLs that is consistently specific for 15 immunodominant and subdominant antigens derived from 7 viruses (EBV, CMV, Adv, BK, HHV6, RSV and Influenza) that commonly cause post-transplant morbidity and mortality. CTLs can be rapidly produced (10 days) by a single stimulation of donor PBMCs with a peptide mixture spanning the target antigens in the presence of the potent pro-survival cytokines IL4 and IL7. This approach reduces the impact of antigenic competition with a consequent increase in the antigenic repertoire and frequency of virus-specific T cells. The present invention can be readily introduced into clinical practice and is a cost-effective alternative to common anti-viral prophylactic agents for allogeneic HSCT recipients.

III. Pathogens and Pathogenic Antigens

In some embodiments of the invention, the generated CTLs are provided to an individual that has or is at risk of having a pathogenic infection, including a viral, bacterial, or fungal infection. The individual may or may not have a deficient immune system. In some cases, the individual has a viral, bacterial, or fungal infection following organ or stem cell transplant (including hematopoietic stem cell transplantation), or has cancer or has been subjected to cancer treatment, for example. In some cases the individual has infection following an acquired immune system deficiency.

The infection in the individual may be of any kind, but in specific embodiments the infection is the result of one or more viruses. The pathogenic virus may be of any kind, but in specific embodiments it is from one of the following families: Adenoviridae, Picornaviridae, Herpesviridae, Hepadnaviridae, Flaviviridae, Retroviridae, Orthomyxoviridae, Paramyxoviridae, Papovaviridae, Polyomavirus, Rhabdoviridae, or Togaviridae. In some embodiments, the virus produces antigens that are immunodominant or subdominant or produces both kinds. In specific cases, the virus is selected from the group consisting of EBV, CMV, Adenovirus, BK virus, HHV6, RSV, Influenza, Parainfluenza, Bocavirus, Coronavirus, LCMV, Mumps, Measles, Metapneumovirus, Parvovirus B, Rotavirus, West Nile Virus, Spanish influenza, and a combination thereof.

In some aspects the infection is the result of a pathogenic bacteria, and the present invention is applicable to any type of pathogenic bacteria. Exemplary pathogenic bacteria include at least *Mycobacterium tuberculosis, Mycobacterium leprae, Clostridium botulinum, Bacillus anthracis, Yersinia pestis, Rickettsia prowazekii, Streptococcus, Pseudomonas, Shigella, Campylobacter*, and *Salmonella*.

In some aspects the infection is the result of a pathogenic fungus, and the present invention is applicable to any type of pathogenic fungus. Exemplary pathogenic fungi include at least *Candida, Aspergillus, Cryptococcus, Histoplasma, Pneumocystis*, or *Stachybotrys*.

IV. Tumor Antigens

In embodiments wherein multiTAA-specific CTL are employed for the treatment and/or prevention of cancer, a variety of TAA may be targeted. Tumor antigens are substances produced in tumor cells that trigger an immune response in a host.

Exemplary tumor antigens include at least the following: carcinoembryonic antigen (CEA) for bowel cancers; CA-125 for ovarian cancer; MUC-1 or epithelial tumor antigen (ETA) or CA15-3 for breast cancer; tyrosinase or melanoma-associated antigen (MAGE) for malignant melanoma; and abnormal products of ras, p53 for a variety of types of tumors; alphafetoprotein for hepatoma, ovarian, or testicular cancer; beta subunit of hCG for men with testicular cancer; prostate specific antigen for prostate cancer; beta 2 microglobulin for multiple myelom and in some lymphomas; CA19-9 for colorectal, bile duct, and pancreatic cancer; chromogranin A for lung and prostate cancer; TA90 for melanoma, soft tissue sarcomas, and breast, colon, and lung cancer. Examples of tumor antigens are known in the art, for example in Cheever et al., 2009, which is incorporated by reference herein in its entirety.

Specific examples of tumor antigens include at least CEA, MHC, CTLA-4, gp100, mesothelin, PD-L1, TRP1, CD40, EGFP, Her2, TCR alpha, trp2, TCR, MUC1, cdr2, ras, 4-1BB, CT26, GITR, OX40, TGF-α. WT1, MUC1, LMP2, HPV E6 E7, EGFRvIII, HER-2/neu, MAGE A3, p53 non-mutant, NY-ESO-1, PSMA, GD2, Melan A/MART1, Ras mutant, gp 100, p53 mutant, Proteinase3 (PR1), bcr-abl, Tyrosinase, Survivin, PSA, hTERT, EphA2, PAP, ML-IAP, AFP, EpCAM, ERG (TMPRSS2 ETS fusion gene), NA17, PAX3, ALK, Androgen receptor, Cyclin B1, Polysialic acid, MYCN, RhoC, TRP-2, GD3, Fucosyl GM1, Mesothelin, PSCA, MAGE A1, sLe(a), CYP1B1, PLAC1, GM3, BORIS, Tn, GloboH, ETV6-AML, NY-BR-1, RGS5, SART3, STn, Carbonic anhydrase IX, PAX5, OY-TES1, Sperm protein 17, LCK, HMWMAA, AKAP-4, SSX2, XAGE 1, B7H3, Legumain, Tie 2, Page4, VEGFR2, MAD-CT-1, FAP, PDGFR-β, MAD-CT-2, and Fos-related antigen 1, for example.

V. Generation of Pepmix Libraries

In some embodiments of the invention, a library of peptides is provided to PBMCs ultimately to generate CTLs. The library in particular cases comprises a mixture of peptides ("pepmixes") that span part or all of the same antigen. Pepmixes utilized in the invention may be from commercially available peptide libraries made up of peptides that are 15 amino acids long and overlapping one another by 11 amino acids, in certain aspects. In some cases, they may be generated synthetically. Examples include those from JPT Technologies (Springfield, VA) or Miltenyi Biotec (Auburn, CA). In particular embodiments, the peptides are at least 7, 8, 9, 10, 11, 12, 13, 14, 15, 16, 17, 18, 19, 20, 21, 22, 23, 24, 25, 26, 27, 28, 29, 30, 31, 32, 33, 34, or 35 or more amino acids in length, for example, and in specific embodiments there is overlap of at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, or 34 amino acids in length, for example. The mixture of different peptides may include any ratio of the different peptides, although in some embodiments each particular peptide is present at substantially the same numbers in the mixture as another particular peptide.

VI. Combination Therapy

In certain embodiments of the invention that concern CTLs generated against tumor antigens, methods of the present invention for clinical aspects are combined with other agents effective in the treatment of hyperproliferative disease, such as anti-cancer agents. An "anti-cancer" agent is capable of negatively affecting cancer in a subject, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer. More generally, these other compositions would be provided in a combined amount effective to kill or inhibit proliferation of the cell. This process may involve contacting the cancer cells with the expression construct and the agent(s) or multiple factor(s) at the same time. This may be achieved by contacting the cell with a single composition or pharmacological formulation that includes both agents, or by contacting the cell with two distinct compositions or formulations, at the same time, wherein one composition includes the expression construct and the other includes the second agent(s).

Tumor cell resistance to chemotherapy and radiotherapy agents represents a major problem in clinical oncology. One goal of current cancer research is to find ways to improve the efficacy of chemo- and radiotherapy by combining it with gene therapy. For example, the herpes simplex-thymidine kinase (HS-tK) gene, when delivered to brain tumors by a retroviral vector system, successfully induced susceptibility to the antiviral agent ganciclovir[51]. In the context of the present invention, it is contemplated that cell therapy could be used similarly in conjunction with chemotherapeutic, radiotherapeutic, or immunotherapeutic intervention, in addition to other pro-apoptotic or cell cycle regulating agents.

Alternatively, the present inventive therapy may precede or follow the other agent treatment by intervals ranging from minutes to weeks. In embodiments where the other agent and present invention are applied separately to the individual, one would generally ensure that a significant period of time did not expire between the time of each delivery, such that the agent and inventive therapy would still be able to exert an advantageously combined effect on the cell. In such instances, it is contemplated that one may contact the cell with both modalities within about 12-24 h of each other and, more preferably, within about 6-12 h of each other. In some situations, it may be desirable to extend the time period for treatment significantly, however, where several d (2, 3, 4, 5, 6 or 7) to several wk (1, 2, 3, 4, 5, 6, 7 or 8) lapse between the respective administrations.

Various combinations may be employed, present invention is "A" and the secondary agent, such as radio- or chemotherapy, is "B":

| A/B/A | B/A/B | B/B/A | A/A/B | A/B/B | B/A/A | A/B/B/B | B/A/B/B |
| B/B/B/A | B/B/A/B | A/A/B/B | A/B/A/B | A/B/B/A | B/B/A/A |
| B/A/B/A | B/A/A/B | A/A/A/B | B/A/A/A | A/B/A/A | A/A/B/A |

It is expected that the treatment cycles would be repeated as necessary. It also is contemplated that various standard therapies, as well as surgical intervention, may be applied in combination with the inventive cell therapy.

A. Chemotherapy

Cancer therapies also include a variety of combination therapies with both chemical and radiation based treatments. Combination chemotherapies include, for example, abraxane, altretamine, docetaxel, herceptin, methotrexate, novantrone, zoladex, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabien, navelbine, farnesyl-protein tansferase inhibitors, transplatinum, 5-fluorouracil, vincristin, vinblastin and methotrexate, or any analog or derivative variant of the foregoing.

B. Radiotherapy

Other factors that cause DNA damage and have been used extensively include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

C. Immunotherapy

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

Immunotherapy, thus, could be used as part of a combined therapy, in conjunction with the present cell therapy. The general approach for combined therapy is discussed below. Generally, the tumor cell must bear some marker that is amenable to targeting, i.e., is not present on the majority of other cells. Many tumor markers exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155.

D. Genes

In yet another embodiment, the secondary treatment is a gene therapy in which a therapeutic polynucleotide is administered before, after, or at the same time as the present invention clinical embodiments. A variety of expression products are encompassed within the invention, including inducers of cellular proliferation, inhibitors of cellular proliferation, or regulators of programmed cell death.

E. Surgery

Approximately 60% of persons with cancer will undergo surgery of some type, which includes preventative, diagnostic or staging, curative and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and miscopically controlled surgery (Mohs' surgery). It is further contemplated that the present invention may be used in conjunction with removal of superficial cancers, precancers, or incidental amounts of normal tissue.

Upon excision of part of all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

F. Other Agents

It is contemplated that other agents may be used in combination with the present invention to improve the therapeutic efficacy of treatment. These additional agents include immunomodulatory agents, agents that affect the upregulation of cell surface receptors and GAP junctions, cytostatic and differentiation agents, inhibitors of cell adhesion, or agents that increase the sensitivity of the hyperproliferative cells to apoptotic inducers. Immunomodulatory agents include tumor necrosis factor; interferon alpha, beta, and gamma; IL-2 and other cytokines; F42K and other cytokine analogs; or MIP-1, MIP-1beta, MCP-1, RANTES, and other chemokines. It is further contemplated that the upregulation of cell surface receptors or their ligands such as Fas/Fas ligand, DR4 or DR5/TRAIL would potentiate the apoptotic inducing abilities of the present invention by establishment of an autocrine or paracrine effect on hyperproliferative cells. Increases intercellular signaling by elevating the number of GAP junctions would increase the anti-hyperproliferative effects on the neighboring hyperproliferative cell population. In other embodiments, cytostatic or differentiation agents can be used in combination with the present invention to improve the anti-hyerproliferative efficacy of the treatments. Inhibitors of cell adhesion are contemplated to improve the efficacy of the present invention. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with the present invention to improve the treatment efficacy.

Hormonal therapy may also be used in conjunction with the present invention or in combination with any other cancer therapy previously described. The use of hormones may be employed in the treatment of certain cancers such as breast, prostate, ovarian, or cervical cancer to lower the level or block the effects of certain hormones such as testosterone or estrogen. This treatment is often used in combination with at least one other cancer therapy as a treatment option or to reduce the risk of metastases.

DNA methyltransferase inhibitors and/or histone deacetylase inhibitors. Exemplary DNA methyltransferase inhibitors include, for example, 5-azacytidine, 5-aza-2'-deoxycytidine, 1-beta-D-arabinofuranosyl-5-azacytosine and dihydro-5-azacytidine. Exemplary HDAC inhibitors include hydroxamic acids, such as trichostatin A; cyclic tetrapeptides (such as trapoxin B), and the depsipeptides; benzamides; electrophilic ketones; and the aliphatic acid compounds such as phenylbutyrate and valproic acid.

VII. Kits of the Invention

Any of the compositions described herein may be comprised in a kit. In a non-limiting example, a library of pepmixes may be comprised in a kit, any type of cells may be provided in the kit, and/or reagents for manipulation of pepmixes and/or cells may be provided in the kit. The components are provided in suitable container means.

The kits may comprise a suitably aliquoted compositions of the present invention. The components of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one component in the kit, the kit also will generally contain a second, third or other additional container into which the additional components may be separately placed. However, various combinations of components may be comprised in a vial. The kits of the present invention also will typically include a means for containing the components in close confinement for commercial sale. Such containers may include injection or blow-molded plastic containers into which the desired vials are retained.

However, the components of the kit may be provided as dried powder(s). When reagents and/or components are provided as a dry powder, the powder can be reconstituted by the addition of a suitable solvent. It is envisioned that the solvent may also be provided in another container means.

EXAMPLES

The following examples are presented in order to more fully illustrate the preferred embodiments of the invention. They should in no way, however, be construed as limiting the broad scope of the invention.

Example 1

IL2, IL15 and IL4+7 Promote the Expansion of Peptide-Activated T Cells In Vitro To increase the range of viral antigens that could be recognized by a single CTL line and to mitigate the impact of antigenic competition in order to retain both high and low frequency T cells, the inventors stimulated PBMCs in the presence of different Th1, pro-proliferative and pro-survival cytokines. The inventors then compared the frequency and repertoire of responding cells to those generated by conventional activation in the absence of cytokines. In exploratory experiments PBMCs were simulated with a pepmix (peptide library of overlapping 15mers) spanning the immunodominant CMV-pp65 antigen, then expanded without cytokines, or with media supplemented with (i) IL15 (5 ng/ml), (ii) IL2 (20 U/ml), or (iii) IL4 (1666 U/ml)+IL7 (10 ng/ml). After 9-12 days the inventors assessed cell expansion, phenotype, specificity and function.

Figure 1B:
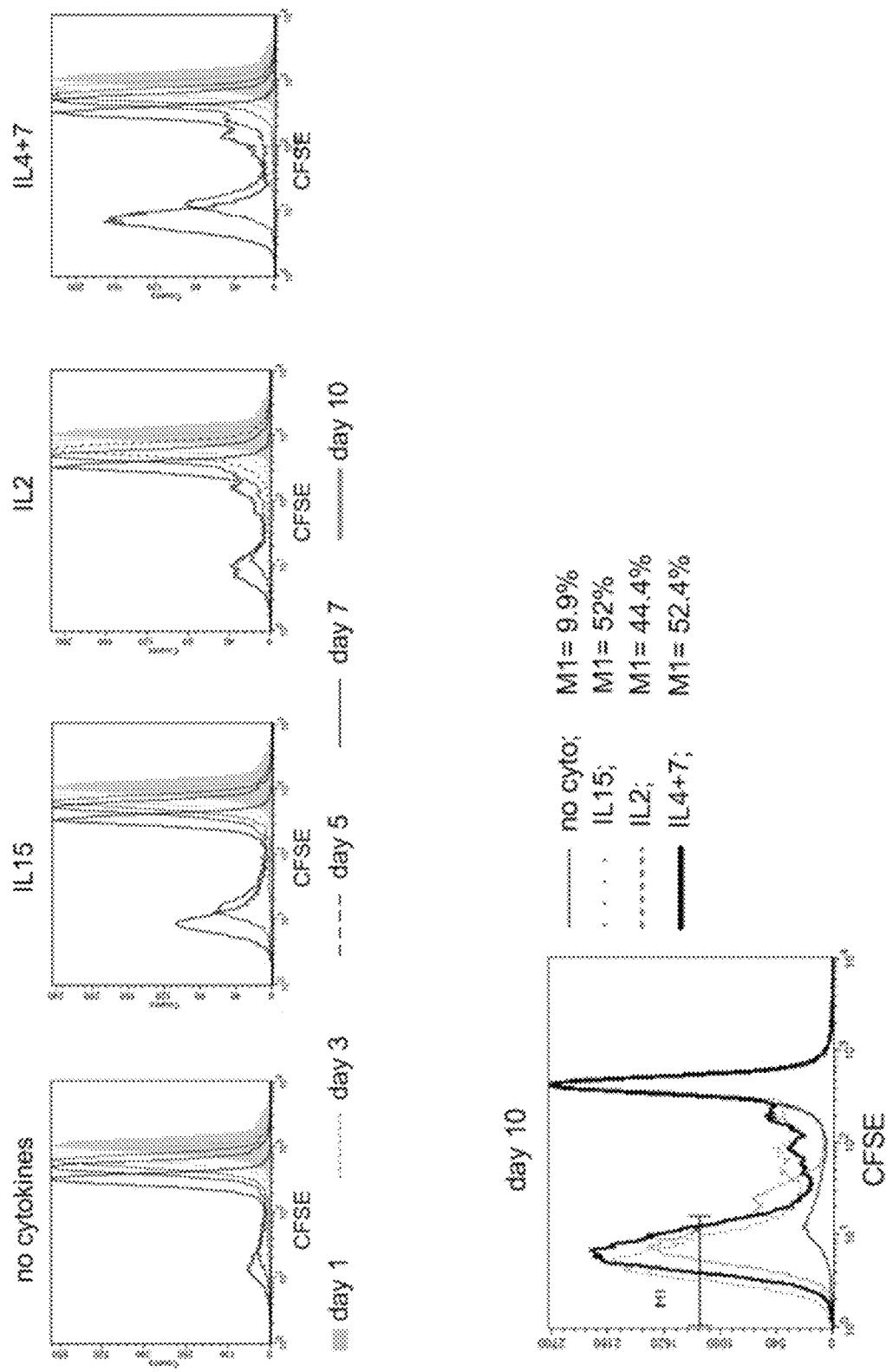

Cultures supplemented with IL15 or IL4+7 showed the greatest overall expansion (5±0.6 and 3.7±0.5 fold increase, respectively) over 9 days (n=5). Cultures that were stimulated in the absence of cytokines did not expand (0.6±0.04), while the IL2 condition was intermediate (2.7±0.1) (FIG. 1A). To determine whether the superior cell numbers were a consequence of improved T cell proliferation, enhanced survival, or the combination, cells were labeled with CFSE on day 0 and then analyzed every 2-3 days to measure cell doubling, while live and apoptotic/necrotic cells were distinguished by Annexin-PI staining (not shown). Flow cytometric analysis demonstrated no difference in the number of cell divisions from day 0-5. However, from day 5 onward cells cultured in cytokines continued to divide, whereas in their absence, cell division was reduced and viability was consistently lower (FIG. 1B). These data indicate that the improved survival of proliferating cells made the primary contribution to the observed increase in cell numbers in cytokine-supplemented cultures.

Example 2

IL4+7 Support the Selective Expansion of Polyclonal, Th1-Polarized T Cells

Figure 1C:
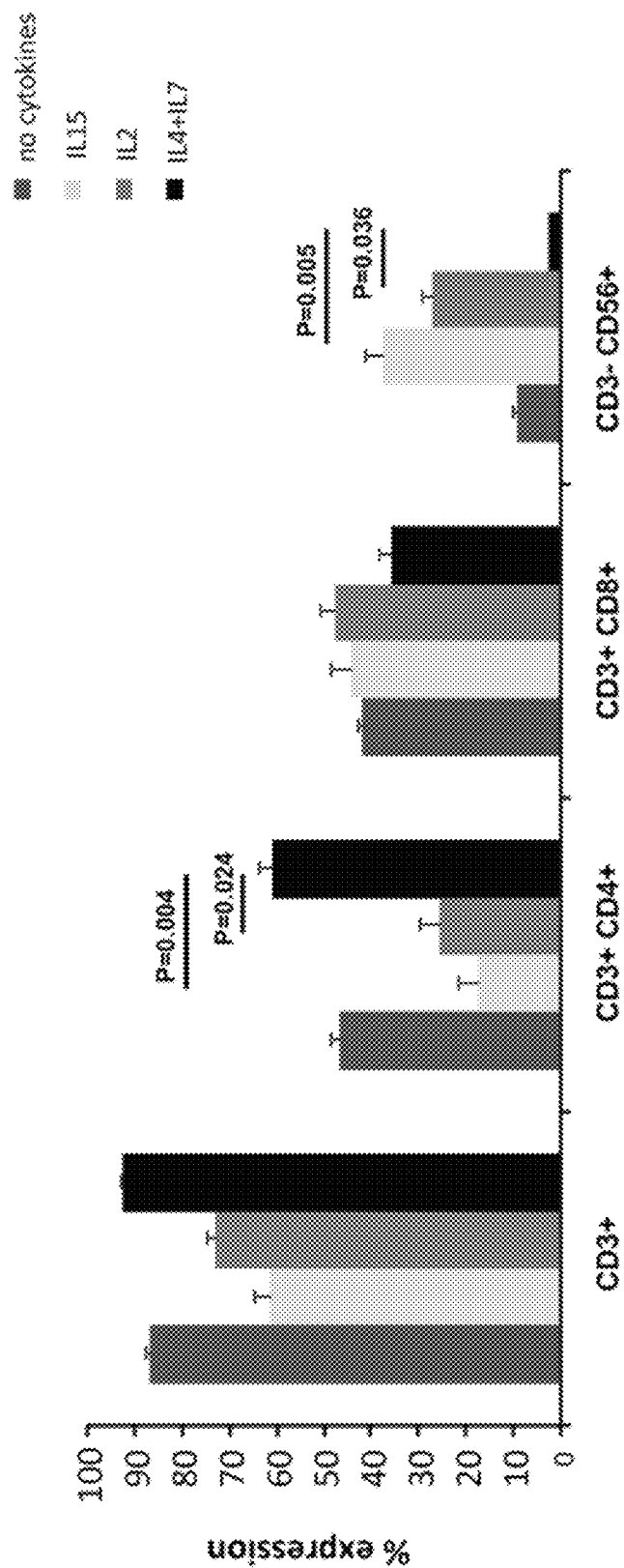
Figure 1D:
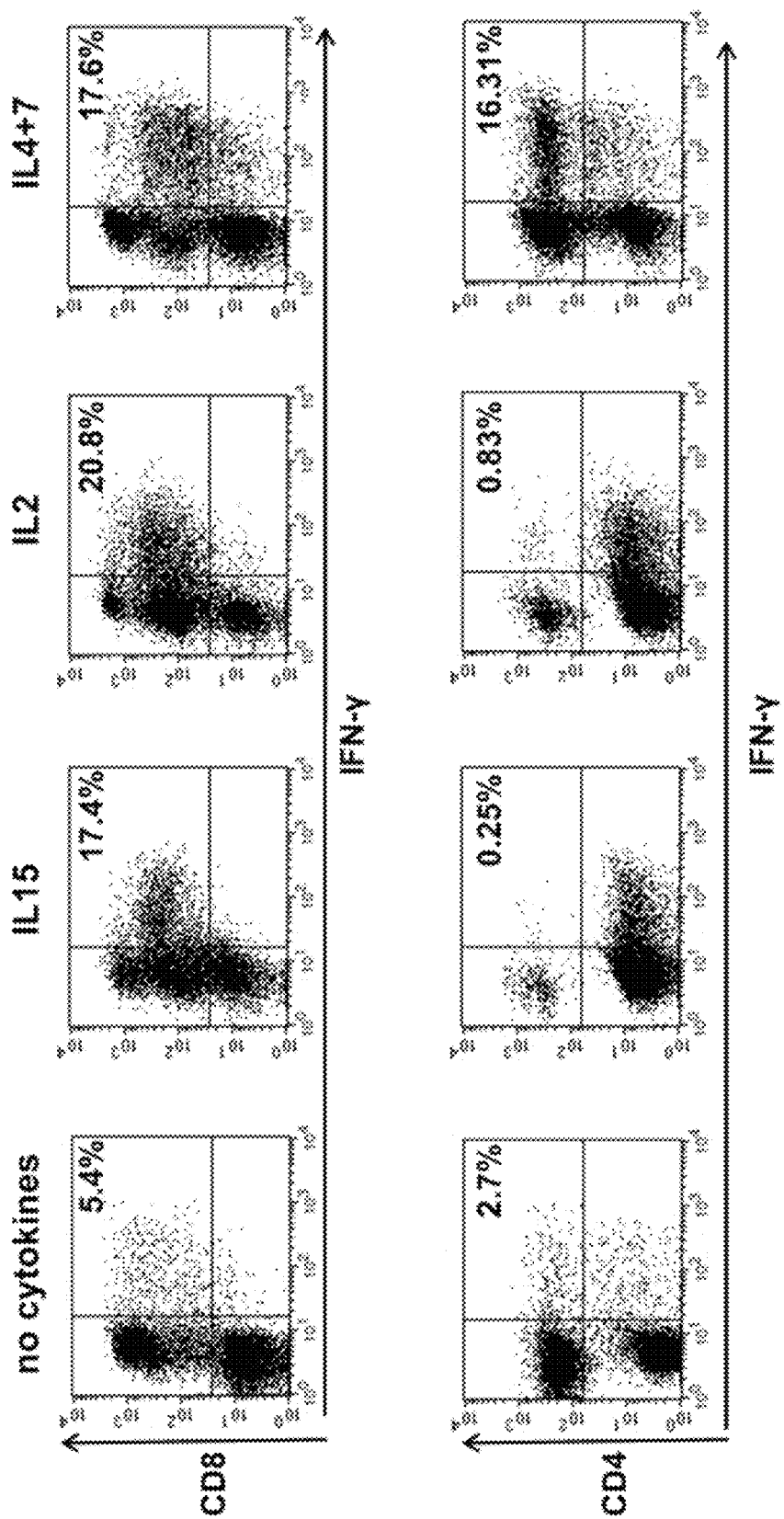
Figure 1E:
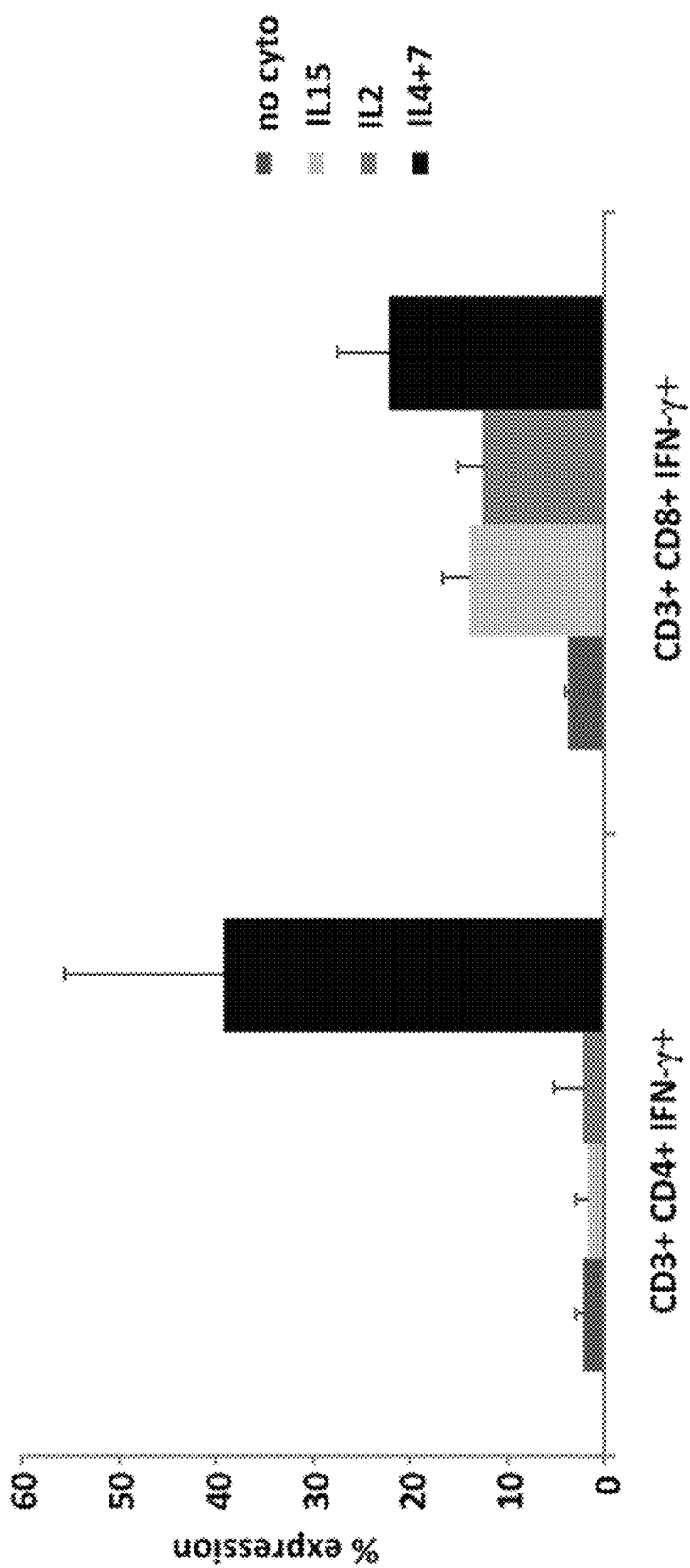
Figure 7:
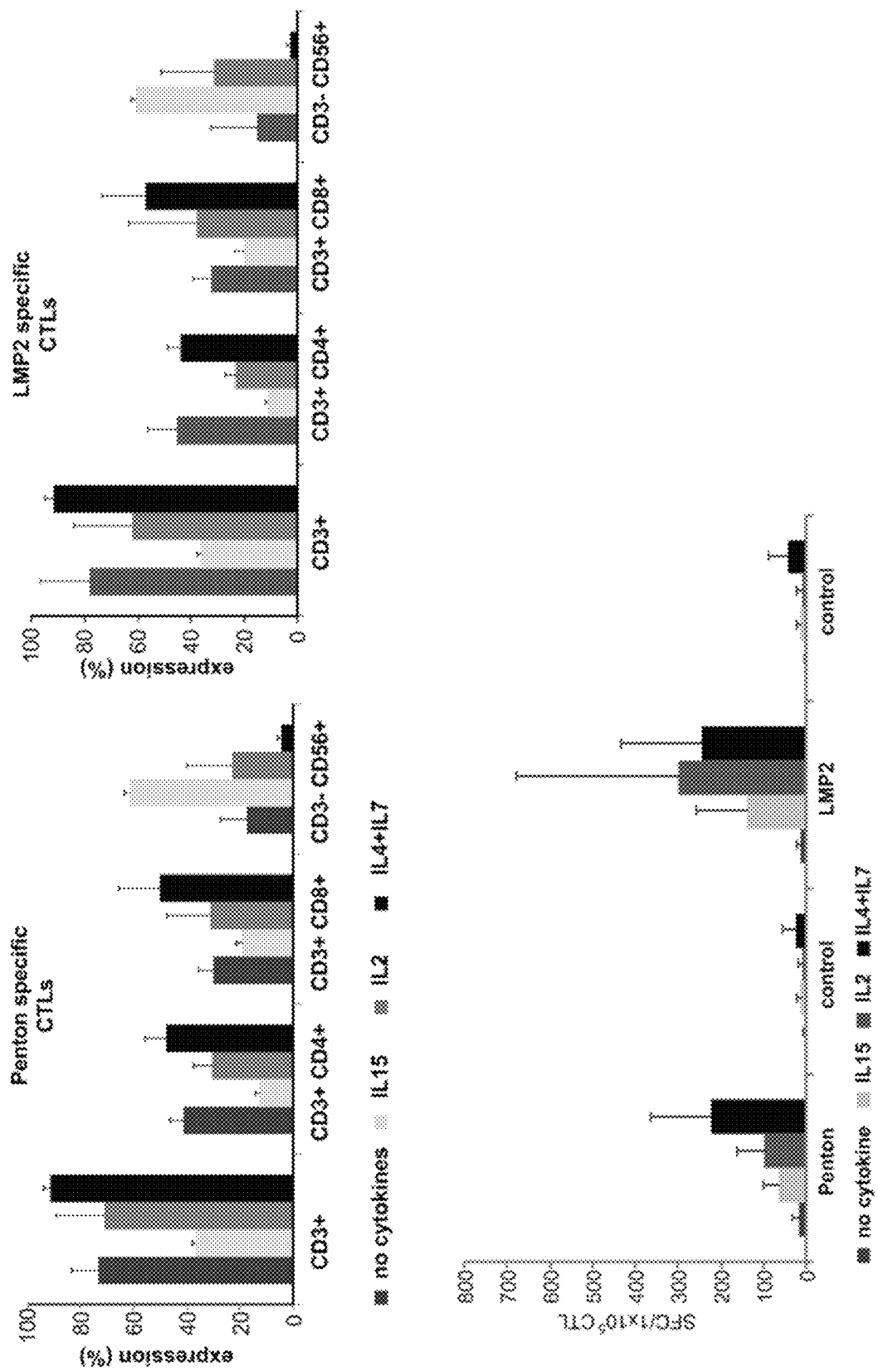
FIG. 7: Phenotype and specificity of Penton and LMP2-specific CTLs generated in the presence of different growth-promoting cytokines. Phenotypic analyses of CTLs on day 9 after initiation with Penton (upper left) or LMP2 (upper right panel) pepmixes and culture in the presence or absence of different cytokines. Results are presented as mean % positive cells+/−STDEV. CTLs of 3 donors were tested for specificity by IFN ELIspot. Results are expressed as SFC/$1 \times 10^5$ input cells+/−STDEV and the control was IFN release in response to stimulation with an irrelevant pepmix.

Optimal in vivo T cell persistence and activity requires both helper (CD4+) and cytotoxic (CD8+) T cells[23]. The inventors therefore used phenotypic analyses to determine that the cells in the cytokine-supplemented cultures reflected the selective expansion of polyclonal T cells. The inventors found the lowest frequency of CD3+ T cells in cultures supplemented with IL2 or IL15 (72.8±2.1% and 61.3±3.7%, respectively), which instead contained significantly higher numbers of CD56+ NK cells than other conditions (27.1±2.3% and 37.7±3.7%, respectively) (n=5). By contrast, IL4+7 cultures were comprised almost entirely of CD3+ T cells (92.6±0.4%), with both CD8+ T cells and significantly more CD4+ T cells (61±2.7%) than the other cytokine-supplemented conditions (IL2 26±4%, IL15 17.6±4.3%, p=0.024, p=0.004, respectively) (FIG. 1C). To confirm that both CD8+ and CD4+ T cells were antigen-specific and produced effector cytokines the inventors performed intracellular cytokine staining (ICS) for IFN. FIG. 1D shows representative results from 1 donor, while FIG. 1E shows summary results for 3 donors. The data confirm that IL4+7-supplemented cultures contained antigen-specific IFN-producing T cells in both compartments (CD4+ 39.3%±16.4%, CD8+ 22.2%±2.2%), at levels substantially higher than in other conditions (no cytokine: CD4+ 2.3%±3.9%, CD8+ 0.8%±0.5%; IL15: CD4+ 1.7%±1.4%, CD8+ 13.9%±2.8% and IL2: CD4+ 2.2%±3.1%, CD8+ 12.6%±2.6%, n=3). Similar results were obtained using pepmixes from subdominant Adv (Penton) and EBV (LMP2) viral antigens; indeed outgrowth of NK cells was even more evident in the IL2 and IL15-supplemented conditions (FIG. 7).

Figure 1F:
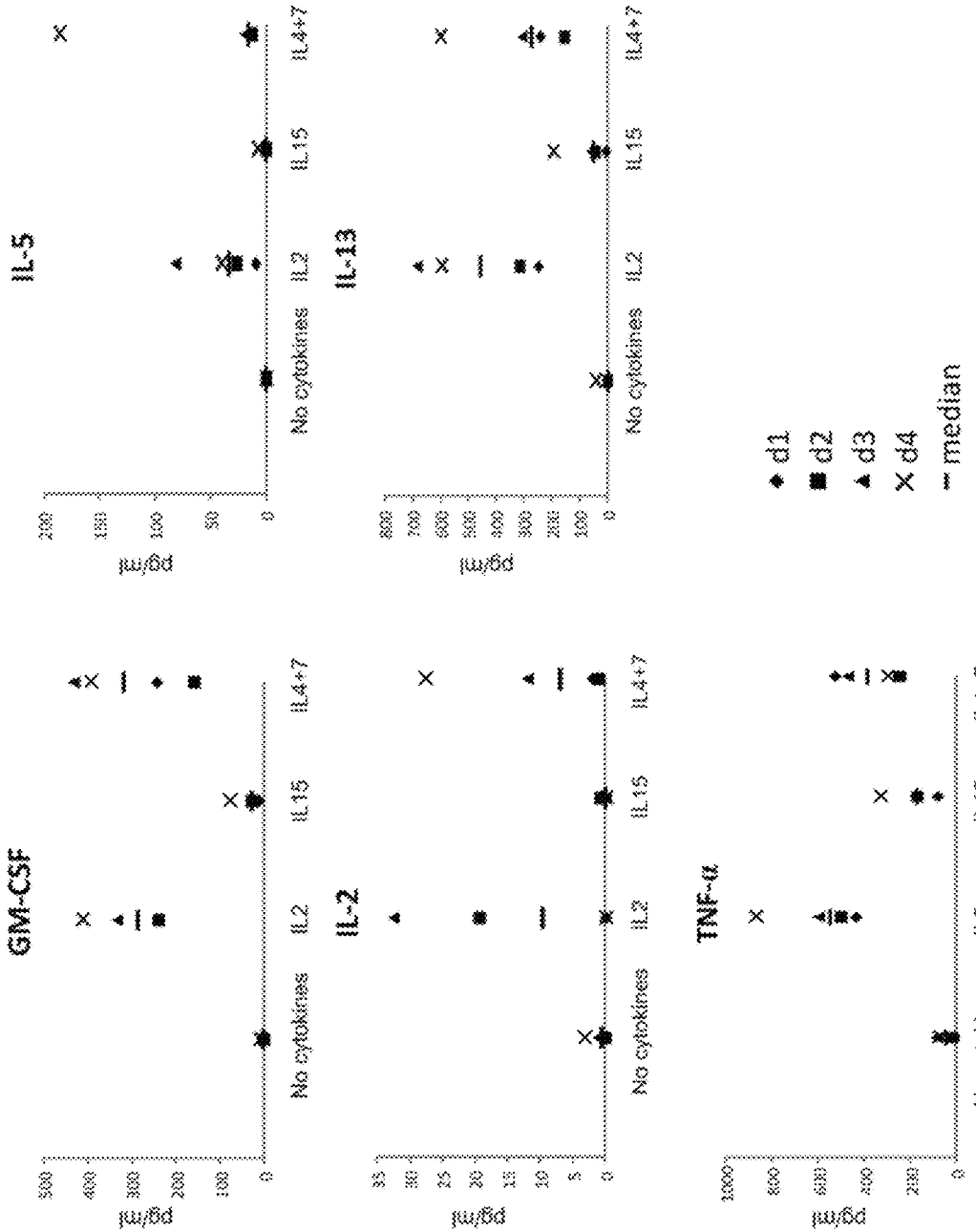
Figure 1G:
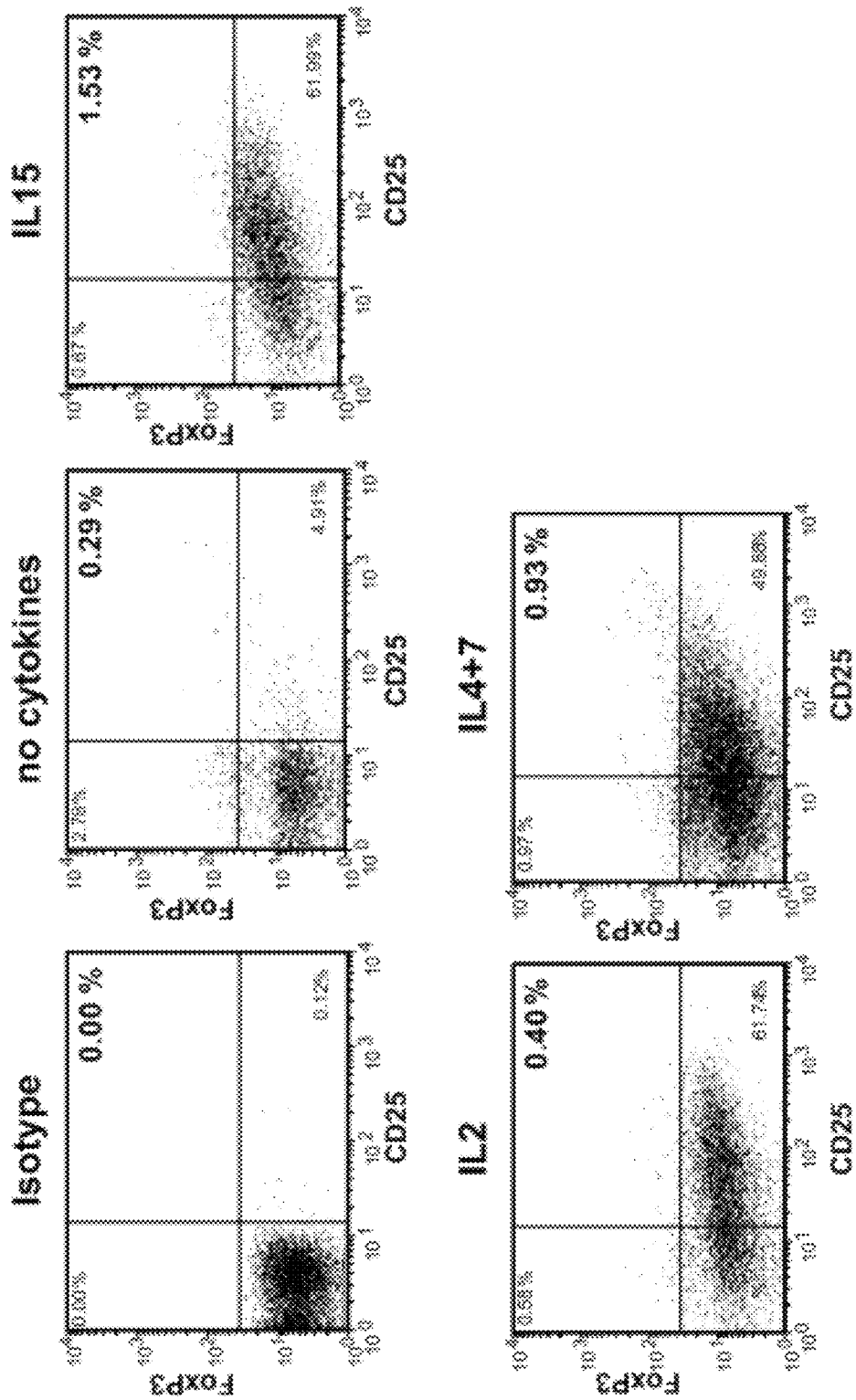
Figure 8:
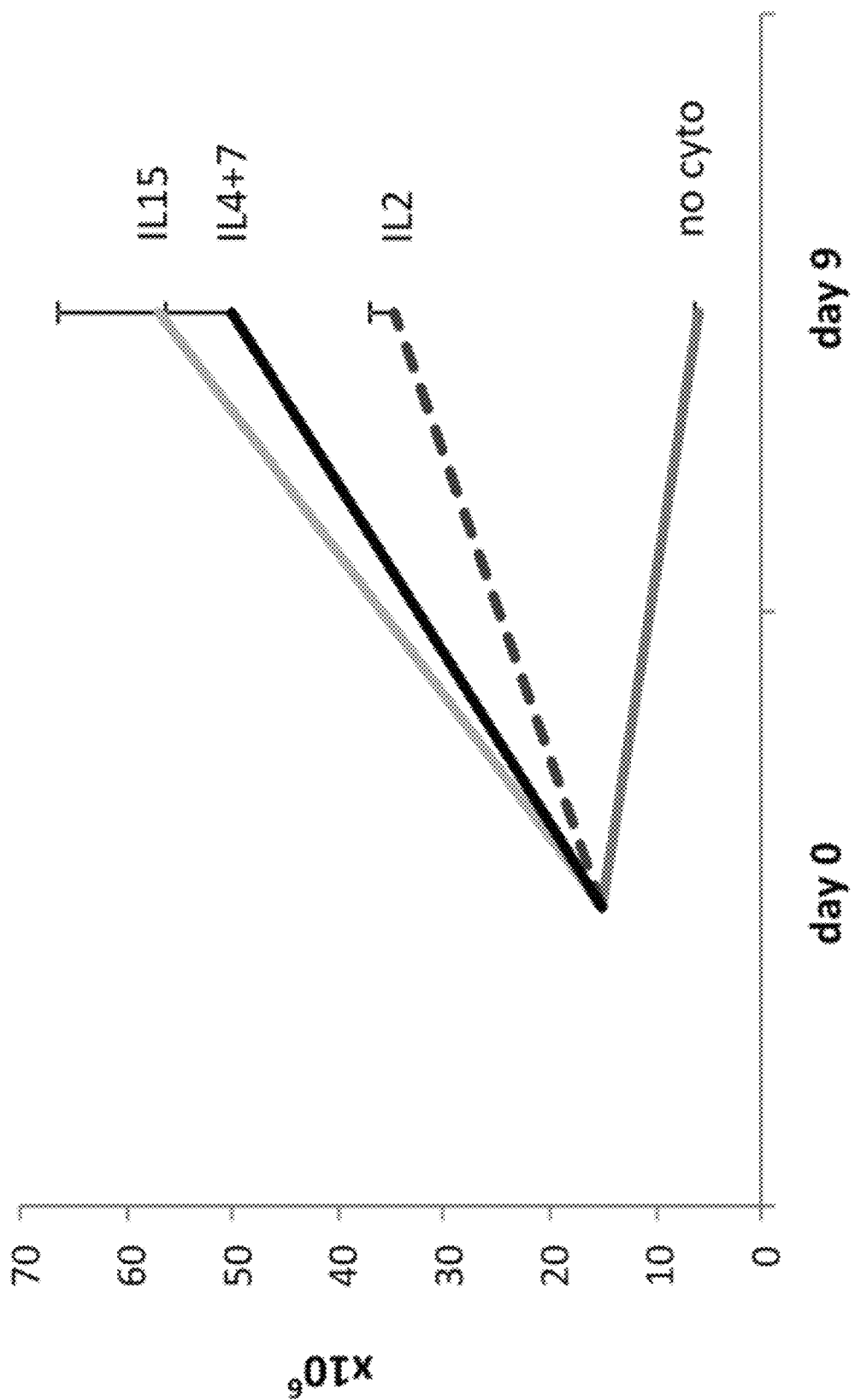
FIG. 8: CD3+ T cell expansion after addition of growth-promoting cytokines. Total T cell numbers were calculated based on total cell numbers evaluated by cell counting using trypan blue exclusion and the percentage of CD3+ T cells detected on day 9 after CTL initiation assessed by flow cytometric analysis. Results from 5 donors are shown (mean cell numbers+/−SEM).

IL4 is a prototypic Th2 cytokine, therefore to more comprehensively evaluate the cytokine profile of the induced CTLs the supernatant of antigen-activated T cells was assessed using luminex array. FIG. 1F shows that, in addition to IFNγ, the IL4+7-supplemented lines produced the prototypic Th1 cytokines GM-CSF, IL-2 and TNFα, at levels similar to that of IL2-induced CTLs. In addition, levels of Th2 cytokines (IL5 and IL13) were not substantially different and there was no evidence of regulatory T cell outgrowth, as assessed by CD4/CD25/FoxP3+ staining (FIG. 1G). Thus, IL4, in combination with IL7, induces selective expansion of polyclonal, Th1-polarized T cells that produce multiple effector cytokines upon stimulation (FIG. 8).

Example 3

Figure 2A:
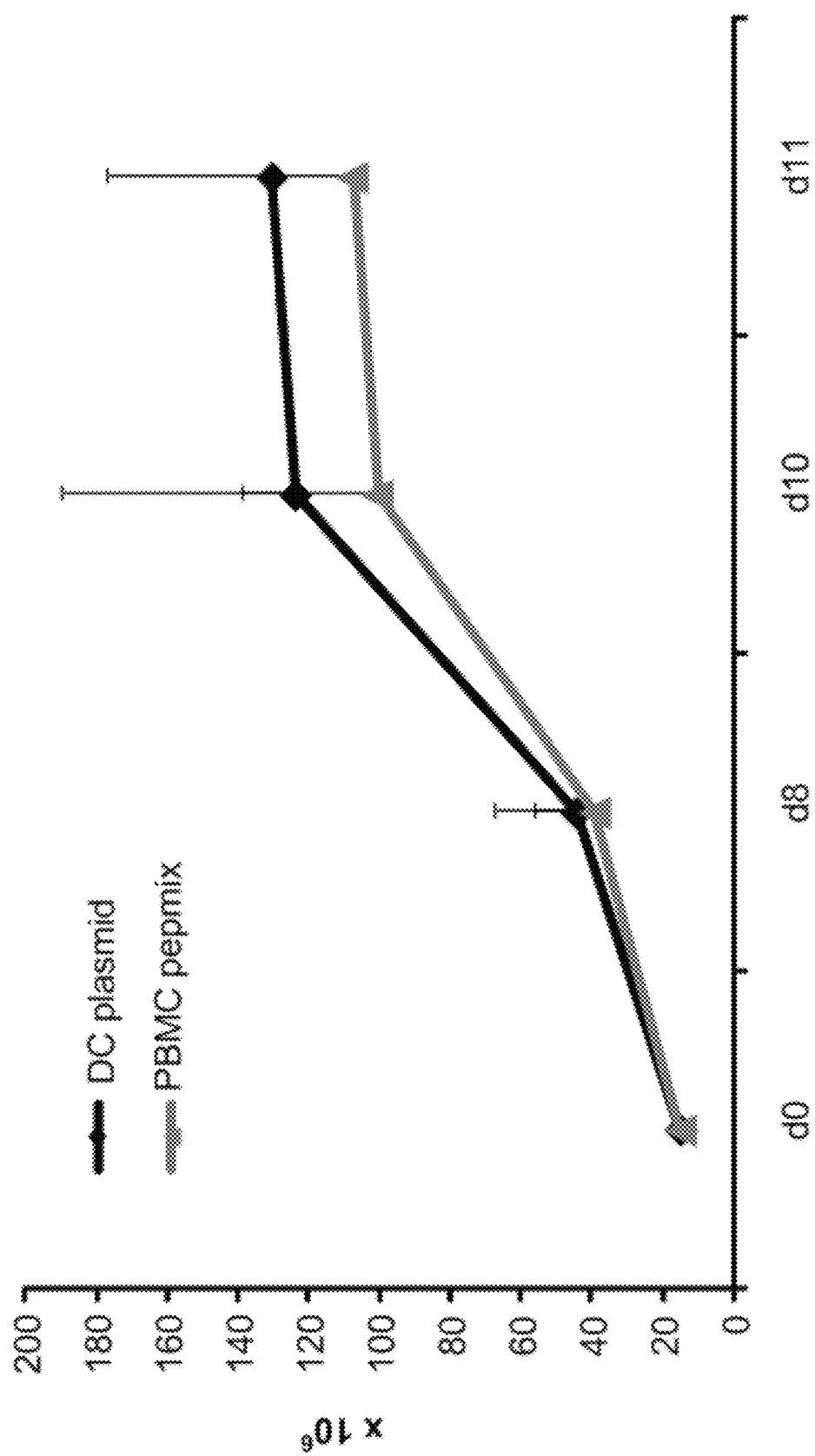
FIGS. 2A-2D: Peptide-stimulated and plasmid-activated CTLs share similar phenotypic and functional characteristics.
Figure 2B:
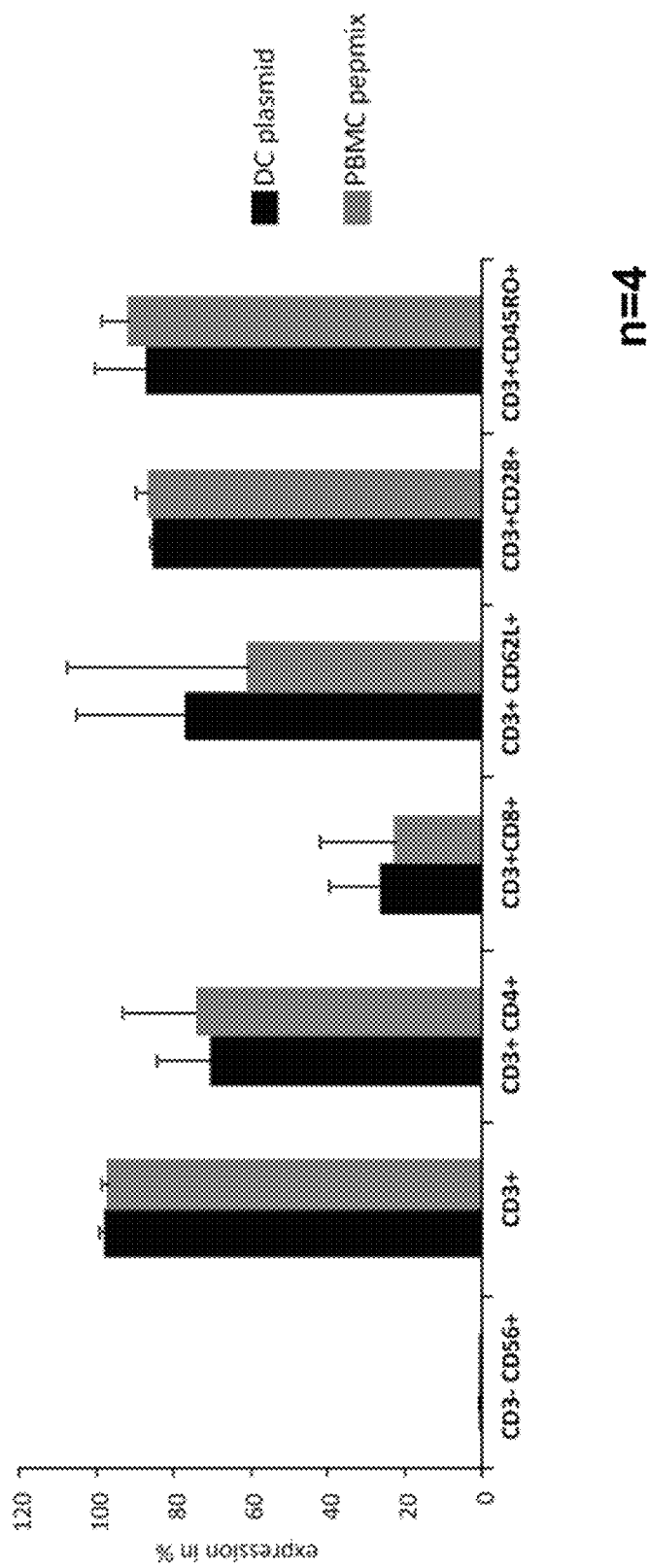
Figure 2C:
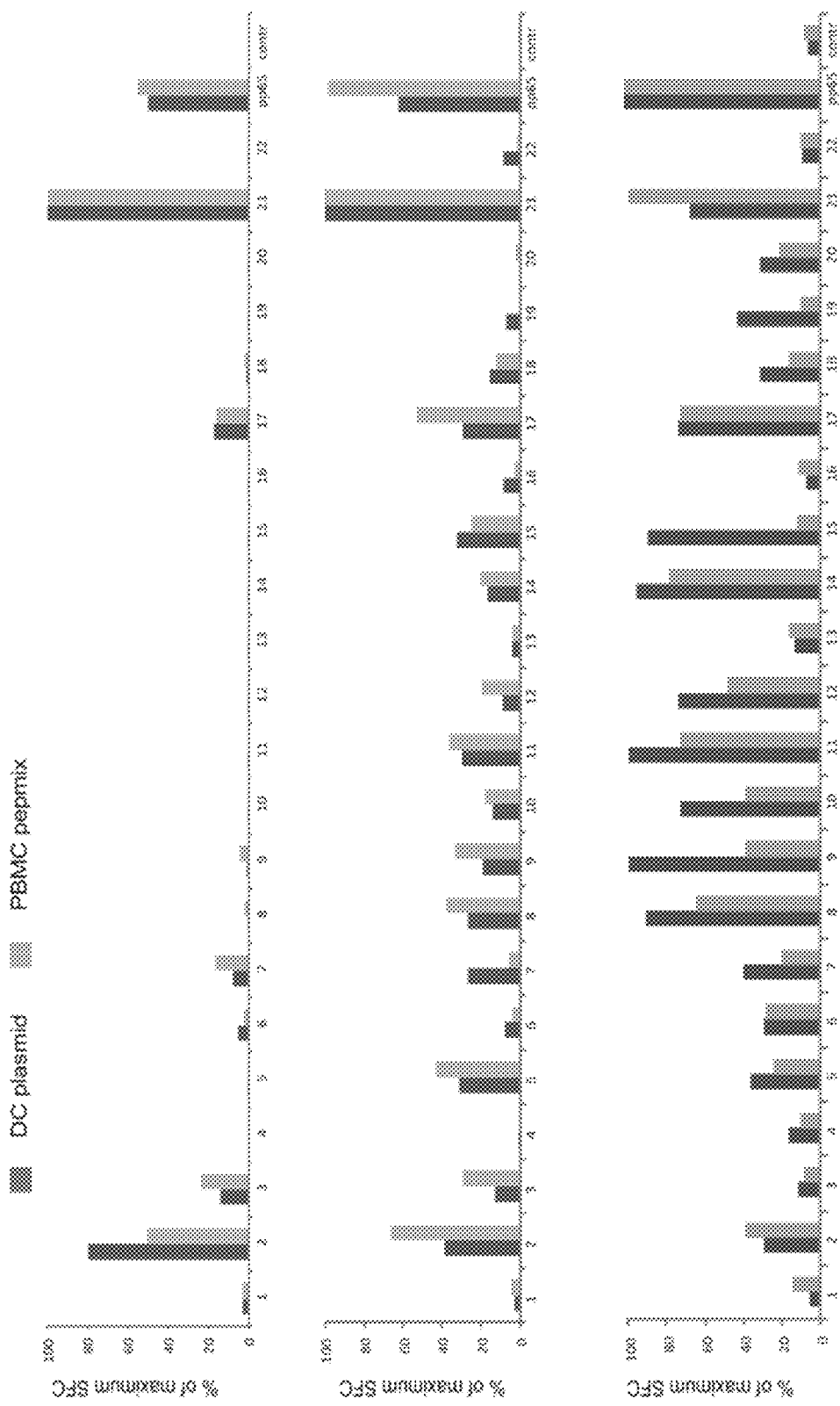
Figure 2D:
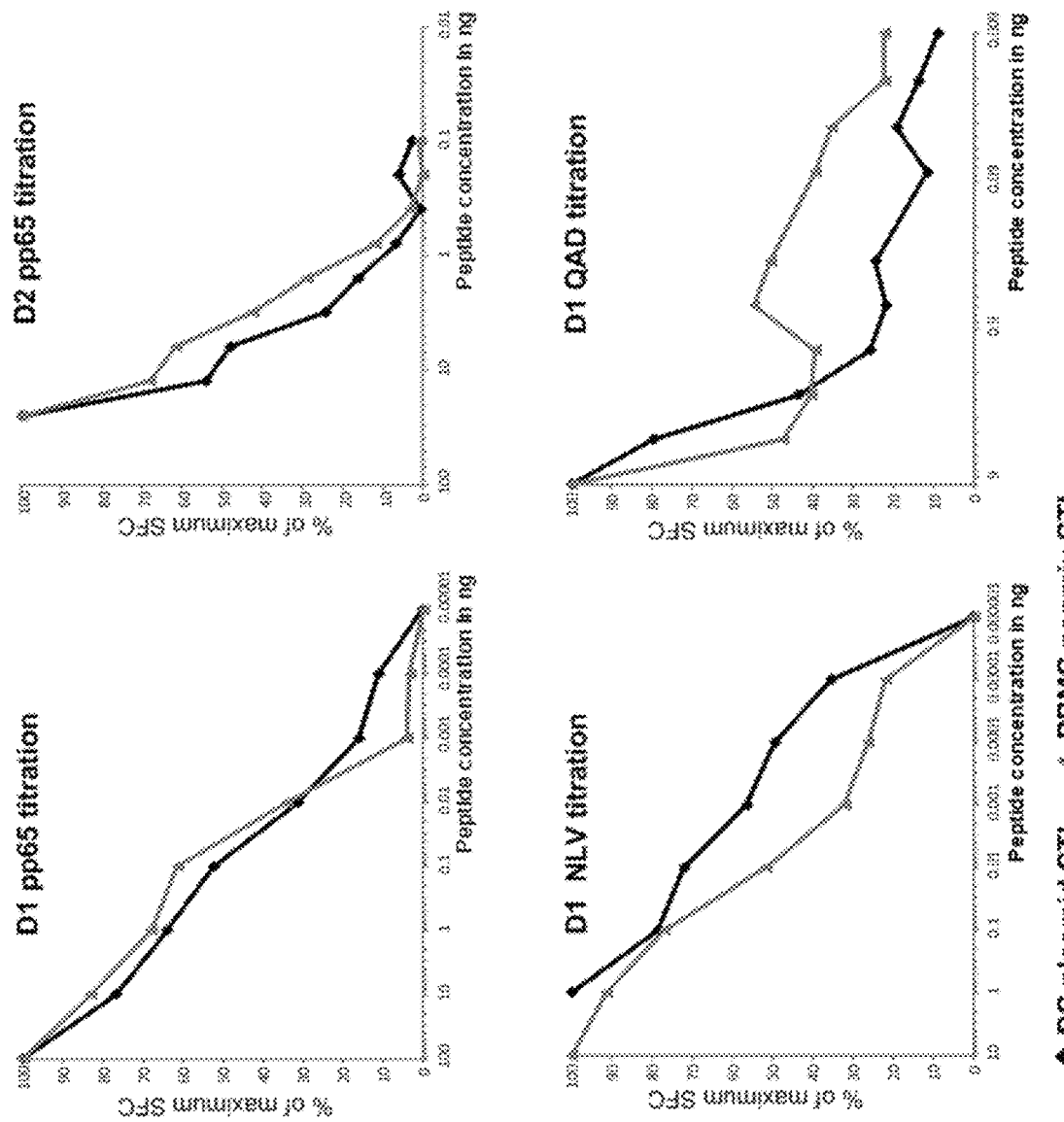
Figure 9:
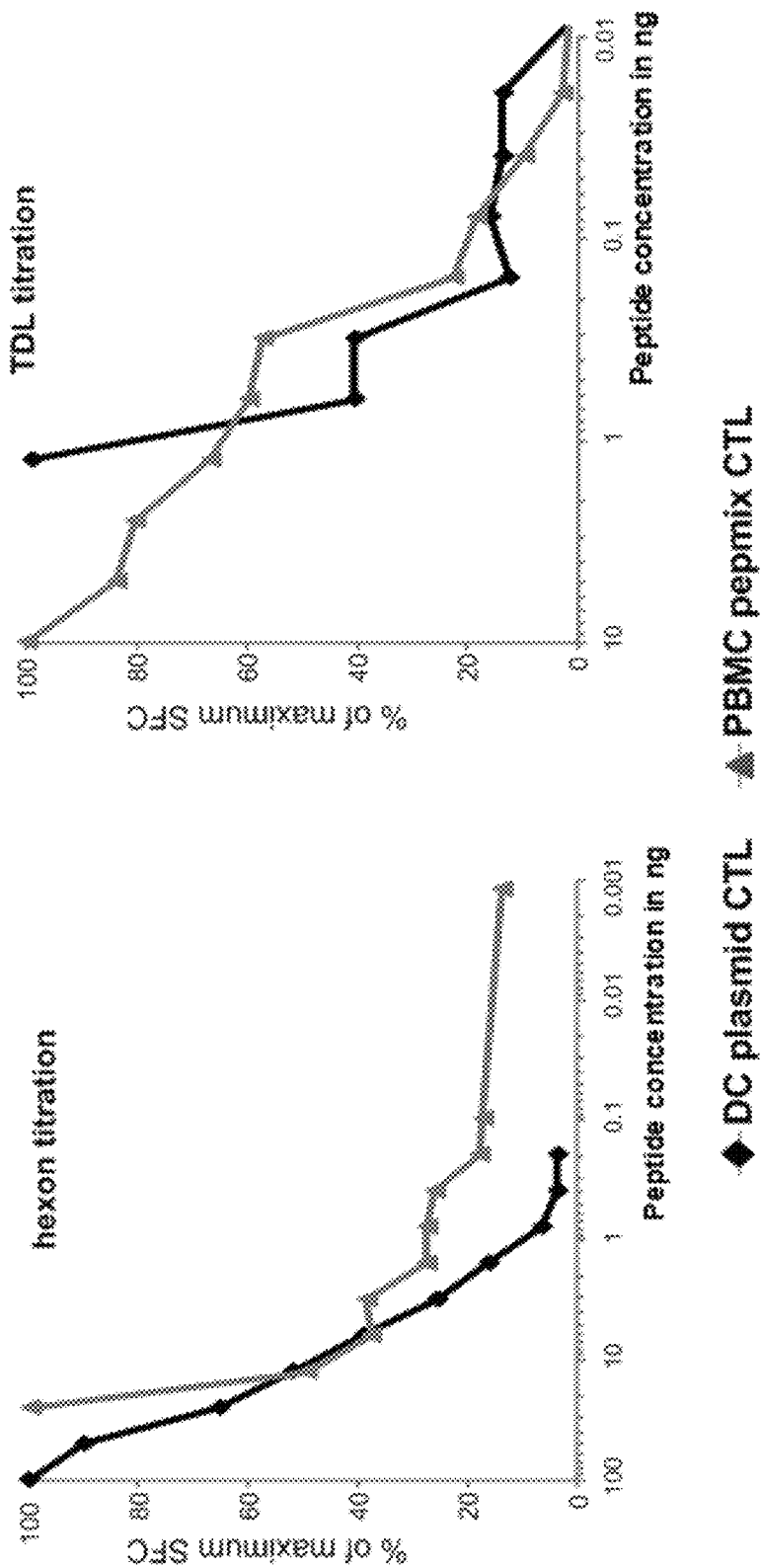
FIG. 9: TCR avidity is comparable in Hexon DC plasmid-activated and pepmix-stimulated PBMCs. TCR avidity of Hexon-specific CTLs stimulated with plasmid nucleofected DCs or pepmix stimulated PBMCs was tested by serial dilution of Hexon pepmix or HLA-A1 restricted peptide TDL with IFN ELIspot as readout. Results are plotted as % of maximum SFC.

Overlapping 15 Mer Peptide Libraries Activate T Cells with Similar Specificity and Avidity to Those Generated Using Endogenously-Processed Full Length Antigen To address concerns that pepmixes might reactivate low avidity T cells unable to recognize antigens that are naturally processed and presented by virus-infected cells, the inventors compared pp65 pepmix-activated CTLs with those generated using DCs nucleofected with a DNA plasmid encoding the same antigen[20, 21]. After activation, each set of cells was expanded in IL4+7. Expansion was similar between the groups, with 107±23.4×10$^6$ cells generated using pepmix-pulsed PBMCs (7.2 fold expansion) versus 130.3±46.9×10$^6$ cells in the DC-stimulated cultures (8.7 fold expansion) (FIG. 2A) (n=3). Phenotypic analysis demonstrated that the pepmix-activated CTLs were predominantly CD4+(74.3±19.3%), with a minor CD8+ component (22.8±19.2%), as were the plasmid-activated CTLs (CD4+ 70.6±14.2% and CD8+ 26.5±13.4%) and both expressed similar levels of the memory and activation markers CD62L, CD28 and CD45RO (61±46.7%, 86.5±3.5%, 92±7.1% pepmix vs. 77±28.3%, 85.5±0.7%, 87.5±13.4% plasmid) (FIG. 2B). The inventors next compared the breadth of epitopes recognized by measuring responses to 110 20mer peptides (overlapping by 15aa) spanning CMV-pp65 and arranged into 22 pools such that each peptide was represented in 2 pools[24]. FIG. 2C shows that both the recognition of a given peptide and the magnitude of the response thereto was little changed by the antigen source. Finally, the inventors compared functional avidity by IFNγ ELIspot using log dilutions of the pp65 pepmix or epitope peptides (A2-NLV and A24-QAD) as a stimulus. As shown in FIG. 2D, there was no significant difference in the avidity of the CTLs. This data was confirmed for other viral antigens using Adv-Hexon pepmix and viral antigen-encoding plasmid as a stimulus (FIG. 9).

Example 4

Figure 3A:
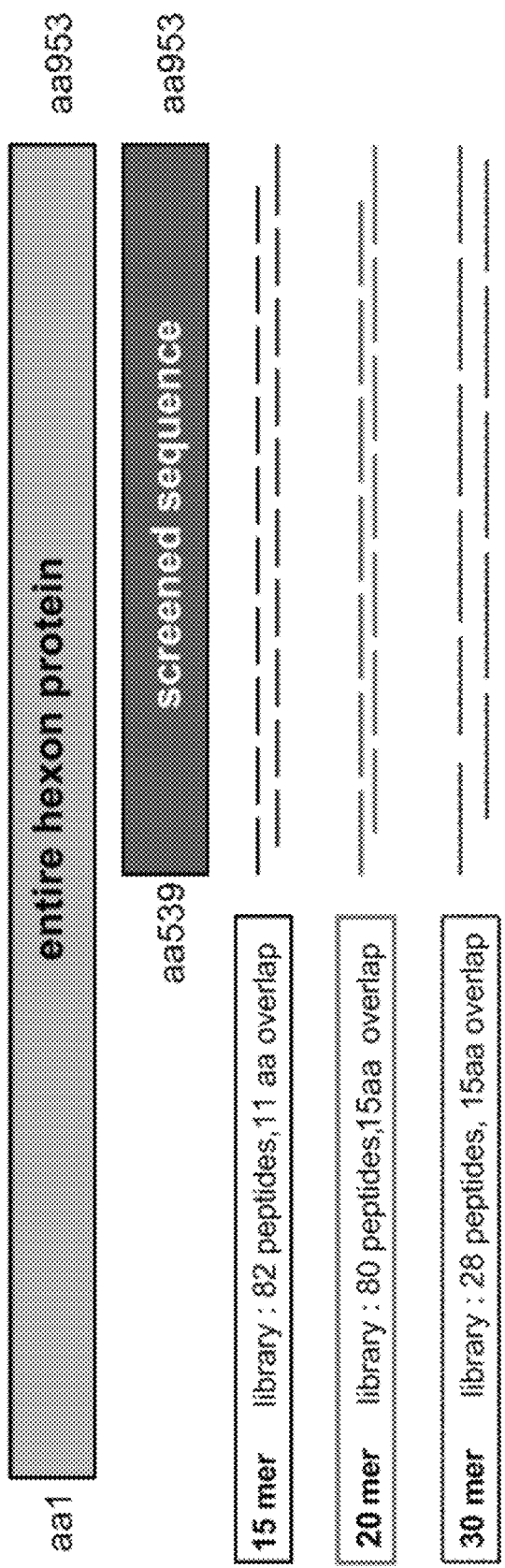
FIGS. 3A-3C: Peptide length does not affect breadth of reactivity.
Figure 3B:
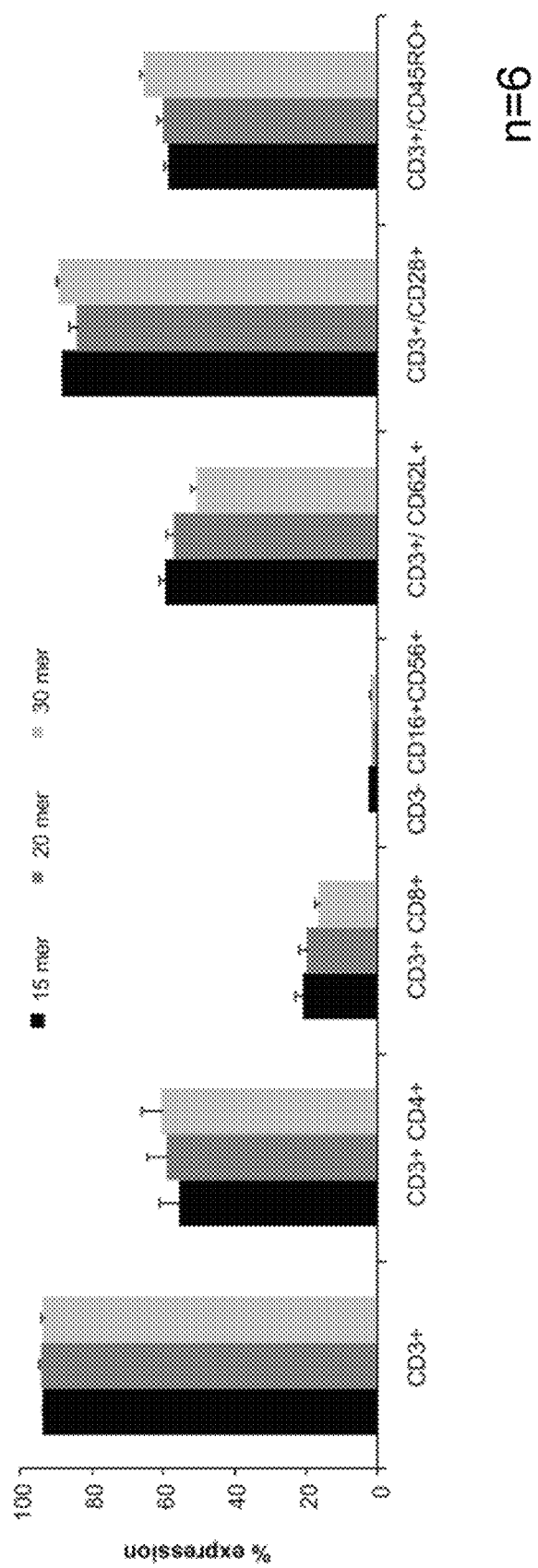

15 Mer Peptides Activate CD4+ and CD8+ T Cells as Efficiently as Long (20 Mer or 30 Mer) Peptides Since CD4+ epitopes (>20aa) may be longer that CD8 epitopes (8-10aa) the inventors next determined whether longer peptides would induce higher frequencies of antigen-specific CD4+ T cells. The inventors obtained three overlapping peptide libraries (#1-15mers overlapping by 11, #2-20mers overlapping by 15, and #3-30mers overlapping by 15) spanning the C terminus (aa539-953) of Adv-Hexon; a region rich in both CD4+ and CD8+ epitopes[25, 26] (FIG. 3A). The inventors directly stimulated PBMCs with each of the libraries and evaluated the phenotype, epitope specificity and breadth of the lines.

Figure 3C:
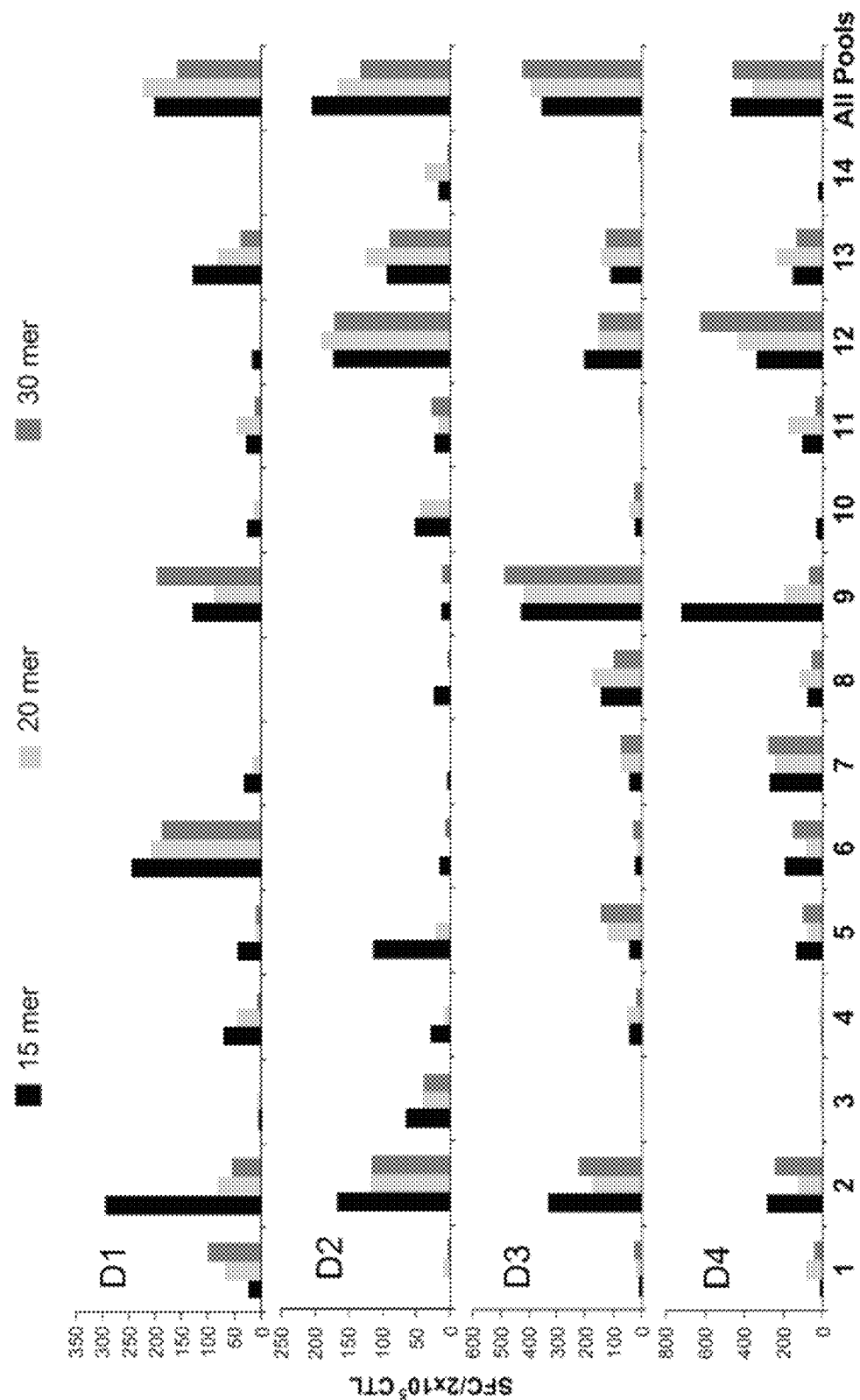

Phenotypically the lines were comparable, with a predominance of CD4+ cells (mean 56±5.5% vs. 59±5.8% vs. 60±6%) and a minor CD8+ component (mean 21±0.2% vs. 20±0.1% vs. 16±0.2%), and similar levels of the memory and activation markers CD62L, CD28 and CD45RO (CD62L—60±1.9% vs. 57±1.9% vs. 51+/−1.6%, CD28—88±0.6% vs. 84±2.1%, vs. 89±0.6% and CD45RO—58±1.7% vs. 60±1.6% vs. 60±1.2%) (15mer vs. 20mer vs. 30mer) (n=6). To learn whether the spectrum of epitopes recognized differed based on the stimulating library; the inventors rechallenged the induced CTLs with subpools of peptides from each library and found no consistent or statistically significant differences in the breadth of peptides recognized. Results for the 15mer minipool rechallenge are shown in FIG. 3C. Since 15mer pepmixes are readily available as both research and clinical products the inventors performed all subsequent experiments with this antigen source.

Example 5

Figure 4:
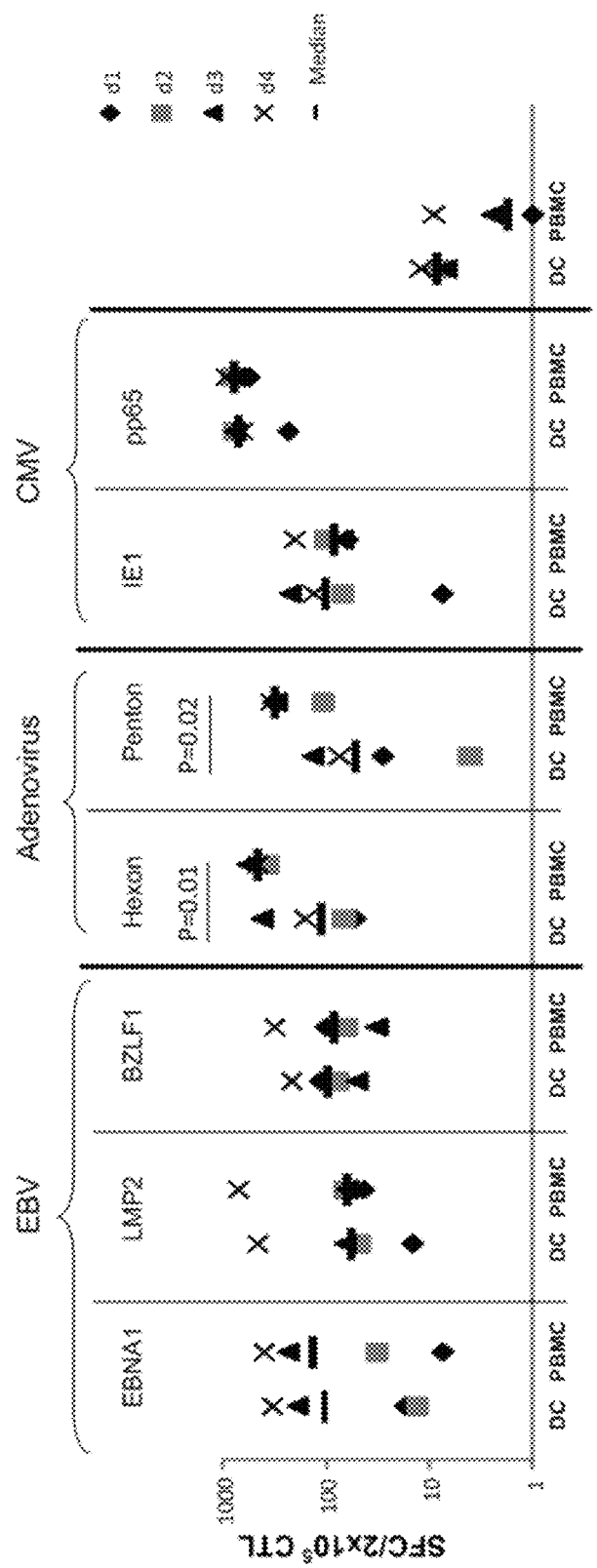
FIG. 4: Pepmix-activated trivirus-specific CTL lines show similar specificity to plasmid-activated T cells. CTL lines were generated using DCs nucleofected with DNA plasmids encoding EBNA-1, LMP2, BZLF-1 (EBV), Hexon, Penton (Adenovirus), IE-1 and pp65 (CMV) or direct PBMC stimulation with the corresponding pepmixes. Specificity was determined 10 days after initiation with IFN ELIspot as readout. Results are expressed as SFC/$1 \times 10^5$ input cells. Control was IFN release in response to stimulation with irrelevant pepmix.

Generation of a Single T Cell Culture with Simultaneous Specificity for Adv, EBV and CMV After successfully generating CTLs using peptides derived from a single viral antigen and culture in IL4+7, the inventors next prepared a single culture of CTLs simultaneously recognizing CMV, EBV, and Adv. For each virus the inventors targeted immunogenic antigens; CMV-IE1 and pp65, Adv-Hexon and Penton, and EBV-EBNA1, LMP2 and BZLF1[8, 9, 17, 18, 27-31] and pulsed PBMCs with the relevant pepmixes before culture in IL4+7. After 9-12 days the inventors compared the antiviral reactivity of the resulting CTLs with those generated using our current clinical trivirus CTL protocol which uses DCs nucleofected with plasmids encoding the same antigens as a stimulus[20, 21] (FIG. 4). IFNγ ELIspot confirmed that pepmix-generated CTLs from 4 donors had antiviral activity against all three viruses and seven stimulating antigens. The frequency of T cells reactive against EBV (EBNA1, LMP2, BZLF1) and CMV (IE1, pp65) was comparable irrespective of the stimulus. In contrast, all 4 donors had significantly more Adv-reactive T cells (Hexon and Penton) in pepmix-stimulated cultures [Hexon—median 462.3, range 373-572.5 vs. median 112, range 53-421.5 SFC/2×105 CTL; p=0.01, Penton—median 317, range 105.5-345 vs. median 51.25, range 4-134 SFC/2×105 CTL, p=0.02, pepmix vs. plasmid, respectively].

Example 6

Extension to Additional Viruses

To determine whether the direct pepmix stimulation approach could be extended to generate multivirus-specific CTL lines targeting a broader spectrum of different clinically relevant viruses the inventors stimulated PBMCs with pepmixes spanning 2 or 3 T cell immunogenic antigens from CMV, Adv, EBV, BK, Influenza, RSV and HHV6 (Table 1).

TABLE 1

| Exemplary Antigens from Exemplary Viruses | |
|---|---|
| Virus | Antigen |
| EBV | EBNA-1, LMP2, BZLF1 |
| CMV | IE-1, pp65 |
| Adenovirus | Hexon, Penton |
| BK virus | LT, VP-1 |
| Influenza | MP1, NP1 |
| RSV | N, F |
| HHV-6 | U14, U90 |

Figure 5B:
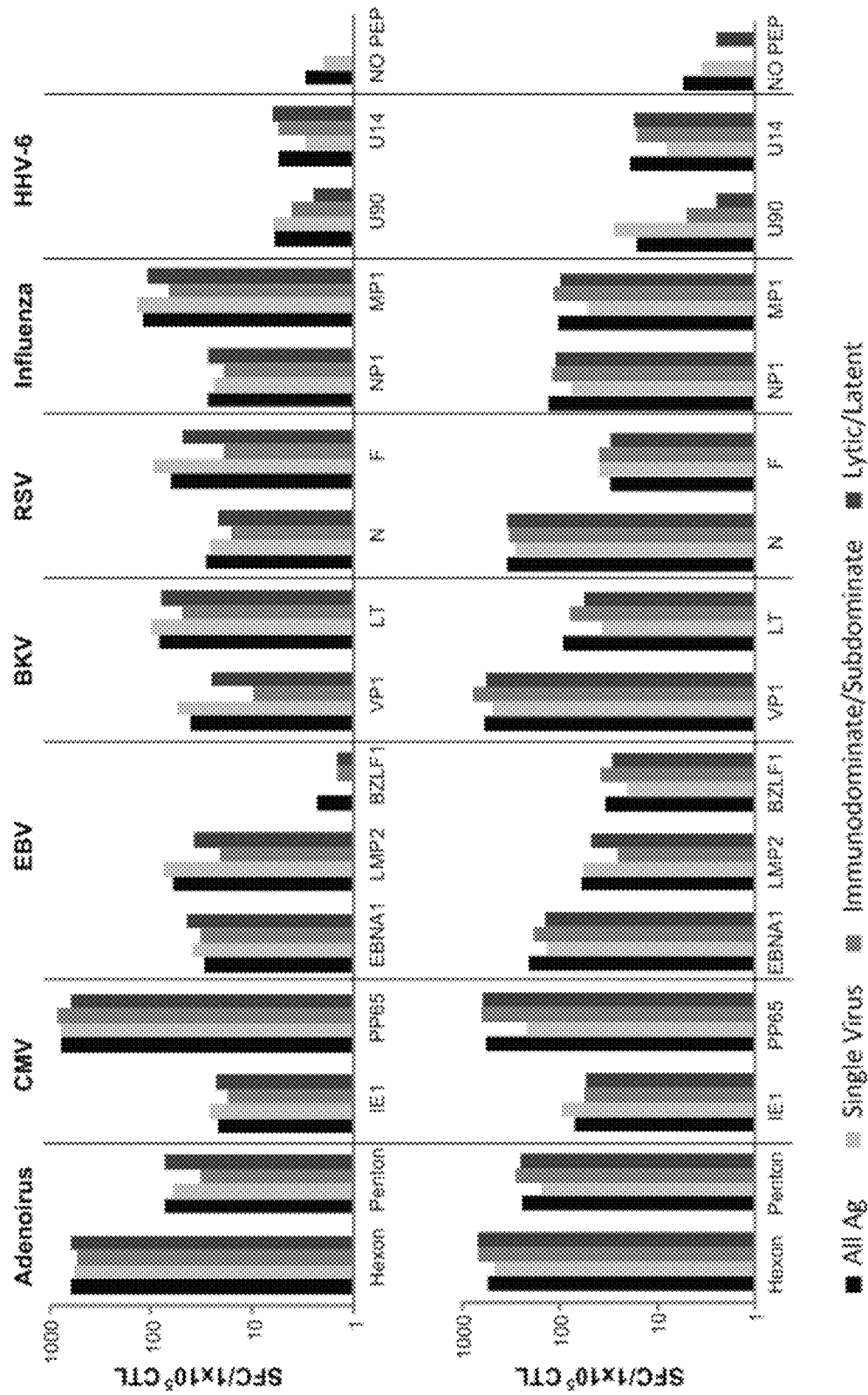
Figure 5C:
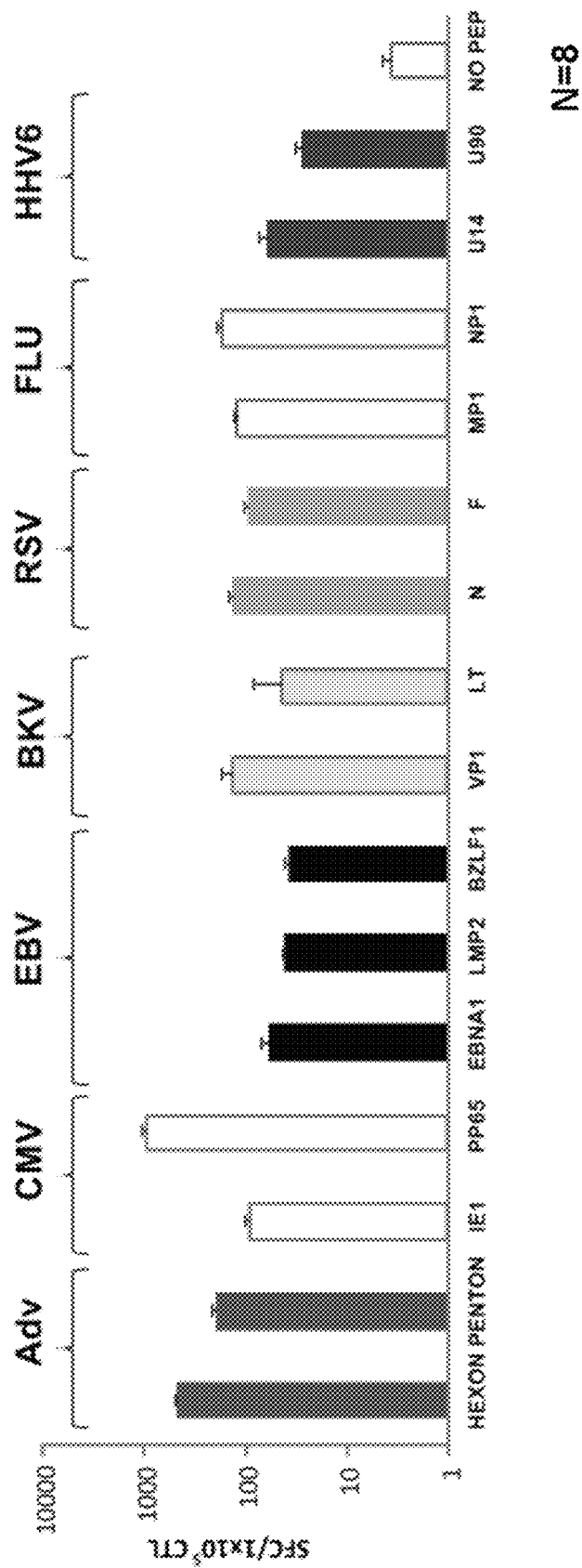
Figure 5D:
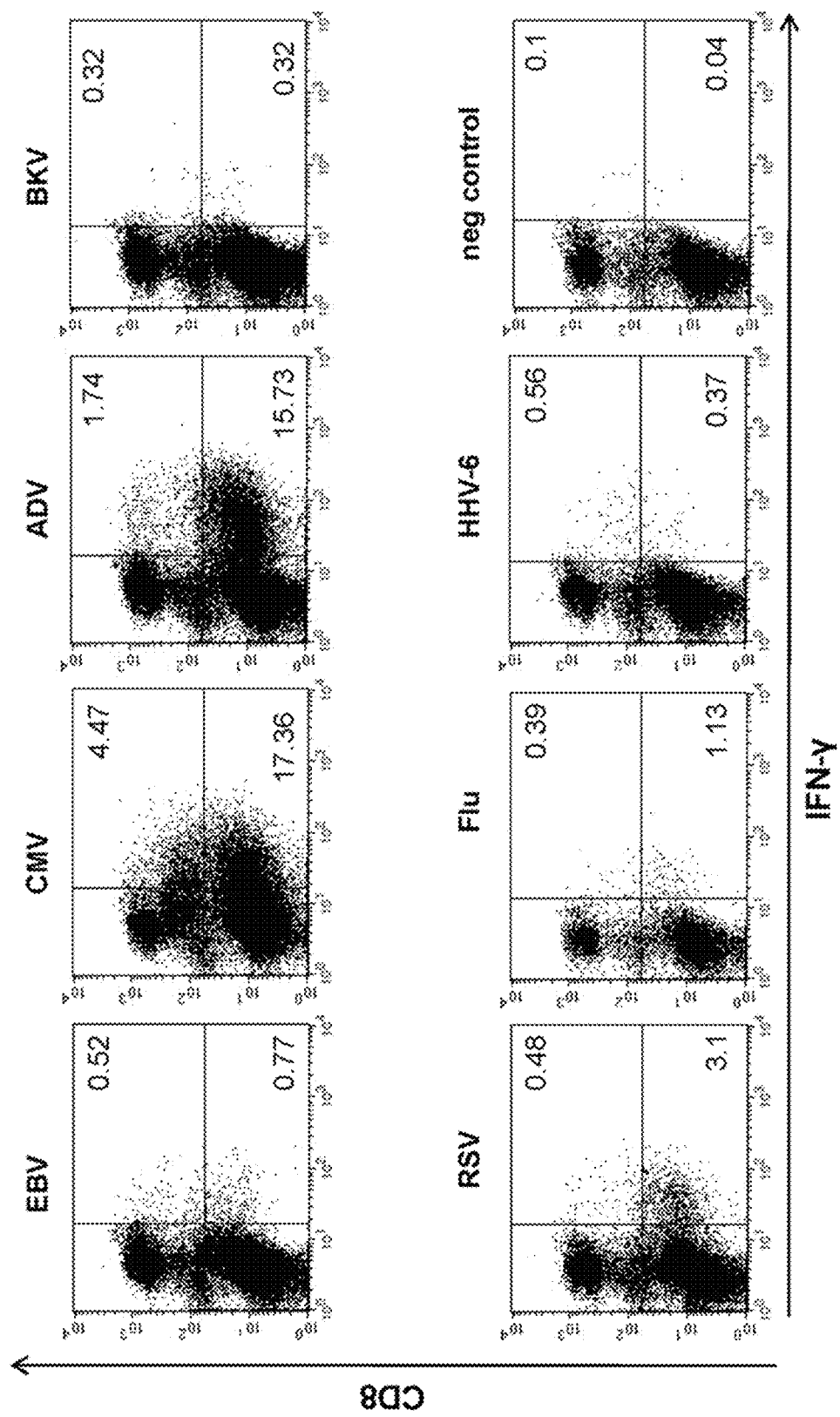
Figure 5E:
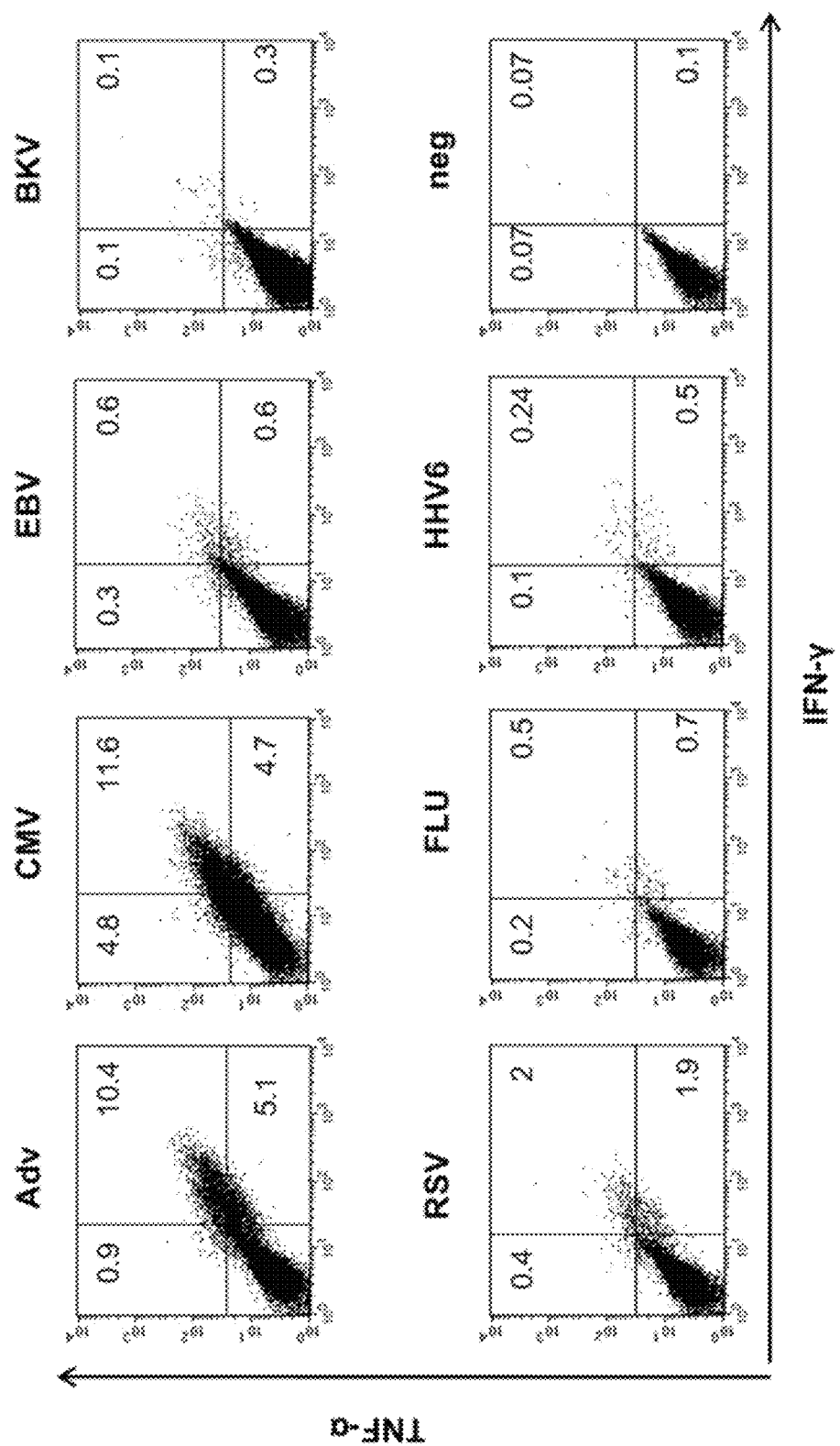
Figure 10:
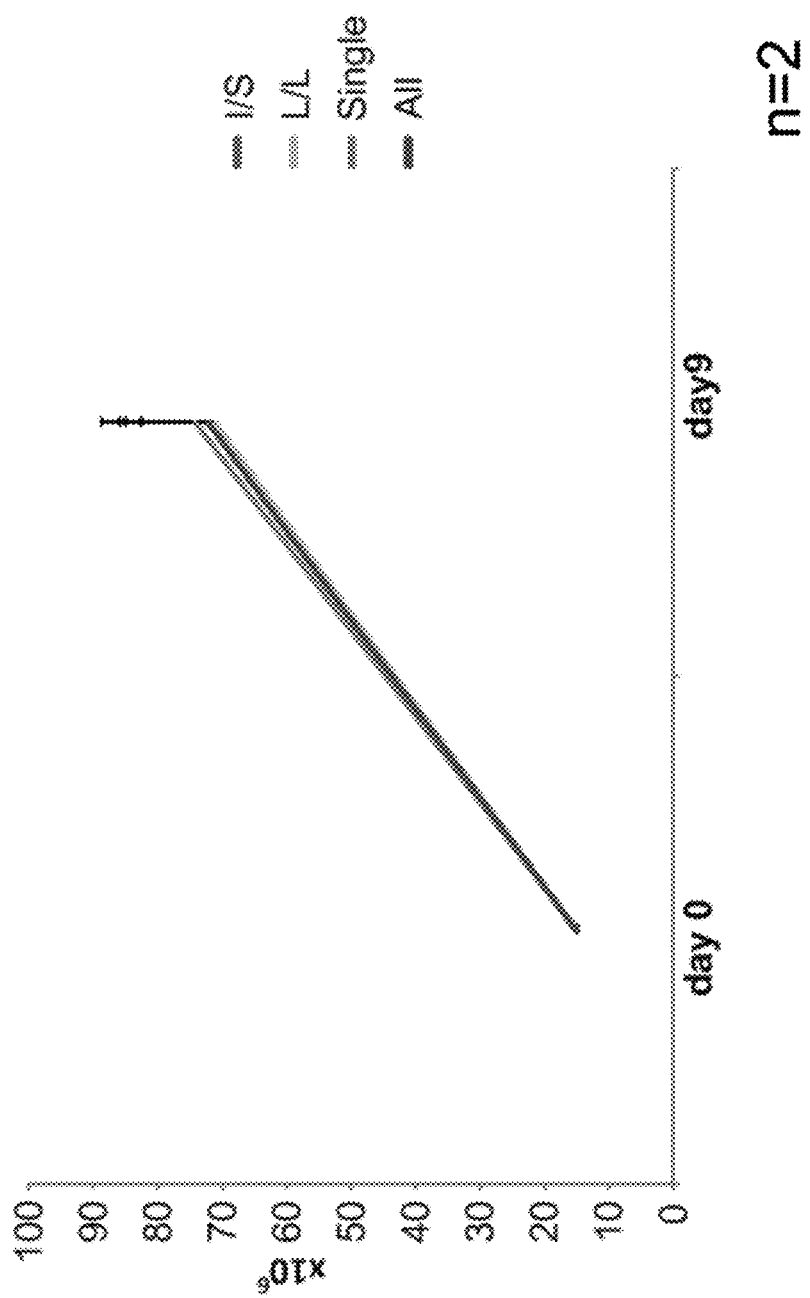
FIG. 10: Comparable expansion of CTLs stimulated with pooled vs. single pepmixes. Cell expansion of CTL generated from 2 donors was evaluated using trypan blue exclusion 9 days after PBMC stimulation. Results are expressed as mean cell numbers+/−STDEV.

To determine whether antigenic competition would preclude pooling the inventors segregated the pepmixes and stimulated PBMCs with minipools containing pepmixes from, A) each virus; B) immunodominant (CMV, RSV, Flu, HHV6) and sub-dominant (Adv, EBV, BK) viruses; C) lytic (Adv, RSV, Flu) and latent (EBV, CMV, HHV6, BK) viruses, or D) a mastermix of all pepmixes (FIG. 5A). There was no difference in either the rate of expansion (FIG. 10), the overall specificity or magnitude of the response directed against each antigen, irrespective of the composition of the stimulating pepmix pool (FIG. 5B). Thus, all further studies used the mastermix (condition D). FIG. 5C shows 8 additional CTL lines with consistent multivirus specificity. The highest responses were seen against CMV-pp65 and Adv-Hexon (951.6±82.1 and 461.4±19.2 SFC/1×10$^5$ CTL) while activity against HHV6-U90, EBV-BZLF1 and EBV-LMP2 was weakest (26.9±4.2, 35.6±5, 39.6±2.6 SFC/1×10$^5$ CTL). Adv-Penton, Influenza-MP1 and RSV-F demonstrated intermediate response rates (191±13.7, 117.6±8.6, 90.1±10.3 SFC/1×10$^5$ CTL, respectively) (FIG. 5C). The lines were polyclonal and polyfunctional with activity against the stimulating viruses detectable in both CD4+ and CD8+ fractions (FIG. 5D), and reactive cells produced both IFNγ and TNFα superior in vivo activity[32, 33]. FIG. 5E shows the results for one representative donor in whom 63% of all Adv, 55% of CMV, 40% of EBV, 46% of RSV, 36% of Influenza and 28% of HHV6-specific CTLs produced both IFNγ and TNFα after antigenic stimulation. ICS for IFNγ and/or TNFα showed that 67.7±13.3% of all T cells in multivirus cultures were antigen-specific. This percentage is likely an underestimate since some virus-specific CTLs do not produce cytokines or produce effector cytokines other than IFNγ and TNFα[33]. Finally, even though these CTLs had received only a single stimulation there was no evidence of alloreactivity, assessed by Cr[51] release assay using HLA-mismatched PHA blasts as targets (FIG. 10), an important consideration if these cells are to be used for the treatment of allogeneic HSCT recipients.

Example 7

Multivirus-Specific CTL can be Expanded In Vitro

Figure 6A:
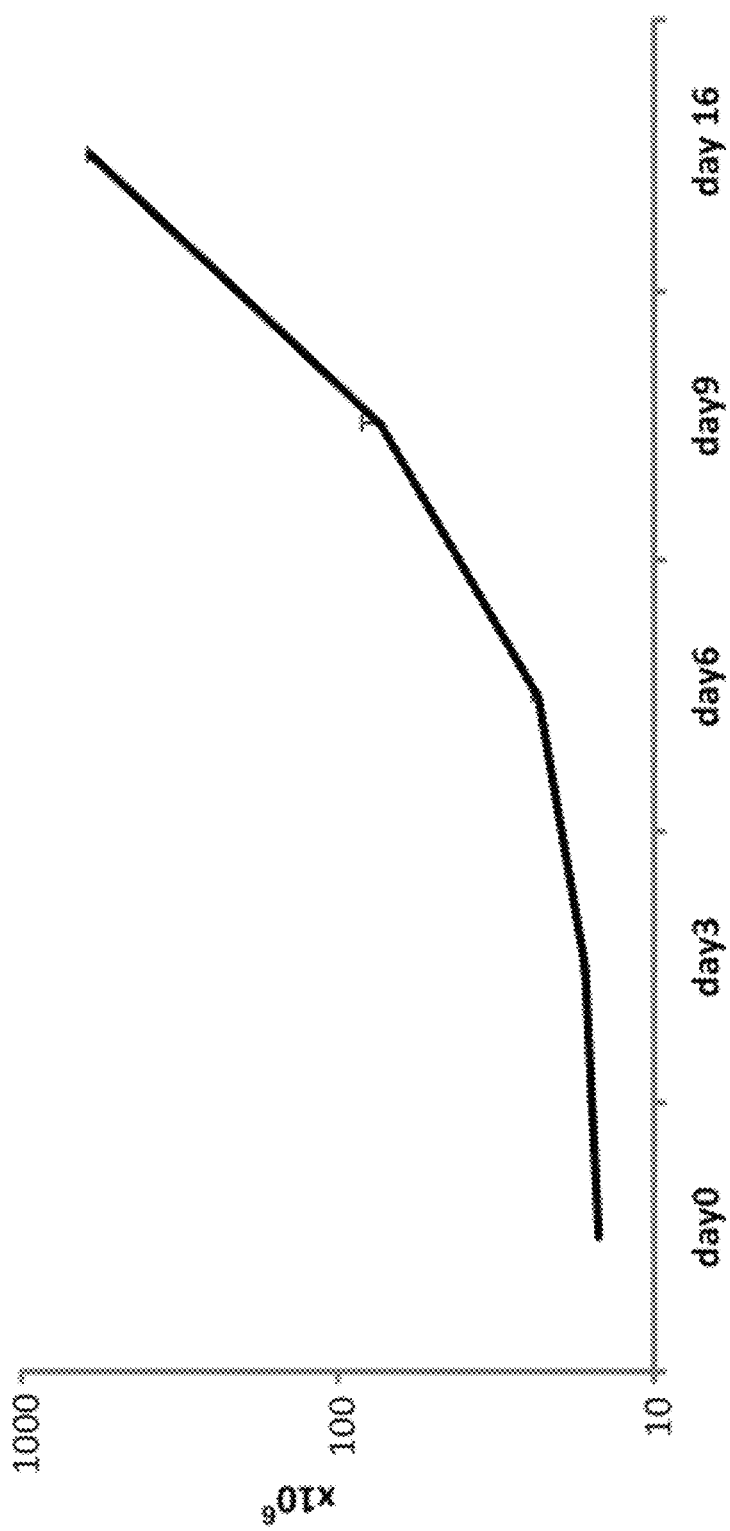
FIGS. 6A-6D: Multivirus-specific CTLs can be expanded in vitro. On day 9 after initial stimulation CTLs were restimulated using pepmix-pulsed PHA blasts.
Figure 6B:
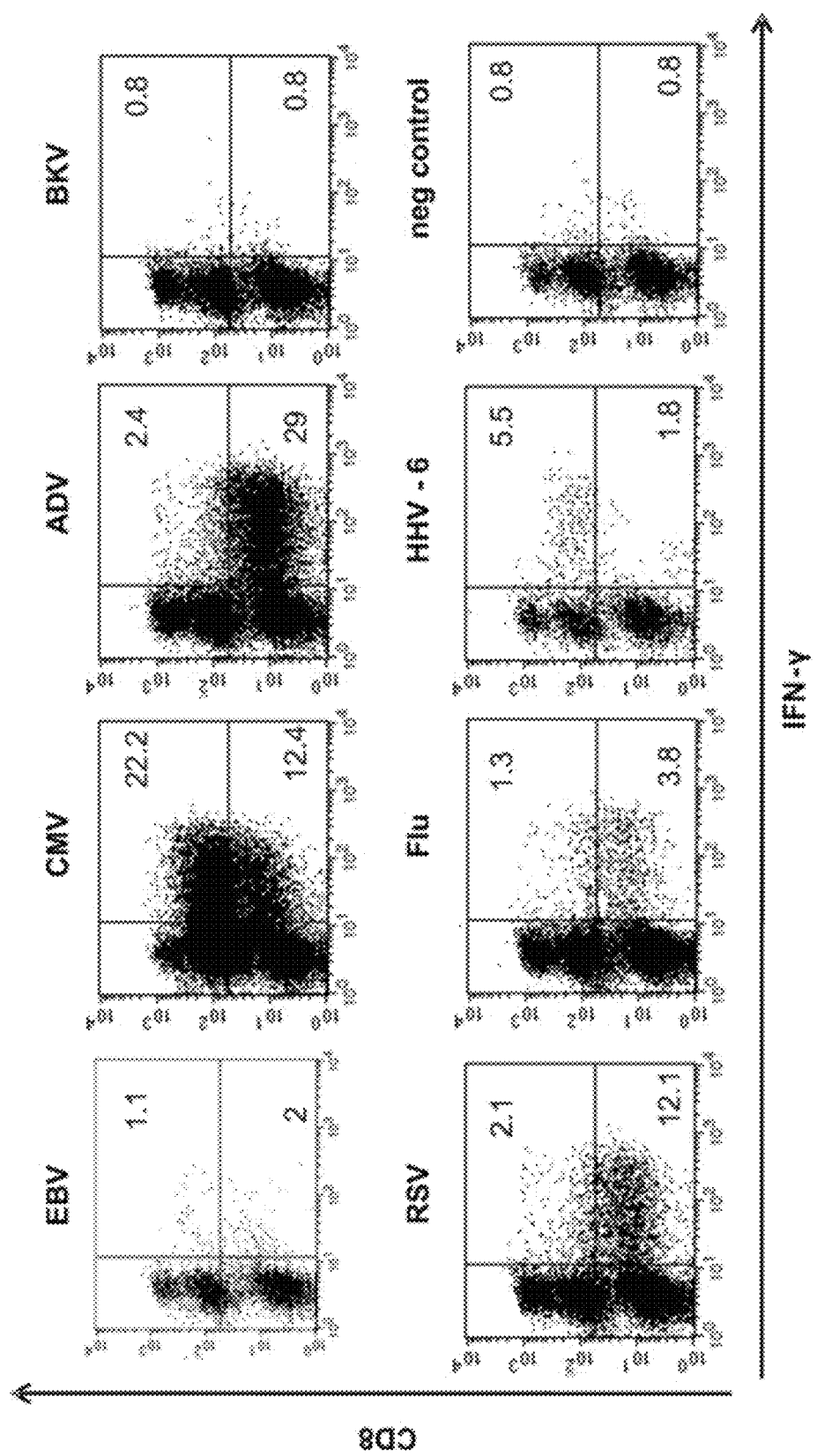
Figure 6C:
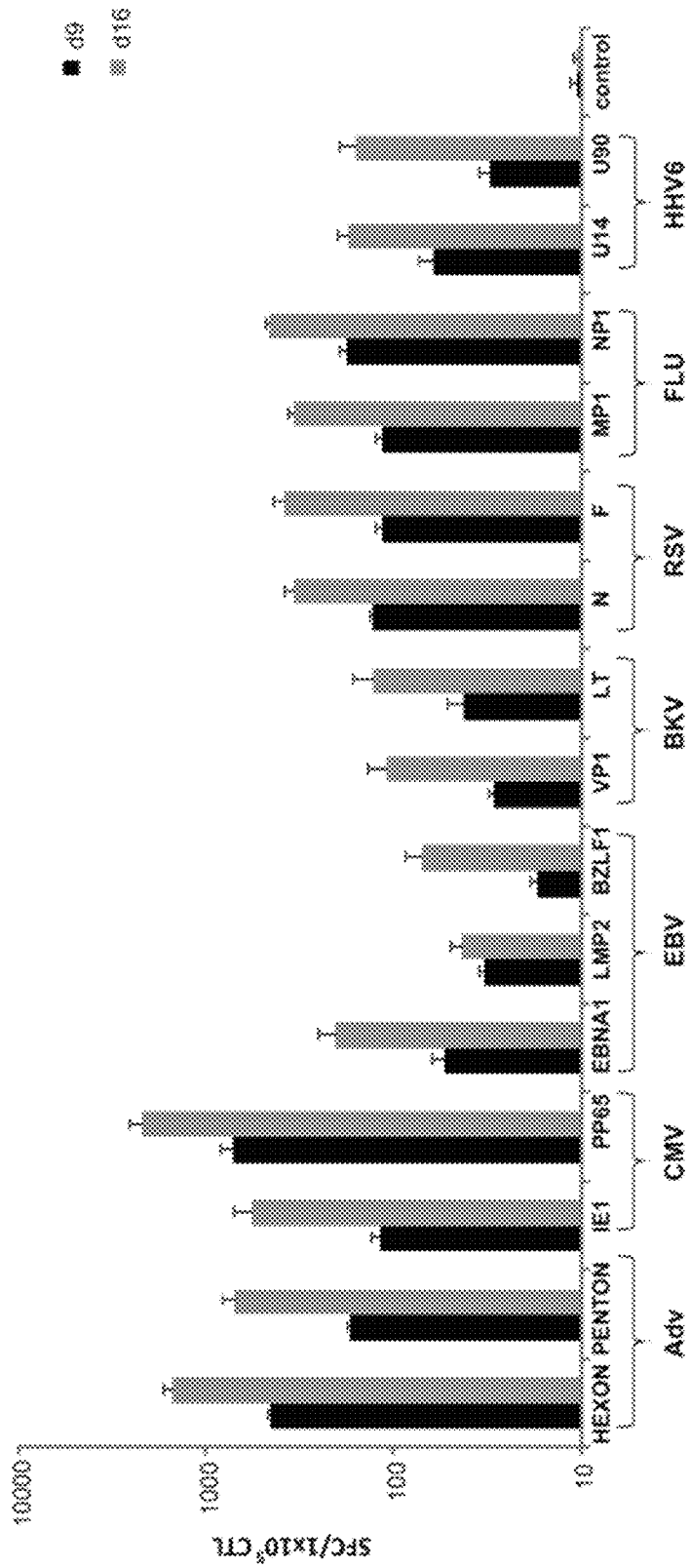
Figure 6D:
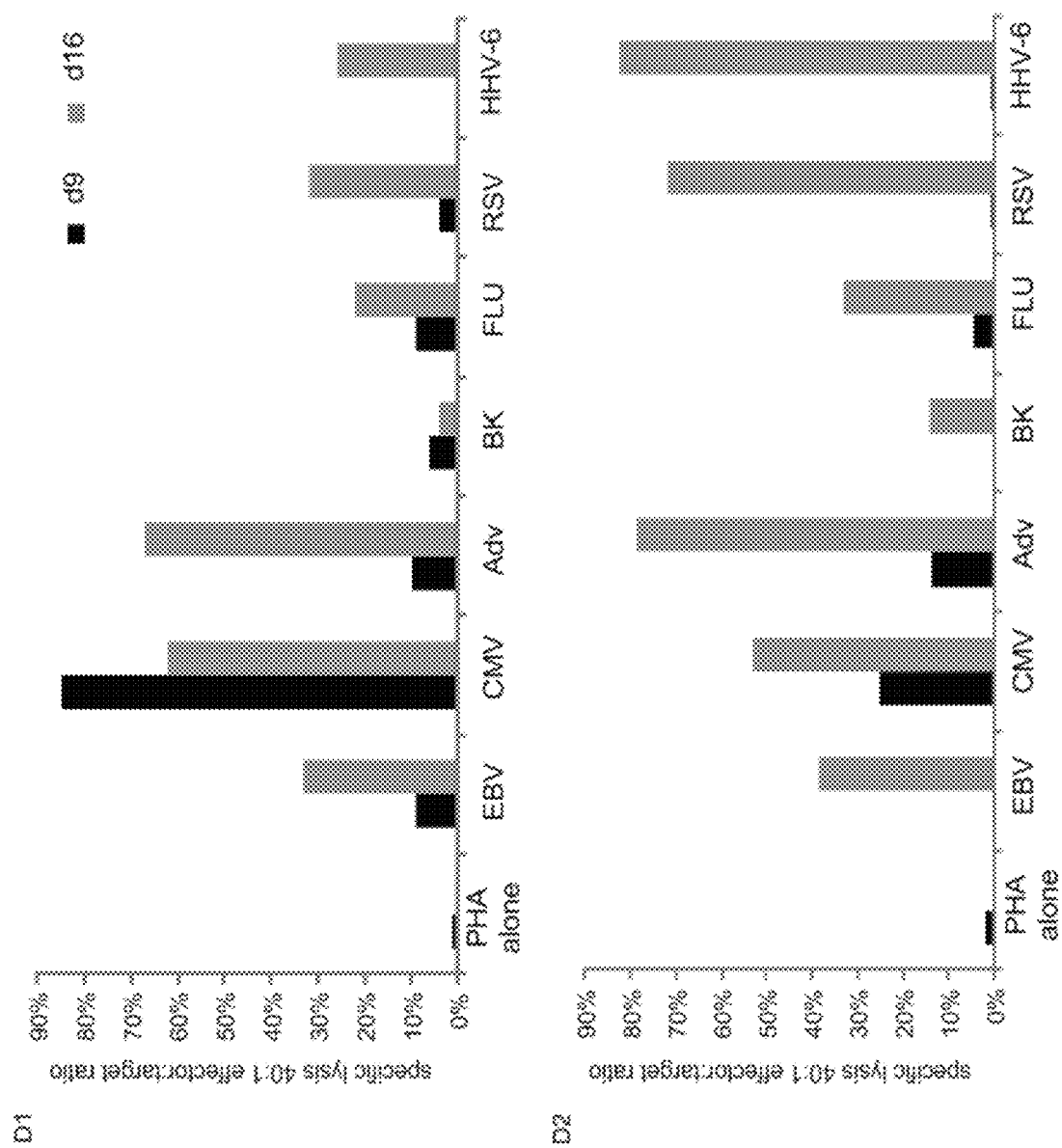
Figure 11:
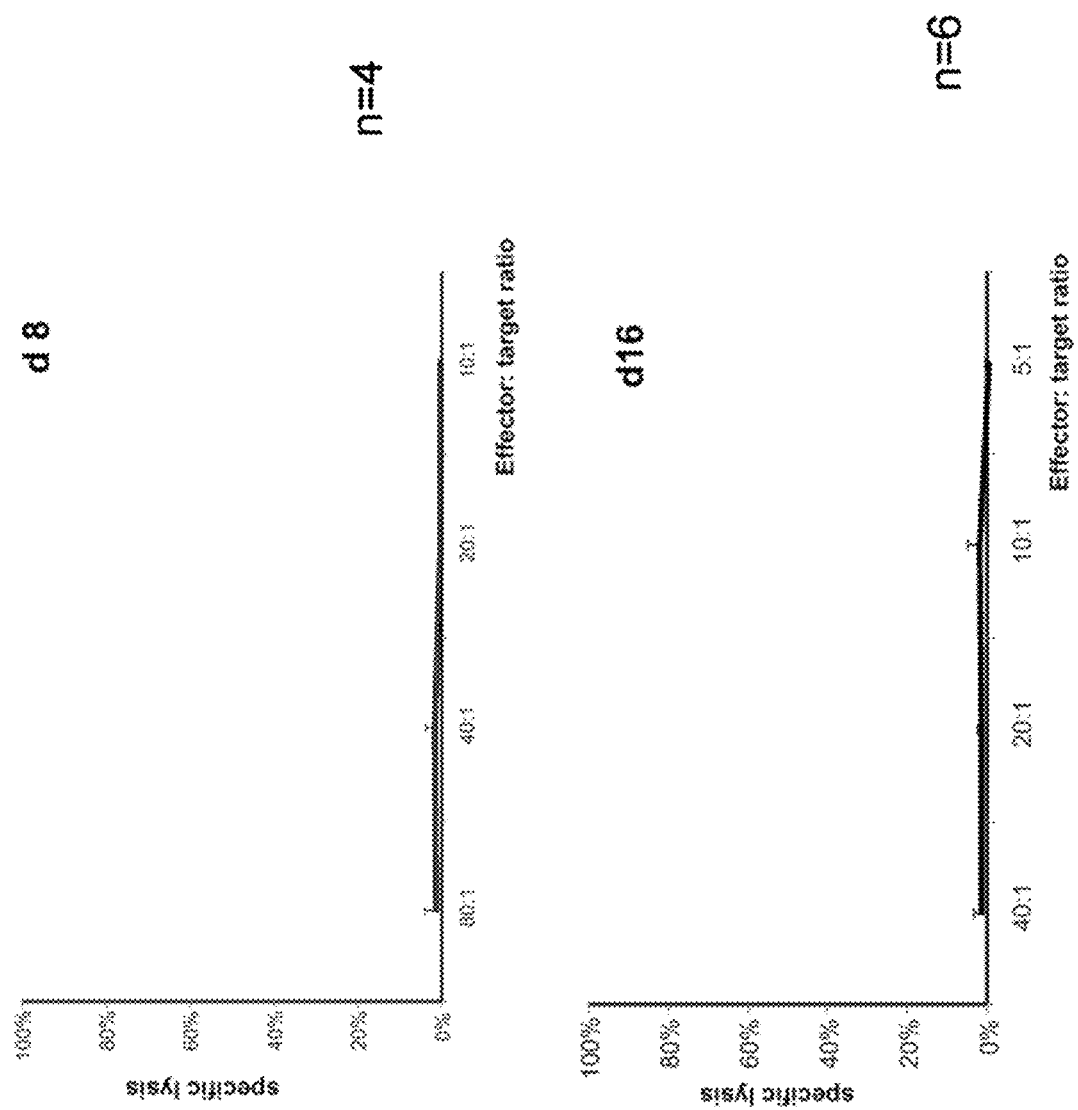
FIG. 11: Lack of alloreactivity in pepmix-stimulated PBMCs. The alloreactive potential of pepmix-activated CTL stimulated either once (n=4) or twice (n=2) was tested by $Cr^{51}$ release assay against a range of allogeneic HLA-mismatched PHA blasts as targets.

To discover whether multivirus-specific CTLs could be further expanded to provide numbers suited for third party or "off-the-shelf" use, the inventors restimulated the cells with autologous PHA blasts pulsed with the same mastermix of pepmixes. Secondary expansion of a mean of 8.4±2 fold was obtained over 7 days, to a final cell number of 604.6±23.7× 106 (FIG. 6A). FIG. 6B shows that the expanded CTLs remained polyclonal, with activity detected in both CD4+ and CD8+ compartments. Expansion was associated with an overall increase in the magnitude of the response directed against all of the stimulating antigens on day 16 relative to day 9 (FIG. 6C) so that >80% of cells in the restimulated cultures produced IFNγ and/or TNFα. Similarly, these expanded cultures had greater cytolytic activity, ranging from >60% (CMV) to 14% (BK), demonstrating retained specificity for both sub-dominant and immunodominant antigens/viruses without alloreactivity (FIG. 11).

Example 8

Significance of Certain Embodiments of the Invention

The inventors have shown that in at least some embodiments they can rapidly generate polyclonal, CD4+ and CD8+ T cells with specificities directed to a wide range of lytic and latent viruses responsible for infection in the immunocompromised host and after HSCT. These cells were Th1-polarized, had high avidity for a multiplicity of individual viral antigens, produced multiple effector cytokines upon stimulation, and killed virus-infected targets without alloreactivity. Because the inventors generated these T cells using combinations of clinically-available peptide-libraries and pro-survival cytokines, our approach should be well suited to clinical application.

While CMV, EBV and Adv are the most frequently detected viral infections following allogeneic HSCT, recipients are also susceptible to numerous other viruses, including BK, JC, HHV6, HHV7, influenza, parainfluenza, coronavirus, and RSV, all of which may cause severe morbidity and mortality[1,2]. Several of these viruses are only seasonally detected (e.g. influenza, RSV) while others, such as HHV7, JC, and coronavirus, are infrequent, so that it is impracticable to cover all these pathogens post-transplant by generating individualized patient and single virus-specific T cell products. Hence, the inventors sought to develop a strategy that would enable the production of a single CTL line with simultaneous specificity for a multiplicity of antigens.

In the current clinical trials of virus-specific T cells, the inventors have used EBV-LCL, adenovectors and/or viral antigen-encoding DNA plasmids to generate virus-directed T cells[7-9, 20, 21]. The use of full-length antigen ensures that CTL can be generated from all donors, irrespective of HLA, and that the antigen is physiologically processed by APCs and produces CTLs that recognize multiple CD4+ and CD8+ T cell epitopes and have sufficient avidity to kill virus-infected targets. The induction of lines that recognize multiple epitopes also minimizes virus escape due to epitope loss and produces potent and sustained anti-viral activity in vivo[34]. However, the requirements for live virus/vectors are barriers to broader and late phase clinical studies, and also limit the number of pathogens to which a single T cell line can be directed 8, 9. The inventors therefore evaluated whether clinically applicable pepmixes could be used as an alternative. Though clinical studies using minimal epitope peptides as vaccines have resulted in immune tolerance or the activation of low avidity T cells[35], Melief and colleagues recently demonstrated improved results with long (22-45aa) peptides containing both CD4+ and CD8+ epitope sequences[36]. They observed that these long peptides were processed endogenously, presented to T cells by APCs, and induced both helper and cytotoxic T cells, resulting in robust and effective CTL responses[36]. Based on these data, the inventors chose to use a whole antigen source in the form of overlapping peptide libraries, but for optimal induction of polyclonal CTL the inventors compared peptides of different lengths (15mers, 20mers and 30mers) for stimulation. However, the inventors saw no difference in the phenotype, specificity or epitope breadth of our lines, highlighting the differences between delivering peptides as a vaccine, where one relies on endogenous APCs to take up and process antigen versus in vitro T cell activation using professional APCs within PBMCs at optimal effector:target ratios[37]. Given the ready clinical availability of pepmixes containing 15mer peptides that cover all possible CD8+ and the majority of CD4+ epitopes, the inventors substituted this antigen source and were able to demonstrate equivalency to "conventionally generated" CTLs with respect to both epitope specificity and avidity[20, 21].

The inventors next addressed how best to extend the breadth of antigen/epitope specificities that could be accommodated within a single CTL line. Physiologically, T cells are activated when they receive signals from TCR stimulation (signal 1), co-stimulation (signal 2), and cytokines (signal 3). The "conventional CTLs" are activated in the absence of exogenous cytokines, a deficit that appears to adversely affect their proliferative capacity in vitro and also increases their susceptibility to activation induced cell death (AICD), likely resulting in a more restricted repertoire of epitope recognition. Consistent with this possibility, both the frequency and breadth of cells with viral specificity could be increased by supplementing cultures with inflammatory and pro-survival cytokines at initiation. The inventors chose to test cytokines that support cell proliferation in vitro and in vivo (IL2, IL15)[38,39], as well as combinations (IL4+7) that also support the retention of a central memory phenotype, and promote the survival of activated T cells by upregulation of anti-apoptotic molecules e.g. Bcl-2[40-43]. Only lines supplemented with IL4+7 selectively promoted the expansion and survival of both CD4+ and CD8+ virus-specific T cells: of note, the induced cells were Th1-polarized despite exposure to IL4, a prototypic Th2 cytokine. Given the clinical availability of both cytokines and their safety in human clinical trials[44, 45], IL4+7 fulfilled the requirements of the current study, however other pro-inflammatory cytokines capable of mimicking the milieu present during viral infection may produce similar benefits. For example, von Rossum and colleagues recently reported that CD3/28-activated CD8+ T cells cultured in an inflammatory cocktail consisting of IL1+IL6+IL23 underwent significantly less cell death after activation as compared with cells activated in any of the cytokines alone or activated in the presence of IL12[46].

The direct stimulation of PBMCs with pepmixes and culture in cytokine-supplemented conditions also allowed us to overcome a second major barrier to increasing the spectrum of viruses targeted in a single CTL line, namely antigenic competition resulting from the use of a common APC to simultaneously present multiple antigenic components from different viruses[8, 9]. Antigenic competition results both from limited access of peptides to HLA molecules and physical constraints on the simultaneous stimulation of both high and low frequency T cells[13, 14]. To overcome these issues, investigators have used artificial APCs (AAPCs) that are engineered with molecules to provide the necessary TCR and co-stimulatory events required for immune synapse formation[47]. However, to avoid the inevitable complexities and costs of introducing a gene-modified cellular product into the manufacturing process, the inventors evaluated whether patient PBMCs themselves could act as both a source of antigen presenting and responding cells. B cells, monocytes and macrophages may all have the capacity to present antigen to T cells and these APCs can utilize endo- and exopeptidases to liberate class I or class II epitopes from 15mer peptides[48, 49]. By taking advantage of these properties, the inventors can avoid reliance on a single APC endogenously expressing multiple antigens at different levels as a shared T cell stimulator, and instead have a diverse group of APCs in which each cell has the potential to display a diverse repertoire of peptides, allowing sufficient access for both high and low frequency T cells. Thus, antigenic competition both within the APC and between T cells could be alleviated. As proof of principle, the inventors generated a single culture of T cells with reactivity for 15 antigens derived from 7 latent and lytic viruses (EBV, CMV, BK, HHV6, Adv, Flu, and RSV) using pooled pepmixes as a stimulus and saw no evidence of competition. Additional pathogens can be included in this platform, although in some embodiments ultimately APC numbers can eventually become limiting; thus additions must be performed in a stepwise manner and one must evaluate changes in the frequency and breadth of T cell recognition of all peptides in the mix.

Critically for clinical feasibility, the approach was able to produce large numbers of virus-specific T cells. By seeding just $1.5 \times 10^7$ PBMCs in the G-Rex and a single in vitro stimulation the inventors could regularly manufacture $1 \times 10^8$ CTLs within 10 days, with a >10-fold enrichment in virus-specific cells and a corresponding reduction in alloreactive T cells to levels observed in repetitively stimulated conventional CTLs, which have a proven safety record in vivo[7-9, 50]. Thus, using our new manufacturing technology the inventors predict that multivirus-specific CTL will be safe for infusion after a single exposure to pepmixes and will provide broad spectrum anti-viral protection without GvHD. Should additional cells be required, for example if banked virus-specific CTLs are established for 3rd party recipients, a second stimulation using pepmix-pulsed PHA blasts can expand the total number of CTLs without impairing their epitope specificity or breadth.

Example 8

Exemplary Materials and Methods

A. Donors and Cell Lines

PBMCs were obtained from healthy volunteers with informed consent using a Baylor College of Medicine IRB-approved protocol. PBMCs were used to generate DCs, CTL lines and PHA blasts. PHA blasts were generated from PBMC ($2 \times 10^6$/ml) using PHA (5 µg/ml) and maintained in CTL media (RPMI 1640, 45% Click's (Irvine Scientific, Santa Ana, CA), 2 mM GlutaMAX TM-I, and 5% Human AB Serum) supplemented with IL2 (100 U/ml, NIH, Bethesda, VA), which was replenished every 3 days.

B. CTL Generation—Peptide Stimulation i. Peptides/Pepmixes

For PBMC stimulation the inventors used commercially available pepmixes (15mers overlapping by 11aa spanning EBV-LMP2, BZLF1, EBNA1; Adv-Penton, Hexon; CMV-pp65, IE-1; BKV-VP1, large T; Influenza A-MP1 (H3N2), NP (H3N2); RSV-F, N, JPT Technology, Berlin, Germany. Pepmixes spanning HHV6 U14 and U90 were synthesized by Genemed Synthesis Inc., San Antonio, Texas USA. Peptide libraries spanning the 414aa C-terminus of Adv-Hexon were synthesized by Proimmune, Oxford, UK or Alta Bioscience, University of Birmingham, Edgbaston, Birmingham, UK. Lyophilized peptides were reconstituted at 5 mg/ml in DMSO.

ii. PBMC Stimulation $15 \times 10^6$ fresh/frozen PBMCs were pelleted in a 15 ml tube and pulsed for 30-60 min at 37° C. with peptide libraries/pepmixes, either singly or pooled, at a concentration of 100 ng/peptide/$15 \times 10^6$ PBMCs. After incubation cells were resuspended in CTL media alone or supplemented with cytokines (as outlined below) and transferred to a G-Rex10 (Wilson Wolf Manufacturing Corporation, New Brighton, MN) ($15 \times 10^6$/G-Rex10) or plated out in a 24-well plate ($2 \times 10^6$/well). Media and cytokines were replenished on day 5, and cultures were split when they reached a density>$50 \times 10^6$/G-Rex10 or >$3 \times 10^6$ cell/24-well. On day 9-12, CTLs were harvested, counted and used for phenotypic and functional studies.

iii. Cytokines for Promoting CTL Activation and Expansion

The inventors compared 4 conditions; (i) no cytokine, (ii) IL7 (10 ng/ml)+IL4 (1666 U/ml), (iii) IL15 (5 ng/ml) (R&D Systems, Minneapolis, MN) and (iv) IL2 (20 U/ml). Cytokines were added to CTLs at day 0 and replenished on day 5. In some embodiments, 400 U of IL4 is employed.

iv. CTL Expansion

For expansion CTLs were restimulated at a S:R ratio of 1:1 with irradiated (30 Gy) pepmix-pulsed autologous PHA blasts in CTL media with IL4+7 and IL15 (5 ng/ml) on the day of restimulation and fed with IL15 twice weekly. Seven days later CTLs were harvested, and used for further studies.

C. Flow Cytometry i. Immunophenotyping

CTLs were surface-stained with monoclonal antibodies to: CD3, CD4, CD8, CD16, CD56, CD28, CD45RO, and CD62L (Becton Dickinson BD, Franklin Lakes, NJ). Cells were washed once with phosphate-buffered saline (PBS) (Sigma, St Louis, MO) containing 2% FBS (HyClone, Thermo Fisher Scientific Inc, NH), pelleted, and antibodies added in saturating amounts (10 µl). After 15 min at 4° C. in the dark, cells were washed twice and analyzed. Approximately 20,000 live cells were acquired using a FACSCalibur equipped with Cell Quest software ii. CFSE To measure cell proliferation PBMCs were isolated, pelleted and pulsed with pp65 pepmix (100 ng/$15 \times 10^6$ PBMC) for 30-60 min. Next PBMCs were washed twice using PBS+0.1% FBS and incubated for 10 min with 1501/$20 \times 10^6$ PBMC 10 μM CSFE. Subsequently FBS was added at a 1:1 ratio and incubated for 10 min at 37° C. After CFSE labeling PBMCs were washed twice using PBS+2% FBS and plated at a concentration of 1×10⁶/ml in CTL media with cytokines. Dilution of CFSE was examined every 2-3 days by flow after surface staining with CD3, CD4, CD8 and CD56.

iii. FoxP3 Staining

To measure regulatory T cells Foxp3 staining was performed using the e-Bioscience FoxP3 staining kit. Briefly, CTLs were rested in CTL media for 48 h, then 1×10⁶ CTLs were resuspended in PBS+2% FBS and surface stained for CD3, CD25 and CD4. After washing the cells were resuspended in 1 ml Fixation/Permeabilizastion solution and incubated for 1 h at 4° C., then washed, resuspended in permeabilization buffer and incubated with 0.41 isotype or 10 μl FoxP3 antibody (Clone PCH101) for 30 min at 4° C. After a final wash cells were acquired using a FACSCalibur equipped with Cell Quest software.

iv. Intracellular Cytokine Staining

CTLs were harvested, resuspended at a concentration of 5×10⁶/ml in CTL media and plated at 200 μl/well in a 96 well plate. The cells were then stimulated with 100 ng of test or control pepmix in the presence of Brefeldin A (1 μg/ml), (BD) CD28 and CD49d (1 μg/ml) for 5-7 hours. Subsequently, CTLs were washed with PBS+2% FBS, pelleted, and surface stained with CD8, CD4 and CD3 (10 μl/antibody/tube). After 15 mins, cells were washed twice, pelleted, fixed and permeabilized with Cytofix/Cytoperm solution (BD) for 20 mins at 4° C. in the dark. After washing twice with PBS/2% FBS containing 0.1% saponin (Calbiochem, EMD Chemicals, NJ) cells were incubated with 20 μl IFNγ and/or TNFα antibodies (BD) for 30 min at 4° C. in the dark. Cells were then washed twice with cold PBS/2% FBS containing 0.1% saponin and at least 200,000 live cells from each population were analyzed with a FACSCalibur equipped with Cell Quest software (BD).

D. Functional Studies i. Multiplex Assay

To assess cytokine production the inventors used a multiplex assays. 1×105 pp65-CTLs were restimulated using 500 ng/ml pp65 or control pepmix. After 16 hrs supernatant was collected and the cytokine profile assessed using the MILLIPLEX High Sensitivity Human Cytokine Magnetic Bead Panel (Millipore, Billerica, MA). Specifically, 50 μl supernatant was incubated overnight at 4° C. with cytokine antibody beads. After incubation, samples were washed and incubated for 1 hr at room temperature (RT) with the biotinylated detection antibody. Finally Streptavidin-Phycoerythrin was added for 30 min at RT, then samples were washed and analyzed using the Luminex 200 instrument. Samples were run in duplicate.

ii. Enzyme-linked Immunospot Assay

The inventors used ELISpot to quantify IFNγ-producing T cells and assess the breadth of reactivity in the CTL lines. The populations were serially diluted from 4-1×10⁵ cells/well, and antigen-specific activity measured after direct pepmix or peptide mini-pool stimulation. Each condition was run in triplicate. After 20 hours, plates were developed as previously described[22], dried overnight at RT, then sent to Zellnet Consulting, New York, NY for quantification. SFC and input cell numbers were plotted, and a linear regression calculated after excluding plateau data points.

iii. TCR Avidity Assessment

TCR avidity was assessed by IFN ELIspot. 2×10⁵ CTLs were stimulated with serial dilutions of pepmixes (pp65, Hexon) or 9mer peptides (NLV-pp65: NLVPMVATV HLA-A2 restricted, QYD-pp65: QYDPVAALF HLA-A24 restricted; TDL-Hexon: TDLGQNLLY HLA-A1 restricted). The frequency of T cells specific for each antigen/peptide was expressed as a percentage of the maximal SFC/input cell number.

iv. Chromium Release Assay

The inventors measured the cytotoxic specificity in a standard 4 hr $Cr^{51}$ release assay, using E:T ratios of 40:1, 20:1, 10:1, and 5:1. CTLs were used as effectors and the targets were PHA blasts pulsed with pepmixes. Autologous and allogeneic PHA blasts alone or loaded with an irrelevant pepmix were used as specificity and alloreactivity controls. The percentage of specific lysis was calculated as [(experimental release−spontaneous release)/(maximum release−spontaneous release)]×100.

REFERENCES

All patents and publications mentioned in this specification are indicative of the level of those skilled in the art to which the invention pertains. All patents and publications herein are incorporated by reference to the same extent as if each individual publication was specifically and individually indicated to be incorporated by reference in their entirety.

PUBLICATIONS

1. Schonberger S, Meisel R, Adams 0, et al. Prospective, comprehensive and effective viral monitoring in children undergoing allogeneic hematopoietic stem cell transplantation. Biol. Blood Marrow Transplant. 2010.
2. Verdeguer A, de Heredia C D, Gonzalez M, et al. Observational prospective study of viral infections in children undergoing allogeneic hematopoietic cell transplantation: a 3-year GETMON experience. Bone Marrow Transplant. 2011; 46(1):119-124.
3. Lang P, Handgretinger R. Haploidentical SCT in children: an update and future perspectives. Bone Marrow Transplant. 2008; 42 Suppl 2:S54-S59.
4. Sauter C, Abboud M, Jia X, et al. Serious infection risk and immune recovery after double-unit cord blood transplantation without antithymocyte globulin. Biol. Blood Marrow Transplant. 2011; 17(10):1460-1471.
5. Hantz S, Garnier-Geoffroy F, Mazeron M C, et al. Drug-resistant cytomegalovirus in transplant recipients: a French cohort study. J. Antimicrob. Chemother. 2010; 65(12):2628-2640.
6. Ljungman P, Ribaud P, Eyrich M, et al. Cidofovir for adenovirus infections after allogeneic hematopoietic stem cell transplantation: a survey by the Infectious Diseases Working Party of the European Group for Blood and Marrow Transplantation. Bone Marrow Transplant. 2003; 31(6):481-486.
7. Heslop H E, Brenner M K, Rooney C M. Donor T cells to treat EBV-associated lymphoma. N Engl J Med. 1994; 331:679-680.
8. Leen A M, Myers G D, Sili U, et al. Monoculture-derived T lymphocytes specific for multiple viruses expand and produce clinically relevant effects in immunocompromised individuals. Nat. Med. 2006; 12(10): 1160-1166.
9. Leen A M, Christin A, Myers G D, et al. Cytotoxic T lymphocyte therapy with donor T cells prevents and treats adenovirus and Epstein-Barr virus infections after haploidentical and matched unrelated stem cell transplant. Blood. 2009.
10. Barker J N, Doubrovina E, Sauter C, et al. Successful treatment of EBV-associated posttransplantation lymphoma after cord blood transplantation using third-party EBV-specific cytotoxic T lymphocytes. Blood. 2010; 116 (23):5045-5049.
11. Hague T, Wilkie G M, Taylor C, et al. Treatment of Epstein-Barr-virus-positive posttransplantation lymphoproliferative disease with partly HLA-matched allogeneic cytotoxic T cells. Lancet. 2002; 360(9331):436-442.
12. Hague T, Wilkie G M, Jones M M, et al. Allogeneic cytotoxic T-cell therapy for EBV-positive posttransplantation lymphoproliferative disease: results of a phase 2 multicenter clinical trial. Blood. 2007; 110(4): 1123-1131.
13. Kedl R M, Rees W A, Hildeman D A, et al. T cells compete for access to antigen-bearing antigen-presenting cells. J. Exp. Med. 2000; 192(8):1105-1113.
14. Kedl R M, Schaefer B C, Kappler J W, Marrack P. T cells down-modulate peptide-MHC complexes on APCs in vivo. Nat. Immunol. 2002; 3(1):27-32.
15. Leen A, Ratnayake M, Foster A, et al. Contact-activated monocytes: efficient antigen presenting cells for the stimulation of antigen-specific T cells. J. Immunother. (1997). 2007; 30(1):96-107.
16. Cobbold M, Khan N, Pourgheysari B, et al. Adoptive transfer of cytomegalovirus-specific CTL to stem cell transplant patients after selection by HLA-peptide tetramers. J. Exp. Med. 2005; 202(3):379-386.
17. Feuchtinger T, Matthes-Martin S, Richard C, et al. Safe adoptive transfer of virus-specific T-cell immunity for the treatment of systemic adenovirus infection after allogeneic stem cell transplantation. British Journal of Haematology. 2006; 134(1):64-76.
18. Feuchtinger T, Opherk K, Bethge W A, et al. Adoptive transfer of pp65-specific T cells for the treatment of chemorefractory cytomegalovirus disease or reactivation after haploidentical and matched unrelated stem cell transplantation. Blood. 2010; 116(20):4360-4367.
19. Khanna N, Stuehler C, Conrad B, et al. Generation of a multipathogen-specific T-cell product for adoptive immunotherapy based on activation-dependent expression of CD154. Blood. 2011; 118(4):1121-1131.
20. Gerdemann U, Vera J F, Rooney C M, Leen A M. Generation of multivirus-specific T cells to prevent/treat viral infections after allogeneic hematopoietic stem cell transplant. J. Vis. Exp. 2011; (51).
21. Gerdemann U, Christin A C, Vera J F, et al. Nucleofection of DCs to Generate Multivirus-specific T Cells for Prevention or Treatment of Viral Infections in the Immunocompromised Host. Molecular Therapy. 2009.
22. Fujita Y, Leen A M, Sun J, et al. Exploiting cytokine secretion to rapidly produce multivirus-specific T cells for adoptive immunotherapy. J. Immunother. 2008; 31(7): 665-674.
23. Walter E A, Greenberg P D, Gilbert M J, et al. Reconstitution of cellular immunity against cytomegalovirus in recipients of allogeneic bone marrow by transfer of T-cell clones from the donor. N. Engl. J. Med. 1995; 333(16): 1038-1044.
24. Kern F, Faulhaber N, Frommel C, et al. Analysis of CD8 T cell reactivity to cytomegalovirus using protein-spanning pools of overlapping pentadecapeptides. Eur J Immunol. 2000; 30(6): 1676-1682.
25. Leen A M, Sili U, Savoldo B, et al. Fiber-modified adenoviruses generate subgroup cross-reactive, adenovirus-specific cytotoxic T lymphocytes for therapeutic applications. Blood. 2004; 103 (3): 1011-1019.
26. Leen A M, Christin A, Khalil M, et al. Identification of hexon-specific CD4 and CD8 T-cell epitopes for vaccine and immunotherapy. Journal of Virology. 2008; 82(1): 546-554.
27. Bunde T, Kirchner A, Hoffmeister B, et al. Protection from cytomegalovirus after transplantation is correlated with immediate early 1-specific CD8 T cells. J. Exp. Med. 2005; 201(7): 1031-1036.
28. Micklethwaite K P, Clancy L, Sandher U, et al. Prophylactic infusion of cytomegalovirus-specific cytotoxic T lymphocytes stimulated with Ad5f35pp65 gene-modified dendritic cells after allogeneic hemopoietic stem cell transplantation. Blood. 2008; 112(10):3974-3981.
29. Bollard C M, Gottschalk S, Huls M H, et al. In vivo expansion of LMP1- and LMP2-specific T-cells in a patient who received donor-derived EBV-specific T-cells after allogeneic stem cell transplantation. Leuk. Lymphoma. 2006; 47(5):837-842.
30. Falco D A, Nepomuceno R R, Krams S M, et al. Identification of Epstein-Barr virus-specific CD8+ T lymphocytes in the circulation of pediatric transplant recipients. Transplantation. 2002; 74(4): 501-510.
31. Jones K, Nourse J P, Morrison L, et al. Expansion of EBNA1-specific effector T cells in posttransplantation lymphoproliferative disorders. Blood. 2010; 116(13): 2245-2252.
32. Badr G, Bedard N, bdel-Hakeem M S, et al. Early interferon therapy for hepatitis C virus infection rescues polyfunctional, long-lived CD8+ memory T cells. Journal of Virology. 2008; 82(20): 10017-10031.
33. Kannanganat S, Ibegbu C, Chennareddi L, Robinson H L, Amara R R. Multiple-cytokine-producing antiviral CD4 T cells are functionally superior to single-cytokine-producing cells. Journal of Virology. 2007; 81(16):8468-8476.
34. Heslop H E, Slobod K S, Pule M A, et al. Long-term outcome of EBV-specific T-cell infusions to prevent or treat EBV-related lymphoproliferative disease in transplant recipients. Blood. 2010; 115(5):925-935.
35. Toes R E, Offringa R, Blom R J, Melief C J, Kast W M. Peptide vaccination can lead to enhanced tumor growth through specific T-cell tolerance induction. Proc. Natl. Acad. Sci. U.S.A. 1996; 93(15):7855-7860.
36. Kenter G G, Welters M J, Valentijn A R, et al. Vaccination against HPV-16 oncoproteins for vulvar intraepithelial neoplasia. N. Engl. J. Med. 2009; 361(19):1838-1847.
37. Toes R E, van d, V, Schoenberger S P, et al. Enhancement of tumor outgrowth through CTL tolerization after peptide vaccination is avoided by peptide presentation on dendritic cells. J. Immunol. 1998; 160(9):4449-4456.
38. Rosenberg S A, Yannelli J R, Yang J C, et al. Treatment of patients with metastatic melanoma with autologous tumor-infiltrating lymphocytes and interleukin 2. J. Natl. Cancer Inst. 1994; 86(15): 1159-1166.
39. Becker T C, Wherry E J, Boone D, et al. Interleukin 15 is required for proliferative renewal of virus-specific memory CD8 T cells. J. Exp. Med. 2002; 195(12):1541-1548.
40. Vella A T, Dow S, Potter T A, Kappler J, Marrack P. Cytokine-induced survival of activated T cells in vitro and in vivo. Proc. Natl. Acad. Sci. U.S.A. 1998; 95(7):3810-3815.
41. Tan J T, Ernst B, Kieper W C, LeRoy E, Sprent J, Surh C D. Interleukin (IL)-15 and IL-7 jointly regulate homeostatic proliferation of memory phenotype CD8+ cells but 42. Melchionda F, Fry T J, Milliron M J, McKirdy M A, Tagaya Y, Mackall C L. Adjuvant IL-7 or IL-15 overcomes immunodominance and improves survival of the CD8+ memory cell pool. J. Clin. Invest. 2005; 115(5): 1177-1187.
43. Chetoui N, Boisvert M, Gendron S, Aoudjit F. Interleukin-7 promotes the survival of human CD4+ effector/memory T cells by up-regulating Bcl-2 proteins and activating the JAK/STAT signalling pathway. Immunology. 2010; 130(3):418-426.
44. Sportes C, Babb R R, Krumlauf M C, et al. Phase I study of recombinant human interleukin-7 administration in subjects with refractory malignancy. Clin. Cancer Res. 2010; 16(2):727-735.
45. Majhail N S, Hussein M, Olencki T E, et al. Phase I trial of continuous infusion recombinant human interleukin-4 in patients with cancer. Invest New Drugs. 2004; 22(4): 421-426.
46. von R A, Krall R, Escalante N K, Choy J C. Inflammatory cytokines determine the susceptibility of human CD8 T cells to Fas-mediated activation-induced cell death through modulation of FasL and c-FLIP(S) expression. J. Biol. Chem. 2011; 286(24):21137-21144.
47. Maus M V, Thomas A K, Leonard D G, et al. Ex vivo expansion of polyclonal and antigen-specific cytotoxic T lymphocytes by artificial APCs expressing ligands for the T-cell receptor, CD28 and 4-1B B. Nat. Biotechnol. 2002; 20(2):143-148.
48. Kessler J H, Khan S, Seifert U, et al. Antigen processing by nardilysin and thimet oligopeptidase generates cytotoxic T cell epitopes. Nat. Immunol. 2011; 12(1):45-53.
49. Larsen S L, Pedersen L O, Buus S, Stryhn A. T cell responses affected by aminopeptidase N (CD13)-mediated trimming of major histocompatibility complex class II-bound peptides. J. Exp. Med. 1996; 184(1): 183-189.
50. Melenhorst J J, Leen A M, Bollard C M, et al. Allogeneic virus-specific T cells with HLA alloreactivity do not produce GVHD in human subjects. Blood. 2010; 116(22): 4700-4702.
51. Culver K W, Ram Z, Wallbridge S, Ishii H, Oldfield E H, Blaese R M, In vivo gene transfer with retroviral vector-producer cells for treatment of experimental brain tumors. Science. 1992 Jun. 12; 256(5063):1550-2.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A method of providing a cell therapy to an individual in need thereof, comprising administering a composition to the individual, wherein the composition comprises an ex vivo expanded polyclonal population of cytotoxic human T lymphocytes (CTLs) that target two or more viral antigens from two or more different viruses, wherein the CTLs are polyclonal CD4+ and CD8+ CTLs;
    wherein one or more antigens is from a first virus, and one or more antigens is from a second virus; and wherein
    (a) the first virus is BK virus, and the one or more antigens are selected from LT and VP-1; and
    (b) the second virus is HHV6 virus, and the one or more antigens are selected from U14, U11, U71, U54, and U90.
2. The method of claim 1, wherein the individual has a viral infection.
3. The method of claim 1, wherein the individual is at risk of a viral infection.
4. The method of claim 1, wherein the individual is an immunocompromised individual.
5. The method of claim 1, wherein the individual has had an allogeneic stem cell transplant.
6. The method of claim 1, wherein the CTLs do not induce detectable evidence of alloreactivity.
7. The method of claim 1, wherein the composition is administered to the individual by intravenous injection.
8. The method of claim 1, wherein the composition is formulated as a pharmacological formulation.
9. The method of claim 8, wherein the composition is administered to the individual by intravenous injection.
10. A method of providing a cell therapy to an individual in need thereof, comprising administering the composition to the individual, wherein the composition comprises an ex vivo expanded population of cytotoxic human T cells (CTLs) that target two or more viral antigens from two or more different viruses, wherein the CTLs are polyclonal CD4+ and CD8+ CTLs reactive to one or more libraries of peptides, said one or more libraries of peptides each comprising peptides that overlap in sequence or span part or all of said two or more viral antigens, wherein each peptide is at least seven amino acids in length,
    wherein one or more antigens is from a first virus, and one or more antigens is from a second virus; and wherein
    (a) the first virus is BK virus, and the one or more antigens are selected from LT and VP-1; and
    (b) the second virus is HHV6 virus, and the one or more antigens are selected from U14, U11, U71, U54, and U90.
11. The method of claim 10, wherein the peptides overlap in sequence by at least three amino acids.
12. The method of claim 10, wherein the peptides are 15 amino acids in length and overlap by 11 amino acids.
13. The method of claim 12, wherein the peptides span the entire length of each of the multiple antigens.
14. The method of claim 10, wherein the individual has a viral infection.
15. The method of claim 10, wherein the individual is at risk of a viral infection.
16. The method of claim 10, wherein the individual is an immunocompromised individual.
17. The method of claim 10, wherein the individual has had an allogeneic stem cell transplant.
18. The method of claim 10, wherein the CTLs do not induce detectable evidence of alloreactivity.
19. The method of claim 10, wherein the composition is administered to the individual by intravenous injection.
20. The method of claim 10, wherein the composition is formulated as a pharmacological formulation.

21. The method of claim 20, wherein the composition is administered to the individual by intravenous injection.

\* \* \* \* \*